(12) United States Patent
Lahm et al.

(10) Patent No.: US 7,897,630 B2
(45) Date of Patent: Mar. 1, 2011

(54) 5-ARYL ISOXAZOLINES FOR CONTROLLING INVERTEBRATE PESTS

(75) Inventors: George Philip Lahm, Wilmington, DE (US); Kanu Maganbhai Patel, Wilmington, DE (US); Thomas Francis Pahutski, Jr., Elkton, MD (US); Benjamin Kenneth Smith, Newark, DE (US); Jeffrey Keith Long, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/083,944

(22) PCT Filed: Dec. 15, 2006

(86) PCT No.: PCT/US2006/047999
§ 371 (c)(1),
(2), (4) Date: Apr. 21, 2008

(87) PCT Pub. No.: WO2007/075459
PCT Pub. Date: Jul. 5, 2007

(65) Prior Publication Data
US 2009/0133319 A1 May 28, 2009

Related U.S. Application Data

(60) Provisional application No. 60/751,226, filed on Dec. 16, 2005, provisional application No. 60/752,511, filed on Dec. 21, 2005, provisional application No. 60/849,037, filed on Oct. 3, 2006.

(51) Int. Cl.
| | |
|---|---|
| C07D 417/10 | (2006.01) |
| C07D 413/10 | (2006.01) |
| C07D 261/04 | (2006.01) |
| A61K 31/506 | (2006.01) |
| A61K 31/4439 | (2006.01) |
| A61K 31/427 | (2006.01) |
| A61K 31/422 | (2006.01) |
| A61K 31/42 | (2006.01) |

(52) U.S. Cl. ............ 514/378; 514/365; 514/374; 514/372; 514/340; 514/256; 548/203; 548/214; 548/235; 548/240; 546/272.1; 544/333

(58) Field of Classification Search ............ 548/240; 514/378
See application file for complete search history.

(56) References Cited

U.S. PATENT DOCUMENTS 6,645,984 B2 * 11/2003 Braun et al. .......... 514/326

| | | | |
|---|---|---|---|
| 2005/0250822 A1 | 11/2005 | Mita et al. | |
| 2007/0066617 A1 | 3/2007 | Mita et al. | |
| 2010/0173948 A1 | 7/2010 | Lahm et al. | |
| 2010/0179195 A1 | 7/2010 | Lahm et al. | |

FOREIGN PATENT DOCUMENTS

| | | | |
|---|---|---|---|
| CA | 2558848 A1 | | 9/2005 |
| EP | 1538138 A1 | | 6/2005 |
| EP | 1731512 A1 | | 12/2006 |
| EP | 1731512 A1 | * | 12/2006 |
| GB | 2351081 A | * | 12/2000 |
| JP | 2007/016017 | | 1/2007 |
| JP | 2007016017 A | * | 1/2007 |
| JP | 2007/106756 | | 4/2007 |
| JP | 2007106756 A | * | 4/2007 |
| WO | WO2005/085216 A1 | | 9/2005 |
| WO | WO2005/094329 A2 | | 10/2005 |
| WO | WO2007/070606 A2 | | 6/2007 |
| WO | 2007/079162 A1 | | 7/2007 |
| WO | WO2008/019760 A1 | | 2/2008 |
| WO | 2009/002809 A2 | | 12/2008 |
| WO | 2009/002809 A3 | | 12/2008 |
| WO | 2009/045999 A1 | | 4/2009 |

* cited by examiner

Primary Examiner—Joseph R Kosack
Assistant Examiner—Matthew P Coughlin

(57) ABSTRACT

Disclosed are compounds of Formula 1, including all geometric and stereoisomers, N-oxides, and salts thereof wherein $A^1$, $A^2$ and $A^3$ are independently selected from the group consisting of $CR^3$ and N; $B^1$ $B^2$ and $B^3$ are independently selected from the group consisting of $CR^2$ and N; Q is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsufinyl, $C_1$-$C_6$ alkylsulfonyl, $C_1$-$C_6$ haloalkylsulfonyl, —CN, —$NO_2$, —N($R^4$)$R^5$, —C(W)N(R4)$R^5$, —C(O)O$R^5$ and $R^8$; or —S(O)$_2$N($R^{21}$)$R^{22}$; —S(O)$_p$$R^{25}$ or —S(O)(=N$R^{28}$)$R^{29}$; $R^1$, $R^2$, $R^3$, $R^4$, $R^5$, $R^8$, $R^{21}$, $R^{22}$, $R^{25}$, $R^{28}$, $R^{29}$; p and n are as defined in the disclosure. Also disclosed are compositions containing the compounds of Formula 1 and methods for controlling an invertebrate pest comprising contacting the invertebrate pest or its environment with a biologically effective amount of a compound or a composition of the invention.

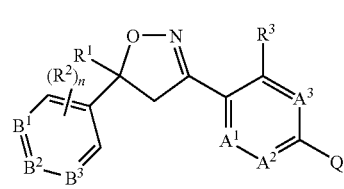

(1)

33 Claims, No Drawings

5-ARYL ISOXAZOLINES FOR CONTROLLING INVERTEBRATE PESTS

FIELD OF THE INVENTION

This invention relates to certain isoxazolines, their N-oxides, salts and compositions suitable for agronomic and nonagronomic uses, including those uses listed below, and methods of their use for controlling invertebrate pests such as arthropods in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes, but the need continues for new compounds that are more effective, less costly, less toxic, environmentally safer or have different modes of action.

PCT Patent Publication WO 05/085216 discloses isoxazoline derivatives of Formula 1 as insecticides

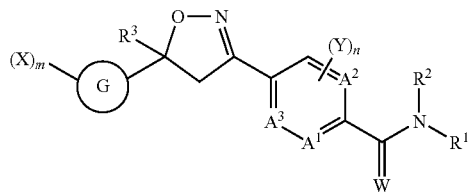

wherein, inter alia, each of $A^1$, $A^2$ and $A^3$ are independently C or N; G is a benzene ring; W is O or S; and X is halogen or $C_1$-$C_6$ haloalkyl.

SUMMARY OF THE INVENTION

This invention is directed to compounds of Formula 1 including all geometric and stereoisomers, N-oxides, and salts thereof, and compositions containing them and their use for controlling invertebrate pests:

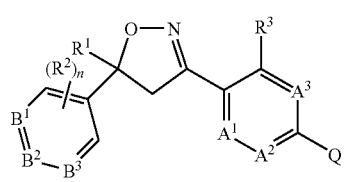

wherein:

$A^1$, $A^2$ and $A^3$ are independently selected from the group consisting of $CR^3$ and N;

$B^1$, $B^2$ and $B^3$ are independently selected from the group consisting of $CR^2$ and N;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_2$-$C_6$ alkenyl, $C_3$-$C_6$ haloalkenyl, $C_2$-$C_6$ alkynyl, $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —N($R^4$)$R^5$, —C(W)N($R^4$)$R^5$, —C(W)O$R^5$, —CN or —$NO_2$;

Q is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —N($R^4$)$R^5$, —C(W)N($R^4$)$R^5$, —C(O)O$R^5$ and $R^8$; or —S(O)$_2$N($R^{21}$)$R^{22}$, —S(O)$_p$$R^{25}$ or —S(O)(=N$R^{28}$)$R^{29}$;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN, —$NO_2$ or $Q^1$;

each $R^8$ is independently a phenyl ring or a pyridinyl ring, each ring optionally substituted with one or more substituents independently selected from $R^9$;

each $R^9$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —COOH, —CN or —$NO_2$;

each $Q^1$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, —C(W)N($R^{10}$)$R^{11}$, —C(O)O$R^{11}$ and $R^{12}$;

each $R^{10}$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{11}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or $R^{12}$;

each $R^{12}$ is independently a phenyl ring or a pyridinyl ring, each ring optionally substituted with one or more substituents independently selected from $R^{13}$;

each $R^{13}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —COOH, —CN or —$NO_2$;

$R^{21}$ is H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{22}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{23}$;

each $R^{23}$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$; or a phenyl ring or a pyridinyl ring, each ring optionally substituted with one or more substituents independently selected from $R^{24}$;

each $R^{24}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —COOH, —CN or —$NO_2$;

$R^{25}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{26}$;

each $R^{26}$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylcarbonyl, $C_2$-$C_7$ alkoxycarbonyl, —CN or —$NO_2$; or a phenyl ring or a pyridinyl ring, each ring optionally substituted with one or more substituents independently selected from $R^{27}$;

each $R^{27}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —COOH, —CN or —$NO_2$;

$R^{28}$ is H, halogen, —CN, —$NO_2$, $C_2$-$C_7$ alkylcarbonyl, $C_2$-$C_7$ haloalkylcarbonyl, $C_2$-$C_7$ alkoxycarbonyl, $C_2$-$C_7$ alkylaminocarbonyl, $C_3$-$C_7$ dialkylaminocarbonyl, $C_1$-$C_6$ alkylsulfonyl or $C_1$-$C_6$ haloalkylsulfonyl; or $R^{28}$ is $C_1$-$C_6$ alkyl, $C_3$-$C_6$ cycloalkyl, ($C_1$-$C_6$ alkoxy)-($C_1$-$C_6$ alkyl) or $C_1$-$C_6$ alkylthio, each optionally substituted with halogen, $C_1$-$C_6$ alkyl, $C_1$-$C_6$ haloalkyl, $C_1$-$C_6$ cycloalkyl, $C_1$-$C_6$ halocycloalkyl, $C_1$-$C_6$ alkoxy, $C_1$-$C_6$ haloalkoxy, —CN or —$NO_2$;

$R^{29}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{26}$;

each W is independently O or S;

p is 0, 1 or 2; and n is 0, 1 or 2.

This invention also provides a composition comprising a compound of Formula 1, an N-oxide or a salt thereof, and at least one additional component selected from the group consisting of a surfactant, a solid diluent and a liquid diluent. In one embodiment, this invention also provides a composition for controlling an invertebrate pest comprising a biologically effective amount of a compound of Formula 1, an N-oxide or a salt thereof, and at least one additional component selected from the group consisting of a surfactant, a solid diluent and a liquid diluent, said composition optionally further comprising a biologically effective amount of at least one additional biologically active compound or agent.

This invention further provides a spray composition for controlling an invertebrate pest comprising a biologically effective amount of a compound of Formula 1, an N-oxide or a salt thereof, or the composition described above and a propellant. The present invention also provides the composition described above in the form of a spray composition wherein the liquid diluent is a propellant. This invention also provides a bait composition for controlling an invertebrate pest comprising a biologically effective amount of a compound of Formula 1, an N-oxide or a salt thereof, or the composition described in the embodiment above, one or more food materials, optionally an attractant, and optionally a humectant. This invention further provides the composition described above in the form of a bait composition wherein the solid diluent and/or the liquid diluent comprises one or more food materials, said composition optionally comprising an attractant and/or a humectant.

This invention further provides a trap device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

This invention also provides a method for controlling an invertebrate pest comprising contacting the invertebrate pest or its environment with a biologically effective amount of a compound of Formula 1, an N-oxide or a salt thereof, (e.g., as a composition described herein). This invention also relates to such method wherein the invertebrate pest or its environment is contacted with a composition comprising a biologically effective amount of a compound of Formula 1, an N-oxide or a salt thereof, and at least one additional component selected from the group consisting of a surfactant, a solid diluent and a liquid diluent, said composition optionally further comprising a biologically effective amount of at least one additional biologically active compound or agent.

This invention also provides a method for protecting a seed from an invertebrate pest comprising contacting the seed with a biologically effective amount of a compound of Formula 1, an N-oxide or a salt thereof. This invention further relates to a treated seed comprising a compound of Formula 1, an N-oxide or a salt thereof, in an amount of from about 0.0001 to 1% by weight of the seed before treatment.

This invention also provides a composition for protecting an animal from an invertebrate parasitic pest comprising a parasiticidally effective amount of a compound of Formula 1; an N-oxide or a salt thereof, and at least one carrier. The present invention further provides the composition described above in a form for oral administration. This invention also provides a method for protecting an animal from an invertebrate parasitic pest comprising administering to the animal a parasiticidally effective amount of a compound of Formula 1, an N-oxide or a salt thereof.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes; pill bugs and symphylans. The term "gastropod" includes snails, slugs and other Stylommatophora. The term "helminths;" includes worms in the phyla of Nemathelminthes, Platyhelminthes and Acanthocephala such as: round worms, heartworms, and phytophagous nematodes (Nematoda), flukes (Trematoda), tape worms (Cestoda) and thorny-headed worms.

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives). The term "nonagronomic" refers to settings other than field crops; such as other horticultural crops (e.g.; greenhouse, nursery or ornamental plants not grown in a field), residential, agricultural, commercial and industrial structures, turf (e.g., sod farm, pasture, golf course, residential lawn, recreational sports field, etc.), wood products, stored product; agro-forestry and vegetation management, public health (human) and animal health (e.g., domesticated animals such as pets, livestock and poultry, undomesticated animals such as wildlife) applications.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)-$, $CH_3CH_2S(O)-$, $CH_3CH_2CH_2S(O)-$, $(CH_3)_2CHS(O)-$ and the different butylsulfinyl, pentylsulfinyl and hexylsulfinyl isomers. Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl, pentylsulfonyl and hexylsulfonyl isomers. "Alkylamino", "dialkylamino", and the like, are defined analogously to the above examples. "Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C-$, $ClCH_2-$, $CF_3CH_2-$ and $CF_3CCl_2-$. The terms "halocycloalkyl", "haloalkoxy", "haloalkylthio", and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(O)-$, $CCl_3S(O)-$, $CF_3CH_2S(O)-$ and $CF_3CF_2S(O)-$. Examples of "haloalkylsulfonyl" include $CF_3S(O)_2-$, $CCl_3S(O)_2-$, $CF_3CH_2S(O)_2-$ and $CF_3CF_2S(O)_2-$.

"Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3C(=O)-$, $CH_3CH_2C(=O)$, $CH_3CH_2CH_2OC(=O)-$, $(CH_3)_2CHOC(=O)-$ and the different butoxy- or pentoxycarbonyl isomers.

The total number of carbon atoms in a substituent group is indicated by the prefix where i and j are numbers from 1 to 7. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can exceed 1, said substituents (when they exceed 1) are independently selected from the group of defined substituents, e.g., $(R^2)_n$, n is 1 or 2. When a group contains a substituent which can be hydrogen, for example $R^2$, then when this substituent is taken as hydrogen, it is recognized that this is equivalent to said group being unsubstituted.

"Aromatic" indicates that each of the ring atoms is essentially in the same plane and has a p-orbital perpendicular to the ring plane, and in which $(4n+2)\pi$ electrons, where n is a positive integer, are associated with the ring to comply with Hückl's rule.

The terms "heterocyclic ring" or "heterocycle" denote a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring", "aromatic heterocyclic ring". Unless otherwise indicated, heterocyclic rings and ring systems can be attached through any available carbon or nitrogen by replacement of a hydrogen on said carbon or nitrogen.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other, When Q is a 5- or 6-membered nitrogen-containing heterocyclic ring, it may be attached to the remainder of Formula 1 though any available carbon or nitrogen ring atom, unless otherwise described. Similarly, when $Q^1$ is a 5- or 6-membered nitrogen-containing heterocycle, it may be attached through any available carbon or nitrogen ring atom, unless otherwise described.

As noted above, Q or $Q^1$ can be (among others) phenyl optionally substituted with one or more substituents selected from a group of substituents as defined in the Summary of Invention. An example of phenyl optionally substituted with one to five substituents is the ring illustrated as U-1 in Exhibit 1, wherein $R^v$ is selected from a group of substituents as defined in the Summary of the Invention for Q or $Q^1$ and r is an integer from 0 to 5.

As noted above, Q or $Q^1$ can be (among others) 5- or 6-membered heterocyclic ring, which may be saturated or unsaturated, optionally substituted with one or more substituents selected from a group of substituents as defined in the Summary of Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for Q or $Q^1$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

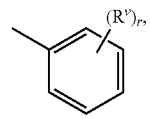
U-1

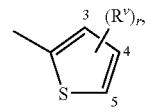
U-2

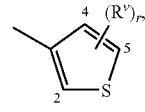
U-3

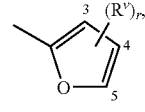
U-4

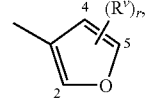
U-5

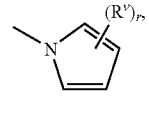
U-6

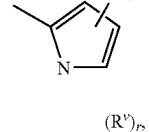
U-7

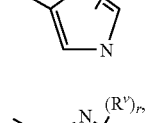
U-8

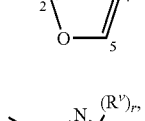
U-9

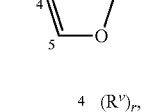
U-10

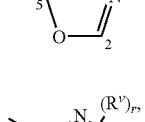
U-11

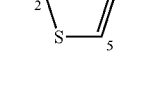
U-12

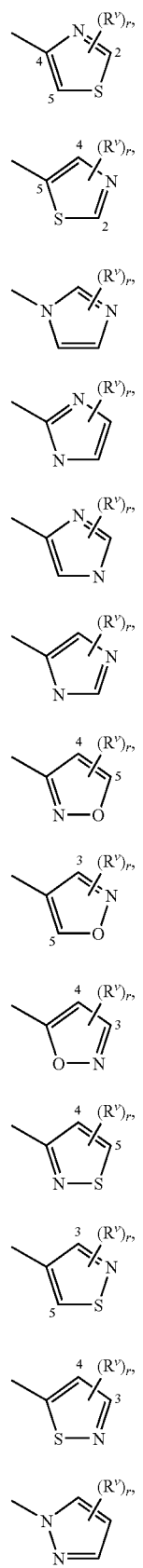
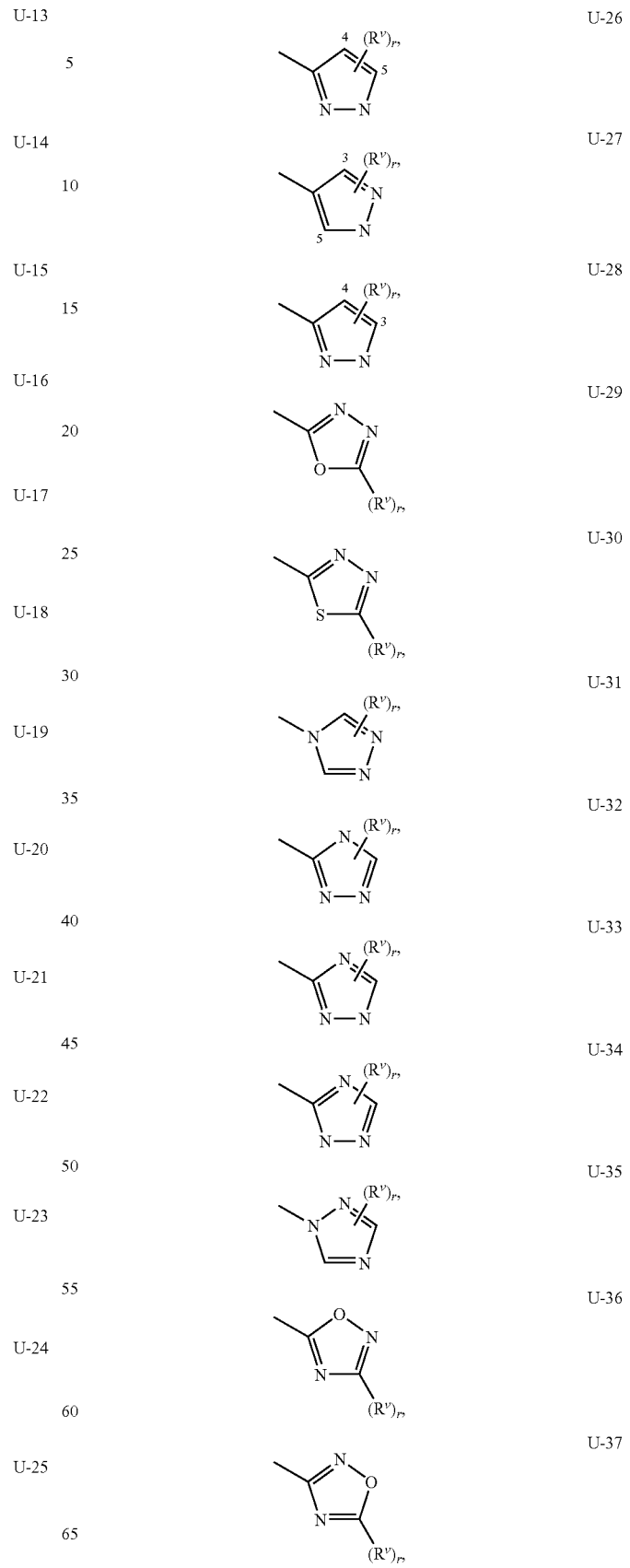

-continued
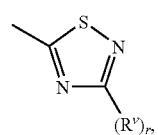 U-38
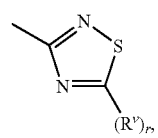 U-39
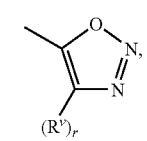 U-40
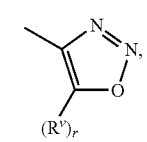 U-41
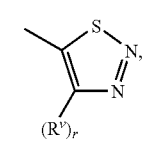 U-42
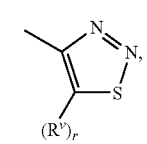 U-43
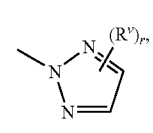 U-44
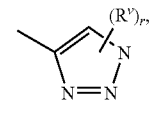 U-45
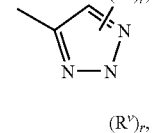 U-46
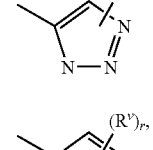 U-47
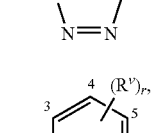 U-48
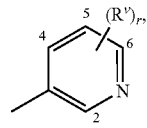 U-49
-continued
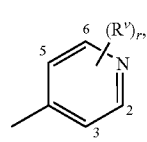 U-50
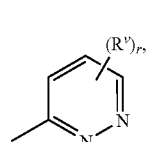 U-51
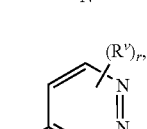 U-52
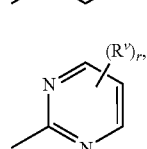 U-53
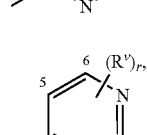 U-54
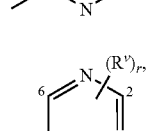 U-55
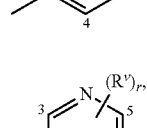 U-56
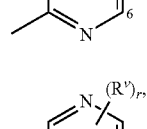 U-57
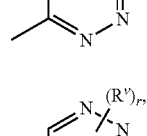 U-58
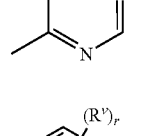 U-59
 U-60
, and -continued

U-61

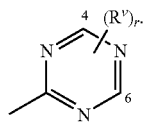

Although R$^v$ groups are shown in the structures U-1 through U-61, it is noted that they do not need to be present since they are optional substituents. Note that when R$^v$ is H and attached to an atom, this is the same as if said atom is unsubstituted. The nitrogen atoms that require substitution to fill their valence are substituted with H or R$^v$. Note that when the attachment point between (R$^v$)$_r$ and the U group is illustrated as floating, (R$^v$)$_r$ can be attached to any available carbon atom or nitrogen atom of the U group. Note that when the attachment point on the V group is illustrated as floating, the U group can be attached to the remainder of Formula 1 through any available carbon or nitrogen of the U group by replacement of a hydrogen atom. Note that some U groups can only be substituted with less than 4 R$^v$ groups (e.g., U-2 through U-5, U-7 through U-48, and U-52 through U-61).

Note that when Q or Q$^1$ is a 5- or 6-membered saturated or unsaturated non-aromatic heterocyclic ring optionally substituted with one or more substituents selected from the group of substituents as defined in the Summary of Invention for Q or Q$^1$, one or two carbon ring members of the heterocycle can optionally be in the oxidized form of a carbonyl moiety.

Examples of a 5- or 6-membered saturated or non-aromatic unsaturated heterocyclic ring include the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to R$^v$ can be attached to any available carbon or nitrogen by replacing a hydrogen atom. For these G rings, r is typically an integer from 0 to 4, limited by the number available positions on each G group.

Note that when Q or Q$^1$ comprises a ring selected from G-28 through G-35, G$^2$ is selected from O, S or N. Note that when G$^2$ is N, the nitrogen atom can complete its valence by substitution with either H or the substituents as defined in the Summary of Invention for Q or Q$^1$.

G-1
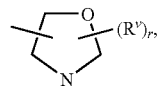

G-2
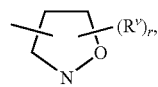

G-3
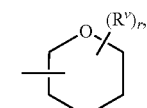

G-4
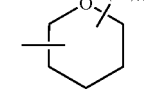

-continued

G-5
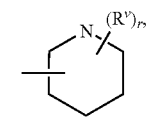

G-6
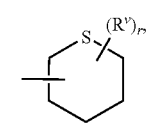

G-7
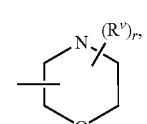

G-8
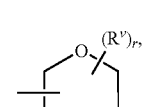

G-9
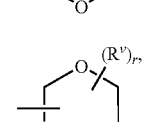

G-10
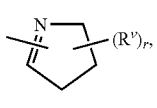

G-11
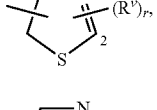

G-12
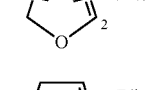

G-13
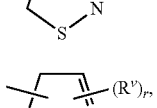

G-14
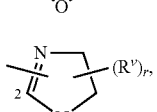

G-15
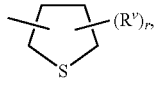

G-16
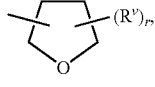

G-17
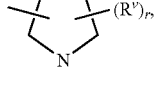

G-18
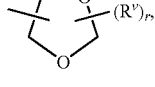

-continued

G-19 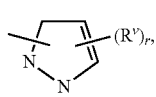

G-20 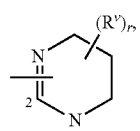

G-21 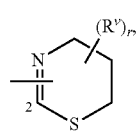

G-22 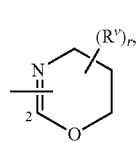

G-23 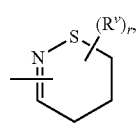

G-24 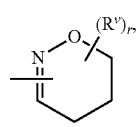

G-25 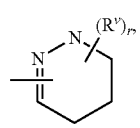

G-26 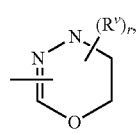

G-27 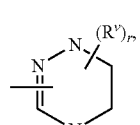

G-28 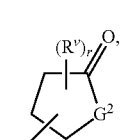

G-29 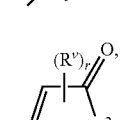

G-30 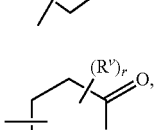

-continued

G-31 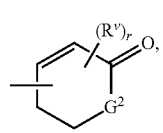

G-32 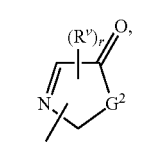

G-33 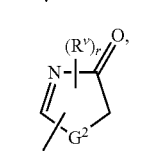

G-34 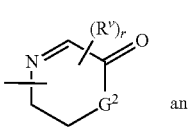

and

G-35 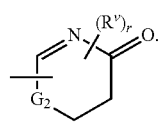

A wide variety of synthetic methods are known in the art to enable preparation or aromatic and nonaromatic heterocyclic rings; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

One skilled in the art will appreciate that not all nitrogen containing heterocyclic rings can form N-oxides since the nitrogen requires an available lone pair for oxidation to the oxide; one skilled in the art will recognize those nitrogen containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive*

*Heterocyclic Chemistry*, vol. 3, pp 19-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry, vol. 9*, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include:

Embodiment 1. A compound of Formula 1 wherein $R^1$ is $C_1$-$C_3$ alkyl optionally substituted with one or more substituents independently selected from $R^6$.

Embodiment 2. A compound of Embodiment 1 wherein $R^1$ is $C_1$-$C_3$ alkyl optionally substituted with halogen.

Embodiment 3. A compound of Embodiment 2 wherein $R^1$ is $C_1$-$C_3$ alkyl substituted with halogen.

Embodiment 4. A compound of Embodiment 3 wherein $R^1$ is $C_1$-$C_3$ alkyl substituted with F.

Embodiment 5. A compound of Embodiment 4 wherein $R^1$ is $C_1$-$C_3$ alkyl fully substituted with F.

Embodiment 6. A compound of Embodiment 5 wherein $R^1$ is $CF_3$.

Embodiment 7. A compound of Formula 1 wherein each $R^2$ is independently H, halogen, $C_1$-$C_6$ haloalkyl, $C_1$-$C_6$ haloalkoxy or CN.

Embodiment 8. A compound of Embodiment 7 wherein each $R^2$ is independently H, halogen, $CF_3$, $OCF_3$ or —CN.

Embodiment 9. A compound of Embodiment 7 wherein each $R^2$ is independently H or halogen.

Embodiment 10. A compound of Formula 1 wherein each $R^3$ is independently H, halogen, $C_1$-$C_6$ alkyl, $C_1$-$C_6$ haloalkyl, $C_2$-$C_6$ alkenyl, $C_3$-$C_6$ haloalkenyl, $C_2$-$C_6$ alkynyl, $C_3$-$C_6$ haloalkynyl, $C_3$-$C_6$ cycloalkyl, $C_1$-$C_6$ alkoxy, $C_1$-$C_6$ haloalkoxy, —N($R^4$)$R^5$, —C(W)N($R^4$)$R^5$, —CN or —$NO_2$.

Embodiment 11. A compound of Embodiment 10 wherein each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$.

Embodiment 12. A compound of Embodiment 11 wherein each $R^3$ is independently H, halogen, $C_1$-$C_2$ alkyl, —C≡CH, —CN or —$NO_2$.

Embodiment 13. A compound of Embodiment 12 wherein each $R^3$ is H.

Embodiment 14. A compound of Embodiment 12 wherein each $R^3$ is —CN.

Embodiment 15. A compound of Formula 1 wherein Q is a phenyl ring, a pyridinyl ring, a pyrimidinyl ring, a triazinyl ring, a pyrazolyl ring, a triazolyl ring, a tetrazolyl ring, an imidazolyl ring, an oxazolyl ring, an isoxazolyl ring, a thiazolyl ring or an isothiazolyl ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —N($R^4$)$R^5$, —C(W)N($R^4$)$R^5$, —C(O)$OR^5$ and $R^8$.

Embodiment 16. A compound of Embodiment 15 wherein Q is a pyrazolyl ring, a triazolyl ring, a tetrazolyl ring or an imidazolyl ring, each ring attached through nitrogen and optionally substituted with one or more substituents independently selected from halogen, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, —CN, —$NO_2$, —N($R^4$)$R^5$, —C(N($R^4$)$R^5$, —C(O)$OR^5$ and $R^8$.

Embodiment 17. A compound of Embodiment 16 wherein Q is a pyrazolyl ring, a triazolyl ring, a tetrazolyl ring or an imidazolyl ring, each ring attached through nitrogen and optionally substituted with one or more substituents independently selected from halogen, $C_1$-$C_4$ alkyl, $C_1$-$C_4$ haloalkyl, —CN and —$NH_2$.

Embodiment 18. A compound of Embodiment 17 wherein Q is a pyrazolyl ring, a triazolyl ring, a tetrazolyl ring or an imidazolyl ring, each ring attached through nitrogen.

Embodiment 19. A compound of Formula 1 wherein each $R^4$ is independently H, $C_1$-$C_4$ alkyl, $C_2$-$C_4$ alkylcarbonyl or $C_2$-$C_4$ alkoxycarbonyl.

Embodiment 20. A compound of Embodiment 19 wherein each $R^4$ is H.

Embodiment 21. A compound of Formula 1 wherein each $R^5$ is independently H; or $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^7$.

Embodiment 22. A compound of Embodiment 21 wherein each $R^5$ is independently H; or $C_1$-$C_4$ alkyl optionally substituted with one or more substituents independently selected from $R^7$.

Embodiment 23. A compound of Embodiment 22 wherein each $R^5$ is independently H or $C_1$-$C_4$ alkyl.

Embodiment 24. A compound of Formula 1 wherein each $R^7$ is independently halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$-alkylsulfonyl, —CN, —$NO_2$ or $Q^1$.

Embodiment 25. A compound of Formula 1 wherein $Q^1$ is a phenyl ring, a pyridinyl ring, a thiazolyl ring, a pyrazolyl ring, a triazolyl ring or an imidazolyl ring, each ring optionally substituted with one or more substituents independently selected from halogen, $C_1$-$C_3$ alkyl, $C_1$-$C_3$ haloalkyl, —CN, —C(W)N($R^{10}$)$R^{11}$, C(O)$OR^{11}$ and $R^{12}$.

Embodiment 26. A compound of Formula 1 wherein each $R^{10}$ is independently H, $C_1$-$C_4$ alkyl, $C_2$-$C_4$ alkylcarbonyl or $C_2$-$C_4$ alkoxycarbonyl.

Embodiment 27. A compound of Embodiment 26 wherein each $R^{10}$ is H.

Embodiment 28. A compound of Formula 1 wherein each $R^{11}$ is independently H; or $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl, $C_4$-$C_7$ cycloalkylalkyl or $R^{12}$.

Embodiment 29. A compound of Embodiment 28 wherein each $R^{11}$ is H or $C_1$-$C_4$ alkyl.

Embodiment 30. A compound of Formula 1 wherein Q is —S(O)$_2$N($R^{21}$)$R^{22}$, —S(O)$_p$$R^{25}$ or —S(O)(—N$R^{28}$)$R^{29}$.

Embodiment 31. A compound of Formula 1 wherein Q is —S(O)$_2$N($R^{21}$)$R^{22}$.

Embodiment 32. A compound of Formula 1 wherein $R^{21}$ is H or $C_1$-$C_6$ alkyl.

Embodiment 33. A compound of Embodiment 32 wherein $R^{21}$ is H or methyl.

Embodiment 34. A compound of Formula 1 wherein $R^{22}$ is H; or $C_1$-$C_4$ alkyl, $C_2$-$C_4$ alkenyl, $C_2$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^{23}$.

Embodiment 35. A compound of Embodiment 34 wherein $R^{22}$ is $C_1$-$C_4$ alkyl optionally substituted with one or more substituents independently selected from $R^{23}$.

Embodiment 36. A compound of Formula 1 wherein each $R^{23}$ is independently halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, —CN or —NO$_2$; or a phenyl ring or a pyridinyl ring, each ring optionally substituted with one or more substituents independently selected from $R^{24}$.

Embodiment 37. A compound of Embodiment 36 wherein each $R^{23}$ is independently halogen, $C_1$-$C_4$ alkylthio, —CN, a phenyl ring or a pyridinyl ring.

Embodiment 38. A compound of Formula 1 wherein Q is —S(O)$_p$$R^{25}$.

Embodiment 39. A compound of Formula 1 wherein. $R^{25}$ is $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^{26}$.

Embodiment 40. A compound of Embodiment 39 wherein $R^{25}$ is $C_1$-$C_4$ alkyl optionally substituted with one or more substituents independently selected from $R^{26}$.

Embodiment 41. A compound of Embodiment 40 wherein $R^{25}$ is methyl, ethyl or $CH_2CF_3$.

Embodiment 42. A compound of Formula 1 wherein each $R^{26}$ is independently halogen, $C_1$-$C_4$ alkoxy, $C_1$-$C_4$ alkylthio, $C_1$-$C_4$ alkylsulfinyl, $C_1$-$C_4$ alkylsulfonyl, —CN or —NO$_2$.

Embodiment 43. A compound of Embodiment 42 wherein each $R^{26}$ is independently halogen or —CN.

Embodiment 44. A compound of Formula 1 wherein Q is —S(O)(=N$R^{28}$)$R^{29}$.

Embodiment 45. A compound of Formula 1 wherein $R^{28}$ is H, halogen, $C_1$-$C_4$ alkyl, —CN, —NO$_2$, $C_2$-$C_7$ haloalkylcarbonyl or $C_2$-$C_7$ alkoxycarbonyl.

Embodiment 46. A compound of Embodiment 45 wherein $R^{28}$ is H, $C_1$-$C_4$ alkyl, —CN or —NO$_2$.

Embodiment 47. A compound of Formula 1 wherein $R^{29}$ is $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^{26}$.

Embodiment 48. A compound of Embodiment 47 wherein $R^{29}$ is $C_1$-$C_4$ alkyl optionally substituted with one or more substituents independently selected from $R^{26}$.

Embodiment 49. A compound of Embodiment 48 wherein $R^{29}$ is methyl, ethyl or $CH_2CF_3$.

Embodiment 50. A compound of Formula 1 wherein W is O.

Embodiment 51. A compound of Formula 1 wherein n is 0.

Embodiment 52. A compound of Formula 1 wherein p is 1 or 2.

Embodiment 53. A compound of Formula 1 wherein $A^1$ and $A^2$ are $CR^3$; and $A^3$ is $CR^3$ or N.

Embodiment 54. A compound of Embodiment 53 wherein $A^3$ is $CR^3$.

Embodiment 55. A compound of Formula 1 wherein $A^1$ is N; and $A^2$ and $A^3$ are $CR^3$.

Embodiment 56. A compound of Formula 1 wherein $A^2$ is —N; and $A^1$ and $A^3$ are $CR^3$.

Embodiment 57. A compound of Formula 1 wherein $A^1$ is $CR^3$; and $A^2$ and $A^3$ are N.

Embodiment 58. A compound of Formula 1 wherein $A^2$ is $CR^3$; and $A^1$ and $A^3$ are N.

Embodiment 59. A compound of Formula 1 wherein $A^3$ is $CR^3$; and $A^1$ and $A^2$ are N.

Embodiment 60. A compound of Formula 1 wherein $B^1$, $B^2$ and $B^3$ are $CR^2$.

Embodiment 61. A compound of Embodiment 60 wherein $B^2$ is CH.

Embodiment 62. A compound of Formula 1 wherein $B^1$ is N; and $B^2$ and $B^3$ are $CR^2$.

Embodiment 63. A compound of Formula 1 wherein $B^2$ is N; and $B^1$ and $B^3$ are $CR^2$.

Embodiment 64. A compound of Formula 1 wherein $B^2$ is $CR^2$; and $B^1$ and $B^3$ are N.

Embodiment 65. A compound of Formula 1 wherein $R^{28}$ is other than halogen.

Embodiments of this invention, including Embodiments 1-65 above as well as any other embodiments described herein, can be combined in any manner, and the descriptions of variables in the embodiments pertain not only to the compounds of Formula 1 but also to the starting compounds and intermediate compounds. In addition, embodiments of this invention, including Embodiments 1-65 above as well as any other embodiments described herein, and any combination thereof, pertain to the compositions and methods of the present invention.

Combinations of Embodiments 1-65 can be illustrated by:

Embodiment A. A compound of Formula 1 wherein $A^1$ and $A^2$ are $CR^3$;

$A^3$ is $CR^3$ or N;

$B^1$, $B^2$ and $B^3$ are $CR^2$;

$R^1$ is $C_1$-$C_3$ alkyl optionally substituted with one or more substituents independently selected from $R^6$;

each $R^2$ is independently H, halogen, $C_1$-$C_6$ haloalkyl, $C_1$-$C_6$ haloalkoxy or —CN;

each $R^3$ is independently H, halogen, $C_1$-$C_6$ alkyl, $C_1$-$C_6$ haloalkyl, $C_2$-$C_6$ alkenyl, $C_3$-$C_6$ haloalkenyl, $C_2$-$C_6$ alkynyl, $C_3$-$C_6$ haloalkynyl, $C_3$-$C_6$ cycloalkyl, $C_1$-$C_6$ alkoxy, $C_1$-$C_6$ haloalkoxy, —N($R^4$)$R^5$, —C(W)N($R^4$)$R^5$, —CN or —NO$_2$;

each $R^4$ is independently H, $C_1$-$C_4$ alkyl, $C_2$-$C_4$ alkylcarbonyl or $C_2$-$C_4$ alkoxycarbonyl;

each $R^5$ is independently H; or $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^7$;

each $R^7$ is independently halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, —CN, —NO$_2$ or $Q^1$;

$Q^1$ is a phenyl ring, a pyridinyl ring, a thiazolyl ring, a pyrazolyl ring, a triazolyl ring or an imidazolyl ring, each ring optionally substituted with one or more substituents independently selected from halogen, $C_1$-$C_3$ alkyl, $C_1$-$C_3$ haloalkyl, —CN, —C(W)N($R^{10}$)$R^{11}$, C(O)O$R^{11}$ and $R^{12}$;

each $R^{10}$ is independently H, $C_1$-$C_4$ alkyl, $C_2$-$C_4$ alkylcarbonyl or $C_2$-$C_4$ alkoxycarbonyl; and each $R^{11}$ is independently H; or $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl, $C_4$-$C_7$ cycloalkylalkyl or $R^{12}$.

Embodiment B. A compound of Embodiment A wherein

Q is a phenyl ring, a pyridinyl ring, a pyrimidinyl ring, a triazinyl ring, a pyrazolyl ring, a triazolyl ring, a tetrazolyl ring, an imidazolyl ring, an oxazolyl ring, an isoxazolyl ring, a thiazolyl ring or an isothiazolyl ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —N($R^4$)$R^5$, —C(W)N($R^4$)$R^5$, C(O)O$R^5$ and $R^8$.

Embodiment C. A compound of Embodiment B wherein $R^1$ is $C_1$-$C_3$ alkyl optionally substituted with halogen;

each $R^2$ is independently H, halogen, $CF_3$, $OCF_3$ or —CN;

each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$;

each $R^4$ is H;

Q is a pyrazolyl ring, a triazolyl ring, a tetrazolyl ring or an imidazolyl ring, each ring attached through nitrogen and optionally substituted with one or more substituents independently selected from halogen, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, —CN, —$NO_2$, —N($R^4$)$R^5$, —C(W)N($R^4$)$R^5$, —C(O)O$R^5$ and $R^8$; and W is O.

Embodiment D. A compound of Embodiment C wherein $A^3$ is $CR^3$;

$B^2$ is CH;

$R^1$ is $CF_3$;

each $R^2$ is independently H or halogen;

each $R^3$ is independently H, halogen, $C_1$-$C_2$ alkyl, —C≡CH, —CN or —$NO_2$; and Q is a pyrazolyl ring, a triazolyl ring, a tetrazolyl ring or an imidazolyl ring, each ring attached through nitrogen and optionally substituted with one or more substituents independently selected from halogen, $C_1$-$C_4$ alkyl, $C_1$-$C_4$ haloalkyl, —CN and —$NH_2$.

Embodiment E. A compound of Embodiment A wherein

Q is —S(O)$_2$N($R^{21}$)$R^{22}$, —S(O)$_p R^{25}$ or —S(O)(—N$R^{28}$)$R^{29}$;

$R^{21}$ is H or $C_1$-$C_6$ alkyl;

$R^{22}$ is $C_1$-$C_4$ alkyl optionally substituted with one or more substituents independently selected from $R^{23}$;

each $R^{23}$ is independently halogen, $C_1$-$C_4$ alkylthio, —CN, a phenyl ring or a pyridinyl ring;

$R^{25}$ is $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally-substituted with one or more substituents independently selected from $R^{26}$;

each $R^{26}$ is independently halogen, $C_1$-$C_4$ alkoxy, $C_1$-$C_4$ alkylthio, $C_1$-$C_4$ alkylsulfinyl, $C_1$-$C_4$ alkylsulfonyl, —C or —$NO_2$;

$R^{28}$ is H, halogen, $C_1$-$C_4$ alkyl, —CN, —$NO_2$, $C_2$-$C_7$ haloalkylcarbonyl or $C_2$-$C_7$ alkoxycarbonyl; and $R^{29}$ is $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^{26}$.

Embodiment F. A compound of Embodiment E wherein $R^1$ is $C_1$-$C_3$ alkyl optionally substituted with halogen;

each $R^2$ is independently H, $CF_3$, $OCF_3$, halogen or —CN;

each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$;

each $R^4$ is H;

Q is —S(O)$_2$N($R^{21}$)$R^{22}$;

$R^{21}$ is H or methyl; and

W is O.

Embodiment G. A compound of Embodiment F wherein $A^3$ is $CR^3$;

$B^2$ is CH;

$R^1$ is $CF_3$;

each $R^2$ is independently H or halogen; and each $R^3$ is independently H, halogen, $C_1$-$C_2$ alkyl, —C≡CH, —CN or —$NO_2$.

Embodiment H. A compound of Embodiment E wherein $R^1$ is $C_1$-$C_3$ alkyl optionally substituted with halogen;

each $R^2$ is independently H, $CF_3$, $OCF_3$, halogen or —CN;

each $R^3$ is independently H, halogen, $C_1$-$C_4$ alkyl; $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$;

each $R^4$ is H;

Q is —S(O)$_p R^{25}$;

$R^{25}$ is $C_1$-$C_4$ alkyl optionally substituted with one or more substituents independently selected from $R^{26}$;

each $R^{26}$ is independently halogen or —CN;

W is O; and p is 1 or 2.

Embodiment I. A compound of Embodiment H wherein $A^3$ is $CR^3$;

$B^2$ is CH;

$R^1$ is $CF_3$;

each $R^2$ is independently H or halogen; and each $R^3$ is independently H, halogen, $C_1$-$C_2$ alkyl, —C≡CH, —CN or —$NO_2$.

Embodiment J. A compound of Embodiment E wherein $R^1$ is $C_1$-$C_3$ alkyl optionally substituted with halogen;

each $R^2$ is independently H, $CF_3$, $OCF_3$, halogen or —CN;

each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$;

each $R^4$ is H;

Q is —S(O)(—N$R^{28}$)$R^{29}$;

$R^{28}$ is H, $C_1$-$C_4$ alkyl, —CN or —$NO_2$;

$R^{29}$ is $C_1$-$C_4$ alkyl optionally substituted with one or more substituents independently selected from $R^{26}$;

each $R^{26}$ is independently halogen or —CN; and

W is O.

Embodiment K. A compound of Embodiment J wherein $A^3$ is $CR^3$;

$B^2$ is CH;

$R^1$ is $CF_3$;

each $R^2$ is independently H or halogen; and each $R^3$ is independently H, halogen, $C_1$-$C_2$ alkyl, —C≡CH, —CN or —$NO_2$.

Specific embodiments include compounds of Formula 1 selected from the group consisting of:

5-(3,5-dichlorophenyl)-4,5-dihydro-3-[4-(1H-pyrazol-1-yl) phenyl]-5-(trifluoromethyl)-isoxazole;
5-(3,5-dichlorophenyl)-4,5-dihydro-3-[3-methyl-4-(1H-pyrazol-1-yl)phenyl]-5-(trifluoromethyl)isoxazole;
2-[4-[5-(3,5-dichlorophenyl)-4,5-dihydro-5-(trifluoromethyl)-3-isoxazolyl]phenyl]-pyridine;
5-(3,5-dichlorophenyl)-4,5-dihydro-3-[4-(1H-imidazol-1-yl)phenyl]-5-(trifluoromethyl)isoxazole;
1-[4-[5-(3,5-dichlorophenyl)-4,5-dihydro-5-(trifluoromethyl)-3-isoxazolyl]phenyl]-1H-1,2,4-triazole;
1-[4-[5-(3,5-dichlorophenyl)-4,5-dihydro-5-(trifluoromethyl)-3-isoxazolyl]-2-methyl-phenyl]-1H-1,2,4-triazole;
1-[4-[5-(3,5-dichlorophenyl)-4,5-dihydro-5-(trifluoromethyl)-3-isoxazolyl]-2-methyl-phenyl]-1H-1,2,3-triazole;
5-[5-(3,5-dichlorophenyl)-4,5-dihydro-5-(trifluoromethyl)-3-isoxazolyl]-2-(1H-1,2,4-triazol-1-yl)benzonitrile;
5-[5-(3,5-dichlorophenyl)-4,5-dihydro-5-(trifluoromethyl)-3-isoxazolyl]-2-(1H-1,2,3-triazol-1-yl)benzenecarbothioamide;
2-(3-amino-1H-1,2,4-triazol-1-yl)-5-[5-(3,5-dichlorophenyl)-4,5-dihydro-5-(trifluoromethyl)-3-isoxazolyl]benzonitrile;
5-[5-(3,5-dichlorophenyl)-4,5-dihydro-5-(trifluoromethyl)-3-isoxazolyl]-2-(1H-tetrazol-1-yl)benzonitrile;
N-(cyclopropylmethyl)-4-[5-(3,5-dichlorophenyl)-4,5-dihydro-5-(trifluoromethyl)-3-isoxazolyl]-2-methylbenzenesulfonamide;
4-[5-(3,5-dichlorophenyl)-4,5-dihydro-5-(trifluoromethyl)-3-isoxazolyl]-2-methyl-N-(2-pyridinylmethyl)benzenesulfonamide;
5-[5-(3,5-dibromophenyl)-4,5-dihydro-5-(trifluoromethyl)-3-isoxazolyl]-2-(1H-1,2,4-triazol-1-yl)benzonitrile;
5-[5-(3,5-dichlorophenyl)-4,5-dihydro-3-[4-(methylsulfonyl)phenyl]-5-(trifluoromethyl)isoxazole;
5-[(3,5-dichlorophenyl)-4,5-dihydro-5-(trifluoromethyl)-3-isoxazolyl]-2-methylsulfonyl)benzonitrile; and
3-[3-bromo-4-(methylthio)phenyl]-5-(3,5-dichlorophenyl)-4,5-dihydro-5-(trifluoromethyl)isoxazole.

Further specific embodiments include any combination of the compounds of Formula 1 selected from the group immediately above.

Embodiments of the present invention further include:

Embodiment A1. A compound of Formula 1q, an N-oxide, or a salt thereof,

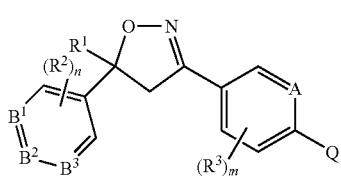

1q wherein:
A is selected from the group consisting of $CR^3$ and N;
$B^1$, $B^2$ and $B^3$ are independently selected from the group consisting of $CR^2$ and N;
$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$-alkylcycloalkyl or $C_4$-$C_7$ cycloalkylalkyl, each optionally substituted with one or more substituents independently selected from $R^6$;
each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_2$-$C_6$ alkenyl, $C_3$-$C_6$ haloalkenyl, $C_2$-$C_6$ alkynyl; $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —N($R^4$)$R^5$, —C(W)N($R^4$)$R^5$, —C(W)O$R^5$, —CN or —NO$_2$;

Q is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N($R^4$)$R^5$, —C(W)N($R^4$)$R^5$, —C(O)O$R^5$ and —$R^8$; or —S(O)$_2$N$R^{21}$)$R^{22}$, —S(O)$_p$$R^{25}$ or —S(O)(=N$R^{28}$)$R^{29}$;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;

each $R^7$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN, —NO$_2$ or $Q^1$;

each $R^8$ is independently a phenyl ring or a pyridinyl ring; each ring optionally substituted with one or more substituents independently selected from $R^9$;

each $R^9$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —COOH, —CN or —NO$_2$;

each $Q^1$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl; $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, —C(W)N($R^{10}$)$R^{11}$, —C(O)O$R^{11}$ and $R^{12}$;

each $R^{10}$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{11}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or $R^{12}$;

each $R^{12}$ is independently a phenyl ring or a pyridinyl ring, each ring optionally substituted with one or more substituents independently selected from $R^{13}$;

each $R^{13}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OX, —NH$_2$, —COOH, —CN or —NO$_2$;

$R^{21}$ is H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{22}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{23}$;

each $R^{23}$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$; or a phenyl ring or a pyridinyl ring, each ring optionally substituted with one or more substituents independently selected from $R^{24}$;

each $R^{24}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —COOH, —CN or —NO$_2$;

$R^{25}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{26}$;

each $R^{26}$ is independently halo-en, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylcarbonyl, $C_2$-$C_7$ alkoxycarbonyl, —CN or —NO$_2$; or a phenyl ring or a pyridinyl ring, each ring optionally substituted with one or more substituents independently selected from $R^{27}$;

each $R^{27}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —O, —NH$_2$, —COOH, —CN or —NO$_2$;

$R^{28}$ is H, —CN, —NO$_2$, $C_2$-$C_7$ alkylcarbonyl, $C_2$-$C_7$ haloalkylcarbonyl, $C_2$-$C_7$ alkoxycarbonyl, $C_2$-$C_7$ alkylaminocarbonyl, $C_3$-$C_7$ dialkylaminocarbonyl, $C_1$-$C_6$ alkylsulfonyl or $C_1$-$C_6$ haloalkylsulfonyl; or $R^{28}$ is $C_1$-$C_6$ alkyl, $C_3$-$C_6$ cycloalkyl, ($C_1$-$C_6$ alkoxy)-($C_1$-$C_6$ alkyl) or $C_1$-$C_6$ alkylthio, each optionally substituted with halogen, $C_1$-$C_6$ alkyl, $C_1$-$C_6$ haloalkyl, $C_1$-$C_6$ cycloalkyl, $C_1$-$C_6$ halocycloalkyl, $C_1$-$C_6$ alkoxy, $C_1$-$C_6$ haloalkoxy; —CN or —NO$_2$;

$R^{29}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{26}$;

each W is independently O or S;

p is 0, 1 or 2;

m is 1, 2 or 3; and n is 1 or 2.

Embodiment AA. A compound of Formula 1p, an N-oxide, or a salt thereof,

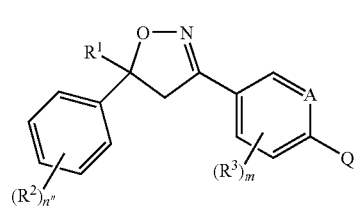

1p wherein:

A is selected from the group consisting of CR$^3$ and N;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;

Q is a phenyl ring or a 5- or 6-membered saturated or unsaturated heterocyclic ring, each ring optionally substituted with one or more substituents independently selected from the group halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, C(N(R$^4$)R$^5$, C(O)OR$^5$ and R$^8$;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, each optionally substituted with one or more substituents independently selected from $R^7$;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;

each $R^7$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$; or Q$^1$;

each $R^8$ is independently a phenyl ring or a pyridinyl ring, each ring optionally substituted with one or more substituents independently selected from $R^9$;

each $R^9$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $Q^1$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, CN, $NO_2$, $C(W)N(R^{10})R^{11}$, $C(O)OR^{11}$ or $R^{12}$;

each $R^{10}$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{11}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or $R^{12}$;

each $R^{12}$ is independently a phenyl ring or a pyridinyl ring, each ring optionally substituted with one or more substituents independently selected from $R^9$;

each W is independently O or S;

m is 1, 2 or 3; and n" is 1, 2, 3, 4 or 5.

Embodiment BB. A compound of Embodiment AA wherein

Q is a phenyl ring or a 5- or 6-membered saturated or unsaturated heterocyclic ring, each ring optionally substituted with one or more substituents independently selected from the group halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, CN, $NO_2$, $C(W)N(R^4)R^5$, $C(O)OR^5$ and $R^8$; provided that when Q is a 5-membered nitrogen-containing heterocyclic ring Q is attached through nitrogen.

Embodiment CC. A compound of Embodiment BB wherein $R^1$ is $C_1$-$C_3$ alkyl optionally substituted with one or more substituents selected from $R^6$;

each $R^2$ is independently selected from the group consisting of H, halogen, $C_1$-$C_6$ haloalkyl, $C_1$-$C_6$ haloalkoxy and CN;

each $R^3$ is independently selected from the group consisting of H, halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, CN and $NO_2$;

Q is a phenyl ring, a pyridinyl ring, a pyrimidinyl ring, a triazinyl ring, a pyrazolyl ring, a triazolyl ring, an imidazolyl ring, an oxazolyl ring, an isoxazolyl ring, a thiazolyl ring or an isothiazolyl ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsufinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, CN, $NO_2$, $C(W)N(R^4)R^5$, $C(O)OR^5$ and $R^8$;

each $R^4$ is independently H, $C_1$-$C_6$ alkyl, $C_2$-$C_7$ alkylcarbonyl or $C_2$-$C_7$ alkoxycarbonyl;

each $R^5$ is independently H; or $C_1$-$C_4$ alkyl, $C_2$-$C_4$ alkenyl, $C_2$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents selected from $R^7$;

each $R^7$ is independently selected from group consisting of halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, —CN and —$NO_2$; or $Q^1$; and $Q^1$ is a phenyl ring, a pyridinyl ring, a thiazolyl ring, a pyrazolyl ring, a triazolyl ring or an imidazolyl ring, each ring optionally substituted with one or more substituents independently selected from halogen, $C_1$-$C_3$ alkyl, $C_1$-$C_3$ haloalkyl, CN, $C(O)N(R^{10})R^{11}$, $C(O)OR^{11}$ and $R^{12}$.

Embodiment DD. A compound of Embodiment CC wherein $R^1$ is $C_1$-$C_3$ alkyl optionally substituted with halogen;

each $R^2$ is independently selected from the group consisting of H, $CF_3$, $OCF_3$, halogen and CN;

each $R^3$ is independently selected from group consisting of H, halogen, $C_1$-$C_4$ alkyl, $C_1$-$C_4$ haloalkyl, cyclopropyl, $C_1$-$C_4$ alkoxy, CN and $NO_2$;

Q is a pyrazolyl ring, a triazolyl ring or an imidazolyl ring, each ring attached through nitrogen and optionally substituted with one or more substituents independently selected from halogen, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, $C_1$-$C_4$ alkylamino, $C_2$-$C_4$ dialkylamino, CN, $NO_2$, $C(W)N(R^4)R^5$, $C(O)OR^5$ and $R^8$;

$R^4$ is H; and

W is O.

Embodiment BE. A compound of Embodiment DD wherein $R^1$ is $CF_3$; and n" is 1 or 2.

Specific embodiments include compounds of Formula lip selected from the group, consisting of:

5-(3,5-dichlorophenyl)-4,5-dihydro-3-[4-(1H-pyrazol-1-yl)phenyl]-5-(trifluoromethyl)isoxazole;

5-(3,5-dichlorophenyl)-4,5-dihydro-3-[3-methyl-4-(1H-pyrazol-1-yl)phenyl]-5-(trifluoromethyl)isoxazole;

2-[4-[5-(3,5-dichlorophenyl)-4,5-dihydro-5-(trifluoromethyl)-3-isoxazolyl]phenyl]pyridine;

5-(3,5-dichlorophenyl)-4,5-dihydro-3-[4-(1H-imidazol-1-yl)phenyl]-5-(trifluoromethyl)isoxazole; and 1-[4-[5-(3,5-dichlorophenyl)-4,5-dihydro-5-(trifluoromethyl)-3-isoxazolyl]phenyl]-1H-1,2,4-triazole.

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a biologically effective amount of a compound of any of the preceding Embodiments, as well as any other embodiments described herein, and any combinations thereof, and at least one additional component selected from the group consisting of a surfactant, a solid diluent and a liquid diluent, said composition optionally further comprising a biologically effective amount of at least one additional biologically active compound or agent Embodiments of the invention further include methods for controlling an invertebrate pest comprising contacting the invertebrate pest or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a biologically effective amount of a compound of any of the preceding Embodiments and a propellant. Embodiments of the invention further include a bait composition for controlling an invertebrate pest comprising a biologically effective amount of a compound of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include a method for protecting a seed from an invertebrate pest comprising contacting the seed with a biologically effective amount of a compound any of the preceding Embodiments. Embodiments of the invention further include a treated seed comprising a compound of any of the preceding Embodiments in an amount of from about 0.0001 to 1% by weight of the seed before treatment.

Embodiments of the invention also include a composition for protecting an animal from an invertebrate parasitic pest comprising a parasiticidally effective amount of a compound of any of the preceding Embodiments and at least one carrier. Embodiments of the invention also include a composition comprising a compound of any of the preceding Embodiments in a form for oral administration. Embodiments of the invention further include a method for protecting an animal from an invertebrate parasitic pest comprising administering to the animal a parasiticidally effective amount of a compound of any of the preceding Embodiments.

Compounds of Formula 1 can be prepared by one or more of the following methods and variations as described in Schemes 1-8. The definitions of $R^1$, $R^2$, $R^3$, $R^{25}$, $A^1$, $A^2$, $A^3$, $B^1$, $B^2$, $B^3$, n, p and Q in the compounds of Formulae 1-10 below are as defined above for Formula 1 in the Summary of the Invention. Compounds of Formulae 1a and 1b are subsets of compounds of Formula 1. Compounds of Formula 2a are a subset of compounds of Formula 2.

Compounds of Formula 1 can be prepared by the cycloaddition of compounds of Formula 2 with nitrile oxides derived from oximes of Formula 3 as outlined in Scheme 1. The reaction typically proceeds through the intermediacy of an in situ generated hydroxamyl chloride. In a typical procedure a chlorinating reagent such as sodium hypochlorite, N-chlorosuccinimide, or chloramine-T is combined with the oxime in the presence of the styrene. Depending on the conditions amine bases such as pyridine or triethylamine may be necessary. The reaction can be run in a wide variety of solvents including tetrahydrofuran, diethyl ether, methylene chloride, dioxane, and toluene with optimum temperatures ranging from room temperature to the reflux temperature of the solvent. Example 1, Step B illustrates a typical procedure for this reaction. General procedures for cycloaddition of nitrile oxides with olefins are well documented in the chemical literature. For relevant references see Lee, *Synthesis*, 1982, 6, 508-509 and Kanemasa et al., *Tetrahedron*, 2000, 56, 1057-1064 as well as references cited within.

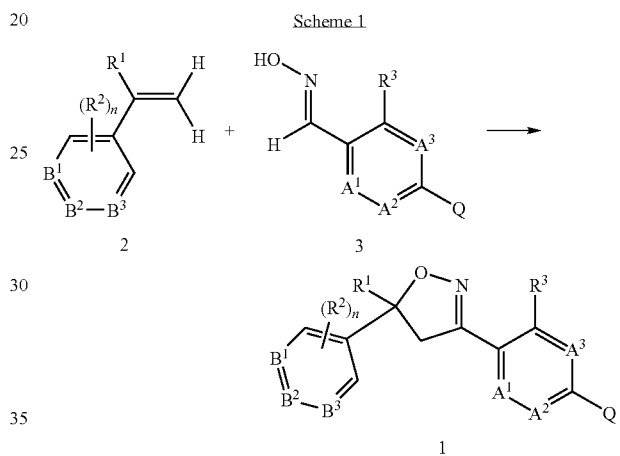

Scheme 1

Compounds of Formula 1, wherein Q is a 5-membered N-linked heterocyclic ring can also be prepared by direct displacement of an aromatic halide of Formula 4 wherein Y is Br or F with an azole heterocyclic ring of Formula d as shown in Scheme 2. Typical azole heterocyclic rings of Formula 5 include optionally substituted pyrazoles, imidazoles, triazoles and tetrazoles. Bromides can be displaced with the use of copper iodide and a palladium catalyst, see for example Kanemasa et al., *European Journal of Organic Chemistry*, 2004, 695-709. For direct fluorine displacement the reaction is typically run in a polar aprotic solvent such as N,N-dimethylformamide or N,N-dimethylacetamide and in the presence of an inorganic base such as sodium or potassium carbonate. Example 2, Step C illustrates a typical procedure for this type of reaction

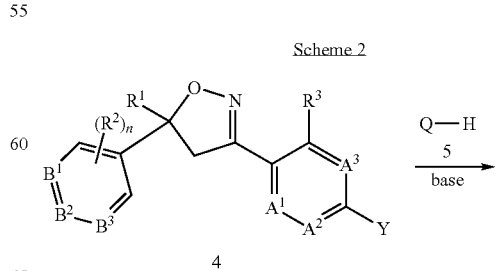

Scheme 2 wherein Y is Br or F.

-continued

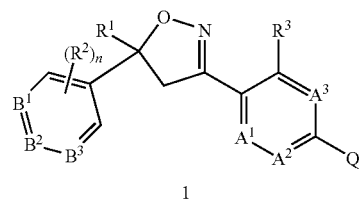

wherein Q is a 5-membered N-linked heterocyclic ring.

An alternate preparation for the compounds of Formula 1 wherein Q is a phenyl or aromatic heterocyclic ring includes the well known Suzuki reaction via Pd-catalyzed cross coupling of an aromatic iodide or bromide of Formula 4 wherein Y is Br or I with an aryl or heteroaryl boronic acid of Formula 6 (Scheme 3). Many catalysts are useful for this type of transformation; a typical catalyst is tetrakis(triphenylphosphine)palladium(0). Solvents such as tetrahydrofuran, acetonitrile, diethyl ether and dioxane are suitable. The boronic acids of Formula 6 are either commercially available or can be prepared by known methods. Other methods including the Heck, Stifle, Kumada and Buchwald-Hartwig coupling procedures offer many alternatives for introduction of Q heterocyclic groups. For leading references see for example Zificsak, Craig A and Hlasta, Dennis J., *Tetrahedron*, 2004, 60, 8991-9016. For a thorough review of palladium chemistry applicable to the synthesis of heterocyclic Q groups see Li, J. J.; Gribble, G. W.; Editors. *Palladium in Heterocyclic Chemistry: A Guide for the Synthetic Chemist*, Elsevier: Oxford, M 2000.

Scheme 3

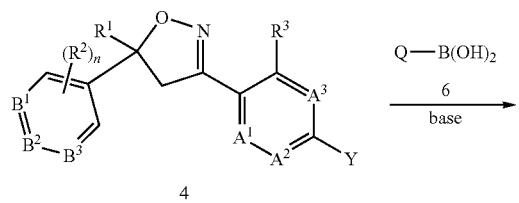

wherein Y is Br or I.

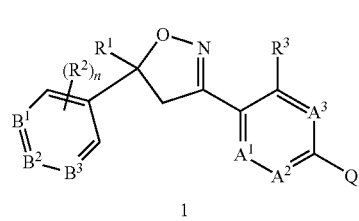

wherein Q is phenyl or aromatic heterocyclic ring

The oximes of Formula 3 are available by contacting the corresponding aldehydes of Formula 7 with hydroxylamine according to known methods as shown in Scheme 4. The aldehydes can be prepared by known synthetic procedures, and many are known compounds, some being commercially available.

Scheme 4

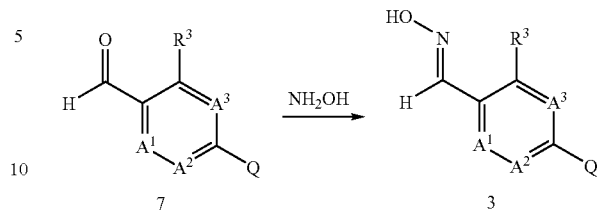

A wide variety of alternate methods exist for the preparation of heterocyclic Q groups found in Formula 1. These can be prepared from well documented functional group transformations of ketones, esters, acids, aldehydes, nitrites and the lice. For leading references see Tanaka et al., *J. Med Chem*, 1998, 41, 2390-2410 and references cited within.

An especially useful group of styrenes for the synthesis of compounds of Formula 1 are represented by Formula 2a as shown in Scheme 5. These intermediates can be prepared by the palladium-catalyzed coupling of commercially available 2-bromo-3,3,3-trifluoropropene (Formula 8) with aryl boronic acids of Formula 9. General procedures for this reaction are documented in the chemical literature, see Pan et al., *J. Fluorine Chemistry*, 1999, 95, 167-170. A typical procedure using modified conditions is described in Example 1, Step A.

Scheme 5

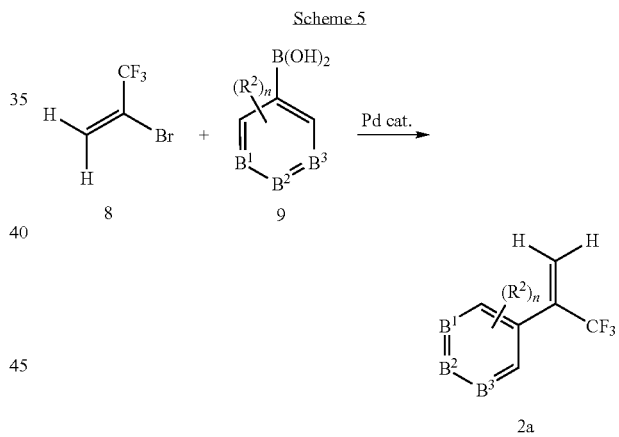

Compounds of Formula 1, wherein Q is $S(O)_2NR^{21}R^{22}$ can be prepared in three steps by direct displacement of an aromatic halide of Formula 4 wherein Y is Cl, Br or F with a mercaptan such as benzylmercaptan, followed by oxidation to the sulfonyl chloride and subsequent conversion to the sulfonamide by reaction with an amine (Scheme 6). Typical displacement reactions involve treatment of the aromatic halide of Formula 4 with the mercaptan in a polar aprotic solvent such as such as N,N-dimethylformamide or N,N-dimethylacetamide and in the presence of an inorganic base such as sodium, potassium or cesium carbonate. Oxidation of the benzylthioether intermediate to the corresponding sulfonyl chloride is readily accomplished with 5% sodium hypochlorite (commercial bleach) in solvents such as methylene chloride or chloroform. Conversion to the sulfonamide is accomplished by known literature procedures involving treatment of the sulfonyl chloride with a amine ($HNR^{21}R^{22}$) in the presence of an acid scavenger such as pyridine, triethylamine or other amine bases. In certain instances it may be convenient to use excess amine as both the nucleophile and acid scavenger. Example 4 illustrates a typical procedure for preparing compounds of Formula 1 wherein Q is $S(O)_2NR^{21}R^{22}$.

2 is readily accomplished by reaction with sodium metaperiodate or Oxone® (potassium peroxymonosulfate) in solvents such as water or alcohols, or 3-chloroperoxybenzoic acid (MCPBA) in solvents such as methylene chloride or chloroform.

Scheme 7

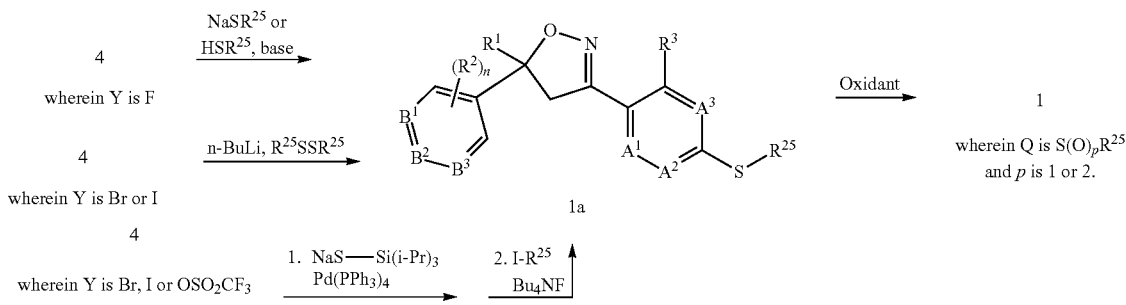

Scheme 6

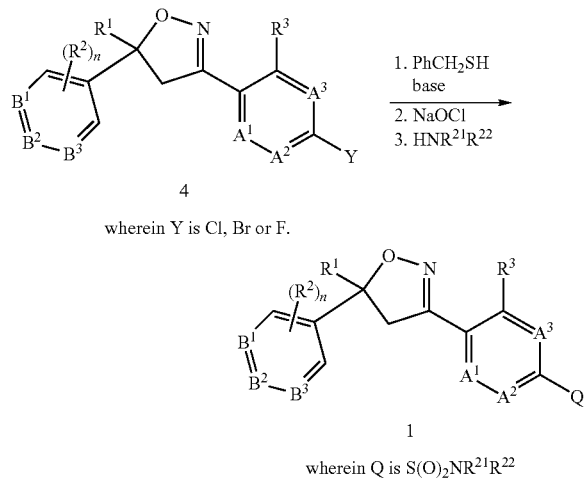

Compounds of Formula 1a (i.e. Formula 1 wherein Q is $S(O)_pR^{25}$ and p is 0) can be prepared by direct displacement of an aromatic halide of Formula 4 wherein Y is Cl, Br or F with a mercaptan or its alkali metal salt, such as methylmercaptan or sodium thiomethoxide. Oxidation of the thioether group of Formula 1a to the sulfinyl or sulfonyl group (i.e. Formula 1 wherein Q is $S(O)_pR^{25}$ and p is 1 or 2) can be accomplished by methods very familiar to one skilled in the art (Scheme 7). Typical displacement reaction involves treatment of the aromatic halide of Formula 4 with the mercaptan in a polar aprotic solvent such as N,N-dimethylformamide or N,N-dimethylacetamide and in the presence of an inorganic base such as sodium, potassium or cesium carbonate, or by use of a salt of the mercaptan (as shown in Scheme 7). The mercaptan salt is either commercially available or can be prepared separately by treatment of the mercaptan with a strong base such as sodium hydride. Oxidation of the thioether compounds of Formula 1a to the sulfinyl or sulfonyl compounds of Formula 1 wherein Q is $S(O)_pR^{25}$ and p is 1 or 2 is readily accomplished by reaction with sodium metaperiodate or Oxone® (potassium peroxymonosulfate) in solvents such as water or alcohols, or 3-chloroperoxybenzoic acid (MCPBA) in solvents such as methylene chloride or chloroform.

Alternatively, compounds of Formula 1a can be prepared by metal-halogen exchange of an aromatic halide of Formula 4 wherein Y is Br or I with n-BuLi, followed by reaction with a sulfur-containing reagent (e.g., ethyl disulfide or methyl methanethiolsulfonate). Compounds of Formula 1a can also be prepared by transition metal-catalyzed reaction of an aromatic halide or trifluoromethanesulfonate of Formula 4 wherein Y is Br, I or $OSO_2CF_3$ with a mercaptan salt such as triisopropylsilylmercaptan sodium salt, or sodium sulfonate, followed by alkylating with a halide such as $I-R^{25}$ in the presence of a phase transfer catalyst such as tetrabutylammonium fluoride. Example 5 illustrates typical procedure for preparing compounds of Formula 1 wherein Q is $S(O)_pR^{25}$ and p is 0. Examples 6 and 7 illustrate typical procedures for preparing compounds of Formula 1 wherein Q is $S(O)_pR^{25}$ and p is 2.

Compounds of Formula 1b (i.e. Formula 1 wherein Q is $S(O)_pR^{25}$ and p is 2) can be prepared by treatment of a sulfonyl chloride of Formula 10 with reducing reagents as sodium sulfite ($Na_2SO_3$), followed by treatment of the resulting sulfonate salt with an alkylating agent and base to afford the sulfone of Formula 1b.

Scheme 8

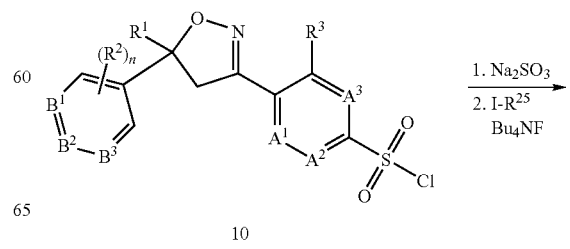

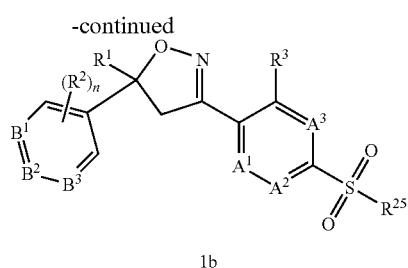

1b

Sulfonyl chlorides of Formula 10 can be prepared by the reactions illustrated in Scheme 6 involving direct displacement of an aryl halide of Formula 4 with a mercaptan such as benzylmercaptan followed by oxidation to the sulfonyl chloride.

Compounds of Formula 4 can be prepared analogously by the methods described for compounds of Formula 1 in Scheme 1.

It is recognized that some reagents and reaction conditions described above for preparing compounds of Formula 1 may not be compatible with certain functionalities present in the intermediates. In these instances, the incorporation of protection/deprotection sequences or functional; group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents Without further elaboration, it is believed that one skilled in the art using the preceding description can utilize the present invention to its fullest extent. The following Examples are, therefore, to be construed as merely illustrative, and not limiting of the disclosure in any way whatsoever. $^1$H NMR spectra are reported in ppm downfield from tetramethylsilane; "s" means singlet, "d" means doublet, "t" means triplet, "q" means quartet, "AB q" means AB quartet, "m" means multiplet, "dd" means doublet of doublets, "dt" means doublet of triplets, "br s" means broad singlet and "br t" means broad triplet.

Example 1

Preparation of 5-(3,5-dichlorophenyl)-4,5-dihydro-3-[4-(1H-pyrazol-1-yl)phenyl]-5-(trifluoromethyl)isoxazole Step A: Preparation of 1,3-dichloro-5-[1-(trifluoromethyl)ethenyl]benzene To a mixture of tetrahydrofuran (33 mL), ethylene glycol dimethyl ether (33 mL), and 4 N aqueous potassium hydroxide (33 mL) in a 200 mL Fisher-Porter sealed tube was added 3,5-dichlorophenylboronic acid (8.72 g, 45.7 mmol) and 2-bromo-3,3,3-trifluoro-propene (10.0 g, 57.2 mmol), followed by the addition of tetrakis(triphenylphosphine)-palladium(0) (264 mg, 0.229 mmol). The mixture was heated to 75° C. for 3 h. Then the reaction mixture was partitioned between diethyl ether and water. The aqueous extract was washed with diethyl ether (2×20 mL). The organic extracts were combined, dried (MgSO$_4$), and concentrated under reduced pressure to provide a residue. The residue was purified by silica gel chromatography and eluted with hexane to afford 4.421 g of the title compound as a clear oil.

$^1$H NMR (CDCl$_3$) δ 7.41 (s, 2H), 7.33 (s, 1H), 6.04 (d, 1H), 5.82 (d, 1H).

Step B: Preparation of 5-(3,5-dichlorophenyl)-4,5-dihydro-3-[4-(1H-pyrazol-1-yl)-phenyl]-5-(trifluoromethyl)isoxazole To a solution of 4-(1H-pyrazol-1-yl)benzaldehyde (1.0 g, 5.81 mmol) in ethanol (50 mL) was added 50% by wt. hydroxylamine aqueous solution (1.0 mL, 15.2 mmol). The reaction mixture was stirred at room temperature for 3 h. The mixture was concentrated under reduced pressure to give a waxy oil, which was purified by silica gel chromatography to afford the [C(E)]-4-(1H-pyrazol-1-yl)benzaldehyde oxime as a white solid (923 mg). Then to a solution of the [C(E)]-4-(1H-pyrazol-1-yl)benzaldehyde oxime (923 mg, 4.94 mmol) and 1,3-dichloro-5-(1-trifluoromethyl)ethenyl]benzene (i.e. the product from Example 1, Step A) (1.31 g, 5.44 mmol) in tetrahydrofuran (25 mL) was added aqueous sodium hypochlorite solution (25 mL). After stirring overnight at room temperature, the reaction mixture was partitioned between ethyl acetate and water, and the aqueous extract was extracted further with ethyl acetate two times. The organic extracts were combined, dried (MgSO$_4$) and concentrated, and the residual solid was purified by silica gel chromatography and eluted with a gradient of 0-50% ethyl acetate in hexane to afford the title product, a compound of the present invention, as a white solid (617 mg), m.p. 174-175° C.

$^1$H NMR (DMSO-d$_6$) δ 8.63 (d, 1H), 8.00 (d, 2H), 7.84 (m, 4H), 7.64 (d, 2H), 6.60 (m, 1H), 4.38 (AB q, 2H).

Example 2

Preparation of 5-(3,5-dichlorophenyl)-4,5-dihydro-3-[3-methyl (1H-pyrazol-1-yl)phenyl]-5-(trifluoromethyl)isoxazole Step A: Preparation of [C(E)]-4-fluoro-3-methylbenzaldehyde oxime To a solution of 4-fluoro-3-methylbenzaldehyde (5.0 g, 36.2 mmol) in ethanol (100 mL) was added 50% by wt hydroxylamine aqueous solution (5.0 mL, 76.0 mmol). The reaction mixture was stirred at room temperature for 3 h. Then the mixture was concentrated under reduced pressure to give a waxy oil, which was purified by silica gel chromatography and eluted with a gradient of 0-25% ethyl acetate in hexane to afford the title compound as a white solid (4.971 g), m.p. 79-80° C.

$^1$H NMR (CDCl$_3$) δ 8.08 (s, 1H), 7.51 (br s, 1H), 7.43 (d, 1H), 7.36 (m, 1H), 7.01 (t, 1H), 2.29 (s, 3H).

Step B: Preparation of 5-(3,5-dichlorophenyl)-3-(4-fluoro-3-methylphenyl)-4,5-dihydro-5-(trifluoromethyl)isoxazole To a solution of [C(E)]-4-fluoro-3-methylbenzaldehyde oxime (i.e. the product of Step A) (4.971 g, 32.5 mmol), 1,3-dichloro-5-(1-trifluoromethyl)ethenyl]benzene (i.e. the product from Example 1, Step A) (8.684 g, 35.7 mmol); and tetrahydrofuran (200 mL) was added sodium hypochlorite aqueous solution (200 mL). After stirring 1 h at room temperature, the reaction mixture was partitioned between ethyl acetate and water, the aqueous extract was extracted further with ethyl acetate two times. The organic extracts were combined, dried ($MgSO_4$), concentrated, and the residual solid was purified by silica gel chromatography and eluted with a gradient of 0-25% ethyl acetate in hexane to afford the title compound as a yellow waxy oil (10.515 g).

$^1$H NMR ($CDCl_3$) δ 7.52 (m, 3H), 7.45 (m, 1H), 7.41 (t, 1H), 7.05 (t, 1H), 4.07 (d, 1H), 3.68 (d, 1H), 2.29 (s, 3H).

Step C: Preparation of 5-(3,5-dichlorophenyl)-4,5-dihydro-3-[3-methyl-4-(1H-pyrazol-1-yl)phenyl]-5-(trifluoromethyl)isoxazole To a mixture of potassium carbonate (1.0 g, 7.24 mmol) and pyrazole (0.50 g, 7.35 mmol) in N,N-dimethylformamide (5 mL) was added 5-(3,5-dichlorophenyl)-3-(4-fluoro-3-methylphenyl)-4,5-dihydro-5-(trifluoromethyl)isoxazole (i.e. the product from Step B) (0.50 g, 1.27 mmol). The reaction mixture was stirred vigorously for 36 h at 120° C. Then the reaction mixture was absorbed onto silica gel, concentrated, and purified by flash chromatography on silica gel and eluted with a gradient of 0-25% ethyl acetate in hexane to afford the title product, a compound of the present invention, as a yellow oil (32.0 mg).

$^1$H NMR ($CDCl_3$) δ 7.75 (d, 1H), 7.64 (d, 2H), 7.58 (dd, 1H), 7.52 (d, 2H), 7.43 (m, 2H), 6.48 (t, 1H), 4.11 (d, 1H), 3.73 (d, 1H), 2.34 (s, 3H).

Example 3

Preparation of 2-[4-[5-(3,5-dichlorophenyl)-4,5-dihydro-5-(trifluoromethyl)-3-isoxazolyl]phenyl]pyridine Step A: Preparation of [C(E)]-4-(2-pyridinyl)benzaldehyde oxime A solution of 4-(pyridine-2-yl)benzaldehyde (1.83 g, 0.01 mol), hydroxylamine hydrochloride (0.7 g, 0.01 mol), and sodium acetate (0.33 g) in ethanol (17 mL) and water (1 mL) was heated at reflux for 5 h. The reaction mixture was cooled to room temperature, and the resulting precipitate was collected, rinsed with ethanol, and dried under reduced pressure to afford 1.5 g of the title compound as a white solid.

$^1$H NMR ($CDCl_3$) δ 11.8 (br s, 1H), 8.8 (s, 1H), 8.4 (m, 3H), 8.3 (m, 1H), 7.8 (m, 3H), 7.7 (m, 1H).

Step B: Preparation of 2-[4-[5-(3,5-dichlorophenyl)-4,5-dihydro-5-(trifluoromethyl)-3-isoxazolyl]-phenyl]pyridine To a solution of [C(E)]-4-(2-pyridinyl)benzaldehyde oxime (i.e. the product from Step A) (0.2 g, 0.001 mol) and 1,3-dichloro-5-[1-(trifluoromethyl)ethenyl]benzene (i.e. the product from Example 1, Step A) (0.25 g, 0.001 mol) in dichloromethane (20 mL) at 5° C. was added an aqueous solution of sodium hypochlorite (6.15%—Clorox® brand) (5.5 mL) and triethylamine (6 drops). The mixture was stirred at room temperature for 0.5 h, diluted with water (30 mL), and extracted with dichloromethane (2×20 mL). The organic extracts were dried ($MgSO_4$) and concentrated under reduced pressure to provide a solid residue. The residue was purified by silica gel column chromatography to afford 0.375 g of the title product, a compound of the present invention, as a white solid.

$^1$H NMR ($CDCl_3$) δ 8.8 (m, 1H), 8.05 (m, 2H), 7.8 (m, 3H), 7.76 (d, 2H), 7.2 (d, 2H), 4.2 (d, 1H), 3.8 (d, 1H).

Example 4

Preparation of 4-[5-(3,5-dichlorophenyl)-4,5-dihydro-5-(trifluoromethyl)-3-isoxazolyl]-2-methyl-N-(2-pyridinylmethyl)benzenesulfonamide Step A: Preparation of 5-(3,5-dichlorophenyl)-4,5-dihydro-3-[3-methyl-4-[(phenylmethyl)thio]phenyl]-5-(trifluoromethyl)isoxazole To a solution of 5-(3,5-dichlorophenyl)-3-(4-fluoro-3-methylphenyl)-4,5-dihydro-5-(trifluoromethyl)isoxazole (i.e. the product from Step B of Example 2) (2.6 g, 6.65 mmol) and potassium carbonate (2.3 g, 16.6 mmol) in N,N-dimethylformamide (25 mL) was added benzyl mercaptan (0.782 mL, 6.65 mmol). The reaction mixture was heated at 90° C. for 4 h. The reaction mixture was then cooled and excess-water was added, and the mixture was extracted with ethyl acetate (2×100 mL). The organic extracts were dried ($MgSO_4$) and concentrated under reduced pressure to provide a solid residue. The crude product was partially purified by silica gel column chromatography eluted with mixtures of hexane and ethyl acetate to afford a product containing the title compound (about 80% purity, 2.8 g).

$^1$H NMR ($CDCl_3$) δ 7.50 (s, 2H), 7.41 (s, 2H); 7.42 (m, 2H), 7.26-7.40 (m, 7H), 4.16 (s, 2H); 4.1 (d, 1H), 3.65 (d, 1H).

Step B: Preparation of 4-[5-(3,5-dichlorophenyl)-4,5-dihydro-5-(trifluoromethyl)-3-isoxazolyl]-2-methylbenzenesulfonyl chloride To a solution of 5-(3,5-dichlorophenyl)-4,5-dihydro-3-[3-methyl-4-[(phenylmethyl)-thio]phenyl]-5-(trifluoromethyl)isoxazole (i.e. the product from Step A) (2.88 g, 5.8 mmol) in methylene chloride (50 mL) and water (50 mL) was added concentrated hydrochloride acid (1.92 mL, 20 mmol) at 5° C., followed by dropwise addition of sodium hypochlorite (6.15%—Clorox®brand) (50 mL). The reaction mixture was then stirred vigorously for 1 h. The reaction mixture was added to methylene chloride (100 mL) and washed with water (2×100 mL). The organic extracts were dried ($MgSO_4$) and concentrated to afford the title product as an oil (3.1 g).

$^1$H NMR-($CDCl_3$) δ 8.15-7.3 (m, 6H), 4.1 (d, 1H), 3.7 (d, 1H), 2.83 (s, 3H).

Step C: Preparation of 4-[5-(3,5-dichlorophenyl)-4,5-dihydro-5-(trifluoromethyl)-3-isoxazoyl]-2-methyl-N-(2-pyridinylmethyl)benzenesulfonamide To a solution of 4-[5-(3,5-dichlorophenyl)-4,5-dihydro-5-(trifluoromethyl)-3-isoxazolyl]-2-methylbenzenesulfonyl chloride (i.e. the product of Step B) (0.2 g, 0.42 mmol) in acetonitrile (20 mL) was added 2-(aminomethyl)pyridine (0.108 mL, 1.05 mmol). The reaction mixture was heated to reflux, and then allowed to stir at ambient temperature for 0.5 h. The mixture was then concentrated to dryness and the crude product was purified by silica gel chromatography using hexane:ethyl acetate (80:20) as eluent. The isolated product was triturated with a mixture of ether and hexane to afford the title product, a compound of the present invention, as a white solid (59 mg), m.p. 57-58° C.

$^1$H NMR (CDCl$_3$) δ 8.47 (d, 1H), 8.04 (d, 1H), 7.50-7.6 (m, 5H), 7.43 (s, 1H), 7.16 (m, 1H), 7.09 (d, 1H), 6.24 (br t, 1H), 4.23 (d, 1H), 4.04 (d, 1H), 3.71 (d, 1H), 2.70 (s, 1H).

Example 5

Preparation of 5-[5-(3,5-dichlorophenyl)-4,5-dihydro-5-(trifluoromethyl)-3-isoxazolyl]-2-(methylthio)benzonitrile To a stirred suspension of sodium thiomethoxide (0.21 g, 3 mmol) and potassium carbonate (0.28 g, 2 mmol) in 4 mL of N,N-dimethylformamide was added a solution of 5-[5-(3,5-dichlorophenyl)-4,5-dihydro-5-(trifluoromethyl)-3-isoxazolyl]-2-fluorobenzonitrile (prepared by a method similar to Example 2, Step A and Step B; 1.00 g, 2.48 mmol) in N,N-dimethylformamide (6 mL). This mixture was stirred at ambient temperature for 1 h. Then an additional portion of sodium thiomethoxide (0.21 g, 3 mmol) was added. After an additional 15 minutes, water was added, and the mixture was successively extracted with diethyl ether and ethyl acetate. The organic extracts were combined and washed several times with water and saturated aqueous sodium chloride solution, and then dried over magnesium sulfate, and concentrated to leave an off-white solid. The solid was triturated with a mixture of diethyl ether and hexanes, collected on a glass frit, and dried in air to afford the title compound, a compound of the present invention, as a white solid (1.04 g).

$^1$H NMR (acetone-d$_6$) δ 8.0-8.1 (m, 2H), 7.66 (s, 2H), 7.62 (s, 1H), 7.6 (m, 1H), 4.45 (d, 1H), 4.29 (d, 1H).

Example 6

Preparation of 5-[(3,5-dichlorophenyl)-4,5-dihydro-5-(trifluoromethyl)-3-isoxazolyl]-2-(methylsulfonyl)benzonitrile To a solution of 5-[(3,5-dichlorophenyl)-4,5-dihydro-5-(trifluoromethyl)-3-isoxazolyl]-2-(methylthio)benzonitrile (i.e. the product of Example 5) (0.42 g, 1.0 mmol) in 20 mL of dichloromethane was added 3-chloroperoxybenzoic acid (0.90 g of ~77% peracid, 4.0 mmol) in one portion, and the mixture was stirred at ambient temperature overnight. Aqueous sodium bisulfite solution was added, and after several minutes solid potassium carbonate was added. The layers were separated, and the organic phase was dried over magnesium sulfate and concentrated to leave a solid. The solid was triturated with a mixture of diethyl ether and hexanes, collected on a glass frit, and dried in air to afford the title product, a compound of the present invention, as a white solid (0.38 g).

$^1$H NMR (acetone-d$_6$) δ 8.42 (s, 1H), 8.38 (m, 1H), 8.26 (m, 1H), 7.67 (s, 3M), 4.59 (d, 1H), 4.41 (d, 1H), 3.39 (s, 3H).

Example 7

Preparation of 5-[5-(3,5-dichlorophenyl)-4,5-dihydro-3-[4-(methylsulfonyl)phenyl]-5-(trifluoromethyl)isoxazole Step A: Preparation of 3-(4-bromophenyl)-5-(3,5-dichlorophenyl)-5-dihydro-5-(trifluoromethyl)isoxazole To a solution of 4-bromobenzaldehyde (3.70 g, 20 mmol) in ethanol (30 mL) was added 50% aqueous hydroxylamine (1.25 mL, 21 mmol) and glacial acetic acid (1.25 mL, 21 mmol). After 30 minutes, the reaction mixture was diluted with ethyl acetate and washed with water and with saturated aqueous sodium chloride solution, dried over magnesium sulfate, and concentrated to leave a white solid. To a solution of this solid in tetrahydrofuran (80 mL) and 1,3-dichloro-5-[1-(trifluoromethyl)ethenyl]benzene (i.e. the product from Example 1, Step A) (4.82 g, 20 mmol) was added an aqueous solution of sodium hypochlorite (6.15%—Clorox® brand) (80 mL) dropwise over 1 h. The reaction mixture was stirred at ambient temperature for 16 h. The phases were separated, and the aqueous phase was extracted once with diethyl ether. The combined organic phases were washed with saturated aqueous sodium bisulfite solution and saturated aqueous sodium chloride solution, and dried over magnesium sulfate, and concentrated to leave a white solid. This solid was triturated with warm (40° C.) hexanes, allowed to cool, and solids were collected on a glass frit and dried to obtain the title product as a white solid (5.25 g).

$^1$H NMR (CDCl$_3$) δ 7.5-7.6 (m, 6H), 7.43 (s, 1M, 4.06 (d, 1H), 3.68 (d, 1H)

Step B: Preparation of 5-[5-(3,5-dichlorophenyl)-4,5-dihydro-3-[4-(methylsulfonyl)-phenyl]-5-(trifluoromethyl)isoxazole To a solution of 3-(4-bromophenyl)-5-(3,5-dichlorophenyl)-4,5-dihydro-5-(trifluoromethyl)isoxazole (i.e. the product of Step A) (4.39 mg, 1.00 mmol) in tetrahydrofuran (10 mL) cooled below −75° C. was added a solution of n-butyllithium (2.5 M solution in hexanes) dropwise over three minutes, while maintaining the temperature at or below −72° C. Within one minute, S-methyl methanesulfonothioate (0.11=L, 1.2 mmol) was added dropwise. The reaction mixture was allowed to stir and warm slowly to ambient temperature, and then it was poured into 1 N aqueous sodium hydroxide solution, and the mixture was extracted with ethyl acetate. The organic phase was washed with saturated aqueous sodium chloride solution, dried over magnesium sulfate; and concentrated. The residue was subjected to chromatography on silica gel eluted with 10% ethyl acetate in hexanes. The isolated material was redissolved in dichloromethane (5 mL), treated with 3-chloroperoxybenzoic acid (~77%, 0.39 g, 1.7 mmol) and allowed to stir at ambient temperature for 64 h. Additional 3-chloroperoxybenzoic acid (~77%, 0.27 g, 1.2 mmol) was added, and the mixture was stirred for 4 h. To this mixture was added saturated aqueous sodium bisulfite solution, and then solid potassium carbonate was added carefully until gas evolution ceased. The phases were separated, and the organic phase was washed with 1 N aqueous sodium hydroxide solution and with saturated aqueous sodium chloride solution, dried over magnesium sulfate, and concentrated. The residue was triturated with diethyl ether and hexanes to obtain a solid which was collected on a glass frit. The solid was washed with a mixture of diether and hexanes, and dried to afford the title product (0.12 g), a compound of the present invention.

$^1$H NMR (DMSO-d$_6$) δ 8.06 (m, 2H), 7.98 (m, 2H), 7.81 (s, 1H), 7.64 (m, 2H), 4.43 (d, 1H), 4.37 (d, 1H), 3.27 (s, 3H).

By the procedures described herein together with methods known in the art, the following compounds of Tables 1 to 13 can be prepared. The following abbreviations are used in the Tables which follow: —CN means cyano, —NO$_2$ means nitro, 2-Py means 2-pyridinyl, Ph means phenyl, Me means methyl, Et means ethyl, Pr means propyl, n means normal, i means iso, c means cyclo, i-Pr means isopropyl, c-Pr means cyclopropyl,

TABLE 1

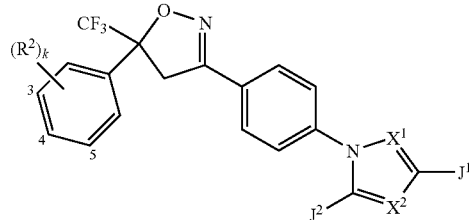

wherein k is 1, 2, 3, 4 or 5.

| (R²)ₖ | X¹ | X² | J¹ | J² |
|---|---|---|---|---|
| 3-Cl, 4-Cl | N | CH | H | H |
| 3-Cl, 4-Cl | N | CH | Cl | H |
| 3-Cl, 4-Cl | N | CH | Br | H |
| 3-Cl, 4-Cl | N | CH | CF₃ | H |
| 3-Cl, 4-Cl | N | CH | —CN | H |
| 3-Cl, 4-Cl | N | CH | CONHMe | H |
| 3-Cl, 4-Cl | N | CH | Me | H |
| 3-Cl, 4-Cl | N | CH | Ph | H |
| 3-Cl, 4-Cl | N | CH | H | CO₂Me |
| 3-Cl, 4-Cl | N | CH | H | CONHMe |
| 3-Cl, 4-Cl | N | CH | CF₃ | CO₂Me |
| 3-Cl, 4-Cl | N | CH | CF₃ | CONHMe |
| 3-Cl, 4-Cl | N | CH | Cl | CO₂Me |
| 3-Cl, 4-Cl | N | CH | Cl | CONHMe |
| 3-Cl, 4-Cl | N | CH | Br | CO₂Me |
| 3-Cl, 4-Cl | N | CH | Br | CONHMe |
| 3-Cl, 4-Cl | N | C—Cl | H | H |
| 3-Cl, 4-Cl | N | C—Cl | Cl | H |
| 3-Cl, 4-Cl | N | C—Cl | Br | H |
| 3-Cl, 4-Cl | N | C—Cl | CF₃ | H |
| 3-Cl, 4-Cl | N | C—Cl | —CN | H |
| 3-Cl, 4-Cl | N | C—Cl | CONHMe | H |
| 3-Cl, 4-Cl | N | C—Cl | Me | H |
| 3-Cl, 4-Cl | N | C—Cl | Ph | H |
| 3-Cl, 4-Cl | N | C—Cl | H | CO₂Me |
| 3-Cl, 4-Cl | N | C—Cl | H | CONHMe |
| 3-Cl, 4-Cl | N | C—Cl | CF₃ | CO₂Me |
| 3-Cl, 4-Cl | N | C—Cl | CF₃ | CONHMe |
| 3-Cl, 4-Cl | N | C—Cl | Cl | CO₂Me |
| 3-Cl, 4-Cl | N | C—Cl | Cl | CONHMe |
| 3-Cl, 4-Cl | N | C—Cl | Br | CO₂Me |
| 3-Cl, 4-Cl | N | C—Cl | Br | CONHMe |
| 3-Cl, 4-Cl | CH | N | H | H |
| 3-Cl, 4-Cl | CH | N | Me | H |
| 3-Cl, 4-Cl | CH | N | Ph | H |
| 3-Cl, 4-Cl | CH | N | Cl | H |
| 3-Cl, 4-Cl | CH | N | Br | H |
| 3-Cl, 4-Cl | CH | N | —CN | H |
| 3-Cl, 4-Cl | CH | N | CO₂Me | H |
| 3-Cl, 4-Cl | CH | N | CONHMe | H |
| 3-Cl, 4-Cl | CH | N | H | Me |
| 3-Cl, 4-Cl | CH | N | H | Et |
| 3-Cl, 4-Cl | CH | N | H | Pr |
| 3-Cl, 4-Cl | CH | N | H | Ph |
| 3-Cl, 4-Cl | CH | N | H | NO₂ |
| 3-Cl, 4-Cl | CH | N | Me | Me |
| 3-Cl, 4-Cl | N | N | Br | CO₂Me |
| 3-Cl, 4-Cl | N | N | Br | CONHMe |
| 3-Cl, 4-Cl | N | N | H | H |
| 3-Cl, 4-Cl | N | N | Cl | H |
| 3-Cl, 4-Cl | N | N | Br | H |
| 3-Cl, 4-Cl | N | N | —CN | H |
| 3-Cl, 4-Cl | N | N | —NO₂ | H |
| 3-Cl, 4-Cl | N | N | SMe | H |
| 3-Cl, 4-Cl | N | N | CO₂Me | H |
| 3-Cl, 4-Cl | N | N | Me | H |
| 3-Cl, 4-Cl | N | N | Ph | H |
| H | N | CH | H | H |
| 2-Cl | N | CH | H | H |
| 3-Cl | N | CH | H | H |
| 4-Cl | N | CH | H | H |
| 2-Cl, 4-Cl | N | CH | H | H |
| 2-F | N | CH | H | H |
| 3-F | N | CH | H | H |
| 4-F | N | CH | H | H |
| 2-F, 4-F | N | CH | H | H |
| 3-F, 4-F | N | CH | H | H |
| 3-F, 5-F | N | CH | H | H |
| 3-CF₃ | N | CH | H | H |
| 4-CF₃ | N | CH | H | H |
| 3-CF₃, 5-CF₃ | N | CH | H | H |
| 3-Br | N | CH | H | H |
| 4-Br | N | CH | H | H |
| 3-I | N | CH | H | H |
| 4-I | N | CH | H | H |
| 3-CN | N | CH | H | H |
| 4-CN | N | CH | H | H |
| 3-Me | N | CH | H | H |
| 4-Me | N | CH | H | H |
| 3-OMe | N | CH | H | H |
| 4-OMe | N | CH | H | H |
| H | N | N | H | H |
| 2-Cl | N | N | H | H |
| 3-Cl | N | N | H | H |
| 4-Cl | N | N | H | H |
| 2-Cl, 4-Cl | N | N | H | H |
| 2-F | N | N | H | H |
| 3-F | N | N | H | H |
| 4-F | N | N | H | H |
| 2-F, 4-F | N | N | H | H |
| 3-F, 4-F | N | N | H | H |
| 3-F, 5-F | N | N | H | H |
| 3-CF₃ | N | N | H | H |
| 3-Cl, 5-Cl | N | CH | H | H |
| 3-Cl, 5-Cl | N | CH | Cl | H |
| 3-Cl, 5-Cl | N | CH | Br | H |
| 3-Cl, 5-Cl | N | CH | CF₃ | H |
| 3-Cl, 5-Cl | N | CH | —CN | H |
| 3-Cl, 5-Cl | N | CH | CONHMe | H |
| 3-Cl, 5-Cl | N | CH | Me | H |
| 3-Cl, 5-Cl | N | CH | Ph | H |
| 3-Cl, 5-Cl | N | CH | H | CO₂Me |
| 3-Cl, 5-Cl | N | CH | H | CONHMe |
| 3-Cl, 5-Cl | N | CH | CF₃ | CO₂Me |
| 3-Cl, 5-Cl | N | CH | CF₃ | CONHMe |
| 3-Cl, 5-Cl | N | CH | Cl | CO₂Me |
| 3-Cl, 5-Cl | N | CH | Cl | CONHMe |
| 3-Cl, 5-Cl | N | CH | Br | CO₂Me |
| 3-Cl, 5-Cl | N | CH | Br | CONHMe |
| 3-Cl, 5-Cl | N | C—Cl | H | H |
| 3-Cl, 5-Cl | N | C—Cl | Cl | H |
| 3-Cl, 5-Cl | N | C—Cl | Br | H |
| 3-Cl, 5-Cl | N | C—Cl | CF₃ | H |
| 3-Cl, 5-Cl | N | C—Cl | —CN | H |
| 3-Cl, 5-Cl | N | C—Cl | CONHMe | H |
| 3-Cl, 5-Cl | N | C—Cl | Me | H |
| 3-Cl, 5-Cl | N | C—Cl | Ph | H |
| 3-Cl, 5-Cl | N | C—Cl | H | CO₂Me |
| 3-Cl, 5-Cl | N | C—Cl | H | CONHMe |
| 3-Cl, 5-Cl | N | C—Cl | CF₃ | CO₂Me |
| 3-Cl, 5-Cl | N | C—Cl | CF₃ | CONHMe |
| 3-Cl, 5-Cl | N | C—Cl | Cl | CO₂Me |
| 3-Cl, 5-Cl | N | C—Cl | Cl | CONHMe |
| 3-Cl, 5-Cl | N | C—Cl | Br | CO₂Me |
| 3-Cl, 5-Cl | N | C—Cl | Br | CONHMe |
| 3-Cl, 5-Cl | CH | N | H | H |

TABLE 1-continued

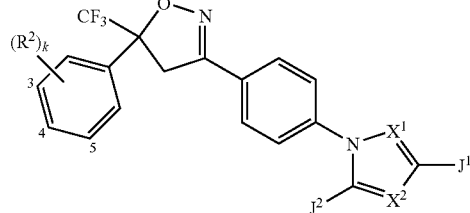

wherein k is 1, 2, 3, 4 or 5.

| $(R^2)_k$ | $X^1$ | $X^2$ | $J^1$ | $J^2$ |
|---|---|---|---|---|
| 3-Cl, 5-Cl | CH | N | Me | H |
| 3-Cl, 5-Cl | CH | N | Ph | H |
| 3-Cl, 5-Cl | CH | N | Cl | H |
| 3-Cl, 5-Cl | CH | N | Br | H |
| 3-Cl, 5-Cl | CH | N | —CN | H |
| 3-Cl, 5-Cl | CH | N | $CO_2Me$ | H |
| 3-Cl, 5-Cl | CH | N | CONHMe | H |
| 3-Cl, 5-Cl | CH | N | H | Me |
| 3-Cl, 5-Cl | CH | N | H | Et |
| 3-Cl, 5-Cl | CH | N | H | Pr |
| 3-Cl, 5-Cl | CH | N | H | Ph |
| 3-Cl, 5-Cl | CH | N | H | $NO_2$ |
| 3-Cl, 5-Cl | CH | N | Me | Me |
| 3-Cl, 5-Cl | N | N | Br | $CO_2Me$ |
| 3-Cl, 5-Cl | N | N | Br | CONHMe |
| 3-Cl, 5-Cl | N | N | H | H |
| 3-Cl, 5-Cl | N | N | Cl | H |
| 3-Cl, 5-Cl | N | N | Br | H |
| 3-Cl, 5-Cl | N | N | —CN | H |
| 3-Cl, 5-Cl | N | N | —$NO_2$ | H |
| 3-Cl, 5-Cl | N | N | SMe | H |
| 3-Cl, 5-Cl | N | N | $CO_2Me$ | H |
| 3-Cl, 5-Cl | N | N | Me | H |
| 3-Cl, 5-Cl | N | N | Ph | H |
| H | CH | N | H | H |
| 2-Cl | CH | N | H | H |
| 3-Cl | CH | N | H | H |
| 4-Cl | CH | N | H | H |
| 2-Cl, 4-Cl | CH | N | H | H |
| 2-F | CH | N | H | H |
| 3-F | CH | N | H | H |
| 4-F | CH | N | H | H |
| 2-F, 4-F | CH | N | H | H |
| 3-F, 4-F | CH | N | H | H |
| 3-F, 5-F | CH | N | H | H |
| 3-$CF_3$ | CH | N | H | H |
| 4-$CF_3$ | CH | N | H | H |
| 3-$CF_3$, 5-$CF_3$ | CH | N | H | H |
| 3-Br | CH | N | H | H |
| 4-Br | CH | N | H | H |
| 3-I | CH | N | H | H |
| 4-I | CH | N | H | H |
| 3-CN | CH | N | H | H |
| 4-CN | CH | N | H | H |
| 3-Me | CH | N | H | H |
| 4-Me | CH | N | H | H |
| 3-OMe | CH | N | H | H |
| 4-OMe | CH | N | H | H |
| 4-$CF_3$ | N | N | H | H |
| 3-$CF_3$, 5-$CF_3$ | N | N | H | H |
| 3-Br | N | N | H | H |
| 4-Br | N | N | H | H |
| 3-I | N | N | H | H |
| 4-I | N | N | H | H |
| 3-CN | N | N | H | H |
| 4-CN | N | N | H | H |
| 3-Me | N | N | H | H |
| 4-Me | N | N | H | H |
| 3-OMe | N | N | H | H |
| 4-OMe | N | N | H | H |

TABLE 2

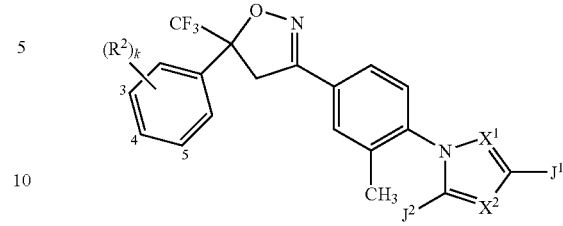

wherein k is 1, 2, 3, 4 or 5.

| $(R^2)_k$ | $X^1$ | $X^2$ | $J^1$ | $J^2$ |
|---|---|---|---|---|
| 3-Cl, 4-Cl | N | CH | H | H |
| 3-Cl, 4-Cl | N | CH | Cl | H |
| 3-Cl, 4-Cl | N | CH | Br | H |
| 3-Cl, 4-Cl | N | CH | $CF_3$ | H |
| 3-Cl, 4-Cl | N | CH | —CN | H |
| 3-Cl, 4-Cl | N | CH | CONHMe | H |
| 3-Cl, 4-Cl | N | CH | Me | H |
| 3-Cl, 4-Cl | N | CH | Ph | H |
| 3-Cl, 4-Cl | N | CH | H | $CO_2Me$ |
| 3-Cl, 4-Cl | N | CH | H | CONHMe |
| 3-Cl, 4-Cl | N | CH | $CF_3$ | $CO_2Me$ |
| 3-Cl, 4-Cl | N | CH | $CF_3$ | CONHMe |
| 3-Cl, 4-Cl | N | CH | Cl | $CO_2Me$ |
| 3-Cl, 4-Cl | N | CH | Cl | CONHMe |
| 3-Cl, 4-Cl | N | CH | Br | $CO_2Me$ |
| 3-Cl, 4-Cl | N | CH | Br | CONHMe |
| 3-Cl, 4-Cl | N | C—Cl | H | H |
| 3-Cl, 4-Cl | N | C—Cl | Cl | H |
| 3-Cl, 4-Cl | N | C—Cl | Br | H |
| 3-Cl, 4-Cl | N | C—Cl | $CF_3$ | H |
| 3-Cl, 4-Cl | N | C—Cl | —CN | H |
| 3-Cl, 4-Cl | N | C—Cl | CONHMe | H |
| 3-Cl, 4-Cl | N | C—Cl | Me | H |
| 3-Cl, 4-Cl | N | C—Cl | Ph | H |
| 3-Cl, 4-Cl | N | C—Cl | H | $CO_2Me$ |
| 3-Cl, 4-Cl | N | C—Cl | H | CONHMe |
| 3-Cl, 4-Cl | N | C—Cl | $CF_3$ | $CO_2Me$ |
| 3-Cl, 4-Cl | N | C—Cl | $CF_3$ | CONHMe |
| 3-Cl, 4-Cl | N | C—Cl | Cl | $CO_2Me$ |
| 3-Cl, 4-Cl | N | C—Cl | Cl | CONHMe |
| 3-Cl, 4-Cl | N | C—Cl | Br | $CO_2Me$ |
| 3-Cl, 4-Cl | N | C—Cl | Br | CONHMe |
| 3-Cl, 4-Cl | CH | N | H | H |
| 3-Cl, 4-Cl | CH | N | Me | H |
| 3-Cl, 4-Cl | CH | N | Ph | H |
| 3-Cl, 4-Cl | CH | N | Cl | H |
| 3-Cl, 4-Cl | CH | N | Br | H |
| 3-Cl, 4-Cl | CH | N | —CN | H |
| 3-Cl, 4-Cl | CH | N | $CO_2Me$ | H |
| 3-Cl, 4-Cl | CH | N | CONHMe | H |
| 3-Cl, 4-Cl | CH | N | H | Me |
| 3-Cl, 4-Cl | CH | N | H | Et |
| 3-Cl, 4-Cl | CH | N | H | n-Pr |
| 3-Cl, 4-Cl | CH | N | H | Ph |
| 3-Cl, 4-Cl | CH | N | H | $NO_2$ |
| 3-Cl, 4-Cl | CH | N | Me | Me |
| 3-Cl, 4-Cl | N | N | Br | $CO_2Me$ |
| 3-Cl, 4-Cl | N | N | Br | CONHMe |
| 3-Cl, 4-Cl | N | N | H | H |
| 3-Cl, 4-Cl | N | N | Cl | H |
| 3-Cl, 4-Cl | N | N | Br | H |
| 3-Cl, 4-Cl | N | N | —CN | H |
| 3-Cl, 4-Cl | N | N | —$NO_2$ | H |
| 3-Cl, 4-Cl | N | N | SMe | H |
| 3-Cl, 4-Cl | N | N | $CO_2Me$ | H |
| 3-Cl, 4-Cl | N | N | Me | H |
| 3-Cl, 4-Cl | N | N | Ph | H |
| H | N | CH | H | H |
| 2-Cl | N | CH | H | H |
| 3-Cl | N | CH | H | H |
| 4-Cl | N | CH | H | H |
| 2-Cl, 4-Cl | N | CH | H | H |
| 2-F | N | CH | H | H |

TABLE 2-continued

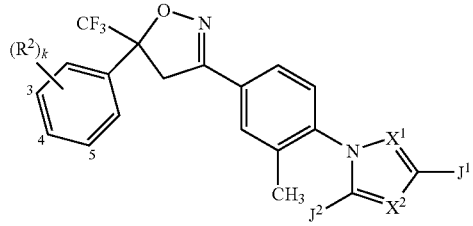
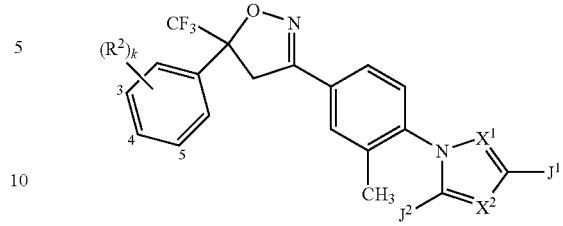

wherein k is 1, 2, 3, 4 or 5.

| (R²)ₖ | X¹ | X² | J¹ | J² |
|---|---|---|---|---|
| 3-F | N | CH | H | H |
| 4-F | N | CH | H | H |
| 2-F, 4-F | N | CH | H | H |
| 3-F, 4-F | N | CH | H | H |
| 3-F, 5-F | N | CH | H | H |
| 3-CF₃ | N | CH | H | H |
| 4-CF₃ | N | CH | H | H |
| 3-CF₃, 5-CF₃ | N | CH | H | H |
| 3-Br | N | CH | H | H |
| 4-Br | N | CH | H | H |
| 3-I | N | CH | H | H |
| 4-I | N | CH | H | H |
| 3-CN | N | CH | H | H |
| 4-CN | N | CH | H | H |
| 3-Me | N | CH | H | H |
| 4-Me | N | CH | H | H |
| 3-OMe | N | CH | H | H |
| 4-OMe | N | CH | H | H |
| H | N | N | H | H |
| 2-Cl | N | N | H | H |
| 3-Cl | N | N | H | H |
| 4-Cl | N | N | H | H |
| 2-Cl, 4-Cl | N | N | H | H |
| 2-F | N | N | H | H |
| 3-F | N | N | H | H |
| 4-F | N | N | H | H |
| 2-F, 4-F | N | N | H | H |
| 3-F, 4-F | N | N | H | H |
| 3-F, 5-F | N | N | H | H |
| 3-CF₃ | N | N | H | H |
| 3-Cl, 5-Cl | N | CH | H | H |
| 3-Cl, 5-Cl | N | CH | Cl | H |
| 3-Cl, 5-Cl | N | CH | Br | H |
| 3-Cl, 5-Cl | N | CH | CF₃ | H |
| 3-Cl, 5-Cl | N | CH | —CN | H |
| 3-Cl, 5-Cl | N | CH | CONHMe | H |
| 3-Cl, 5-Cl | N | CH | Me | H |
| 3-Cl, 5-Cl | N | CH | Ph | H |
| 3-Cl, 5-Cl | N | CH | H | CO₂Me |
| 3-Cl, 5-Cl | N | CH | H | CONHMe |
| 3-Cl, 5-Cl | N | CH | CF₃ | CO₂Me |
| 3-Cl, 5-Cl | N | CH | CF₃ | CONHMe |
| 3-Cl, 5-Cl | N | CH | Cl | CO₂Me |
| 3-Cl, 5-Cl | N | CH | Cl | CONHMe |
| 3-Cl, 5-Cl | N | CH | Br | CO₂Me |
| 3-Cl, 5-Cl | N | CH | Br | CONHMe |
| 3-Cl, 5-Cl | N | C—Cl | H | H |
| 3-Cl, 5-Cl | N | C—Cl | Cl | H |
| 3-Cl, 5-Cl | N | C—Cl | Br | H |
| 3-Cl, 5-Cl | N | C—Cl | CF₃ | H |
| 3-Cl, 5-Cl | N | C—Cl | —CN | H |
| 3-Cl, 5-Cl | N | C—Cl | CONHMe | H |
| 3-Cl, 5-Cl | N | C—Cl | Me | H |
| 3-Cl, 5-Cl | N | C—Cl | Ph | H |
| 3-Cl, 5-Cl | N | C—Cl | H | CO₂Me |
| 3-Cl, 5-Cl | N | C—Cl | H | CONHMe |
| 3-Cl, 5-Cl | N | C—Cl | CF₃ | CO₂Me |
| 3-Cl, 5-Cl | N | C—Cl | CF₃ | CONHMe |
| 3-Cl, 5-Cl | N | C—Cl | Cl | CO₂Me |
| 3-Cl, 5-Cl | N | C—Cl | Cl | CONHMe |
| 3-Cl, 5-Cl | N | C—Cl | Br | CO₂Me |
| 3-Cl, 5-Cl | N | C—Cl | Br | CONHMe |
| 3-Cl, 5-Cl | CH | N | H | H |
| 3-Cl, 5-Cl | CH | N | Me | H |
| 3-Cl, 5-Cl | CH | N | Ph | H |
| 3-Cl, 5-Cl | CH | N | Cl | H |
| 3-Cl, 5-Cl | CH | N | Br | H |
| 3-Cl, 5-Cl | CH | N | —CN | H |
| 3-Cl, 5-Cl | CH | N | CO₂Me | H |
| 3-Cl, 5-Cl | CH | N | CONHMe | H |
| 3-Cl, 5-Cl | CH | N | H | Me |
| 3-Cl, 5-Cl | CH | N | H | Et |
| 3-Cl, 5-Cl | CH | N | H | n-Pr |
| 3-Cl, 5-Cl | CH | N | H | Ph |
| 3-Cl, 5-Cl | CH | N | H | NO₂ |
| 3-Cl, 5-Cl | CH | N | Me | Me |
| 3-Cl, 5-Cl | N | N | Br | CO₂Me |
| 3-Cl, 5-Cl | N | N | Br | CONHMe |
| 3-Cl, 5-Cl | N | N | H | H |
| 3-Cl, 5-Cl | N | N | Cl | H |
| 3-Cl, 5-Cl | N | N | Br | H |
| 3-Cl, 5-Cl | N | N | —CN | H |
| 3-Cl, 5-Cl | N | N | —NO₂ | H |
| 3-Cl, 5-Cl | N | N | SMe | H |
| 3-Cl, 5-Cl | N | N | CO₂Me | H |
| 3-Cl, 5-Cl | N | N | Me | H |
| 3-Cl, 5-Cl | N | N | Ph | H |
| H | CH | N | H | H |
| 2-Cl | CH | N | H | H |
| 3-Cl | CH | N | H | H |
| 4-Cl | CH | N | H | H |
| 2-Cl, 4-Cl | CH | N | H | H |
| 2-F | CH | N | H | H |
| 3-F | CH | N | H | H |
| 4-F | CH | N | H | H |
| 2-F, 4-F | CH | N | H | H |
| 3-F, 4-F | CH | N | H | H |
| 3-F, 5-F | CH | N | H | H |
| 3-CF₃ | CH | N | H | H |
| 4-CF₃ | CH | N | H | H |
| 3-CF₃, 5-CF₃ | CH | N | H | H |
| 3-Br | CH | N | H | H |
| 4-Br | CH | N | H | H |
| 3-I | CH | N | H | H |
| 4-I | CH | N | H | H |
| 3-CN | CH | N | H | H |
| 4-CN | CH | N | H | H |
| 3-Me | CH | N | H | H |
| 4-Me | CH | N | H | H |
| 3-OMe | CH | N | H | H |
| 4-OMe | CH | N | H | H |
| 4-CF₃ | N | N | H | H |
| 3-CF₃, 5-CF₃ | N | N | H | H |
| 3-Br | N | N | H | H |
| 4-Br | N | N | H | H |
| 3-I | N | N | H | H |
| 4-I | N | N | H | H |
| 3-CN | N | N | H | H |
| 4-CN | N | N | H | H |
| 3-Me | N | N | H | H |
| 4-Me | N | N | H | H |
| 3-OMe | N | N | H | H |
| 4-OMe | N | N | H | H |

TABLE 3

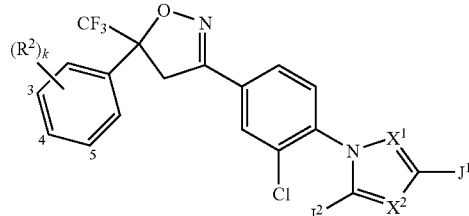

wherein k is 1, 2, 3, 4 or 5.

| (R²)ₖ | X¹ | X² | J¹ | J² |
|---|---|---|---|---|
| 3-Cl, 4-Cl | N | CH | H | H |
| 3-Cl, 4-Cl | N | CH | Cl | H |
| 3-Cl, 4-Cl | N | CH | Br | H |
| 3-Cl, 4-Cl | N | CH | CF₃ | H |
| 3-Cl, 4-Cl | N | CH | —CN | H |
| 3-Cl, 4-Cl | N | CH | CONHMe | H |
| 3-Cl, 4-Cl | N | CH | Me | H |
| 3-Cl, 4-Cl | N | CH | Ph | H |
| 3-Cl, 4-Cl | N | CH | H | CO₂Me |
| 3-Cl, 4-Cl | N | CH | H | CONHMe |
| 3-Cl, 4-Cl | N | CH | CF₃ | CO₂Me |
| 3-Cl, 4-Cl | N | CH | CF₃ | CONHMe |
| 3-Cl, 4-Cl | N | CH | Cl | CO₂Me |
| 3-Cl, 4-Cl | N | CH | Cl | CONHMe |
| 3-Cl, 4-Cl | N | CH | Br | CO₂Me |
| 3-Cl, 4-Cl | N | CH | Br | CONHMe |
| 3-Cl, 4-Cl | N | C—Cl | H | H |
| 3-Cl, 4-Cl | N | C—Cl | Cl | H |
| 3-Cl, 4-Cl | N | C—Cl | Br | H |
| 3-Cl, 4-Cl | N | C—Cl | CF₃ | H |
| 3-Cl, 4-Cl | N | C—Cl | —CN | H |
| 3-Cl, 4-Cl | N | C—Cl | CONHMe | H |
| 3-Cl, 4-Cl | N | C—Cl | Me | H |
| 3-Cl, 4-Cl | N | C—Cl | Ph | H |
| 3-Cl, 4-Cl | N | C—Cl | H | CO₂Me |
| 3-Cl, 4-Cl | N | C—Cl | H | CONHMe |
| 3-Cl, 4-Cl | N | C—Cl | CF₃ | CO₂Me |
| 3-Cl, 4-Cl | N | C—Cl | CF₃ | CONHMe |
| 3-Cl, 4-Cl | N | C—Cl | Cl | CO₂Me |
| 3-Cl, 4-Cl | N | C—Cl | Cl | CONHMe |
| 3-Cl, 4-Cl | N | C—Cl | Br | CO₂Me |
| 3-Cl, 4-Cl | N | C—Cl | Br | CONHMe |
| 3-Cl, 4-Cl | CH | N | H | H |
| 3-Cl, 4-Cl | CH | N | Me | H |
| 3-Cl, 4-Cl | CH | N | Ph | H |
| 3-Cl, 4-Cl | CH | N | Cl | H |
| 3-Cl, 4-Cl | CH | N | Br | H |
| 3-Cl, 4-Cl | CH | N | —CN | H |
| 3-Cl, 4-Cl | CH | N | CO₂Me | H |
| 3-Cl, 4-Cl | CH | N | CONHMe | H |
| 3-Cl, 4-Cl | CH | N | H | Me |
| 3-Cl, 4-Cl | CH | N | H | Et |
| 3-Cl, 4-Cl | CH | N | H | n-Pr |
| 3-Cl, 4-Cl | CH | N | H | Ph |
| 3-Cl, 4-Cl | CH | N | H | NO₂ |
| 3-Cl, 4-Cl | CH | N | Me | Me |
| 3-Cl, 4-Cl | N | N | Br | CO₂Me |
| 3-Cl, 4-Cl | N | N | Br | CONHMe |
| 3-Cl, 4-Cl | N | N | H | H |
| 3-Cl, 4-Cl | N | N | Cl | H |
| 3-Cl, 4-Cl | N | N | Br | H |
| 3-Cl, 4-Cl | N | N | —CN | H |
| 3-Cl, 4-Cl | N | N | NO₂ | H |
| 3-Cl, 4-Cl | N | N | SMe | H |
| 3-Cl, 4-Cl | N | N | CO₂Me | H |
| 3-Cl, 4-Cl | N | N | Me | H |
| 3-Cl, 4-Cl | N | N | Ph | H |
| H | N | CH | H | H |
| 2-Cl | N | CH | H | H |
| 3-Cl | N | CH | H | H |
| 4-Cl | N | CH | H | H |
| 2-Cl, 4-Cl | N | CH | H | H |
| 2-F | N | CH | H | H |
| 3-F | N | CH | H | H |
| 4-F | N | CH | H | H |
| 2-F, 4-F | N | CH | H | H |
| 3-F, 4-F | N | CH | H | H |
| 3-F, 5-F | N | CH | H | H |
| 3-CF₃ | N | CH | H | H |
| 4-CF₃ | N | CH | H | H |
| 3-CF₃, 5-CF₃ | N | CH | H | H |
| 3-Br | N | CH | H | H |
| 4-Br | N | CH | H | H |
| 3-I | N | CH | H | H |
| 4-I | N | CH | H | H |
| 3-CN | N | CH | H | H |
| 4-CN | N | CH | H | H |
| 3-Me | N | CH | H | H |
| 4-Me | N | CH | H | H |
| 3-OMe | N | CH | H | H |
| 4-OMe | N | CH | H | H |
| H | N | N | H | H |
| 2-Cl | N | N | H | H |
| 3-Cl | N | N | H | H |
| 4-Cl | N | N | H | H |
| 2-Cl, 4-Cl | N | N | H | H |
| 2-F | N | N | H | H |
| 3-F | N | N | H | H |
| 4-F | N | N | H | H |
| 2-F, 4-F | N | N | H | H |
| 3-F, 4-F | N | N | H | H |
| 3-F, 5-F | N | N | H | H |
| 3-CF₃ | N | N | H | H |
| 3-Cl, 5-Cl | N | CH | H | H |
| 3-Cl, 5-Cl | N | CH | Cl | H |
| 3-Cl, 5-Cl | N | CH | Br | H |
| 3-Cl, 5-Cl | N | CH | CF₃ | H |
| 3-Cl, 5-Cl | N | CH | —CN | H |
| 3-Cl, 5-Cl | N | CH | CONHMe | H |
| 3-Cl, 5-Cl | N | CH | Me | H |
| 3-Cl, 5-Cl | N | CH | Ph | H |
| 3-Cl, 5-Cl | N | CH | H | CO₂Me |
| 3-Cl, 5-Cl | N | CH | H | CONHMe |
| 3-Cl, 5-Cl | N | CH | CF₃ | CO₂Me |
| 3-Cl, 5-Cl | N | CH | CF₃ | CONHMe |
| 3-Cl, 5-Cl | N | CH | Cl | CO₂Me |
| 3-Cl, 5-Cl | N | CH | Cl | CONHMe |
| 3-Cl, 5-Cl | N | CH | Br | CO₂Me |
| 3-Cl, 5-Cl | N | CH | Br | CONHMe |
| 3-Cl, 5-Cl | N | C—Cl | H | H |
| 3-Cl, 5-Cl | N | C—Cl | Cl | H |
| 3-Cl, 5-Cl | N | C—Cl | Br | H |
| 3-Cl, 5-Cl | N | C—Cl | CF₃ | H |
| 3-Cl, 5-Cl | N | C—Cl | —CN | H |
| 3-Cl, 5-Cl | N | C—Cl | CONHMe | H |
| 3-Cl, 5-Cl | N | C—Cl | Me | H |
| 3-Cl, 5-Cl | N | C—Cl | Ph | H |
| 3-Cl, 5-Cl | N | C—Cl | H | CO₂Me |
| 3-Cl, 5-Cl | N | C—Cl | H | CONHMe |
| 3-Cl, 5-Cl | N | C—Cl | CF₃ | CO₂Me |
| 3-Cl, 5-Cl | N | C—Cl | CF₃ | CONHMe |
| 3-Cl, 5-Cl | N | C—Cl | Cl | CO₂Me |
| 3-Cl, 5-Cl | N | C—Cl | Cl | CONHMe |
| 3-Cl, 5-Cl | N | C—Cl | Br | CO₂Me |
| 3-Cl, 5-Cl | N | C—Cl | Br | CONHMe |
| 3-Cl, 5-Cl | CH | N | H | H |

TABLE 3-continued

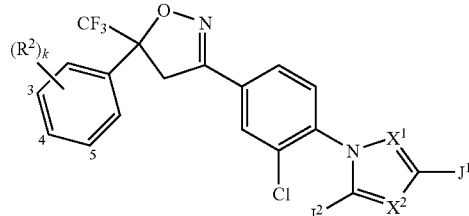

wherein k is 1, 2, 3, 4 or 5.

| (R²)ₖ | X¹ | X² | J¹ | J² |
|---|---|---|---|---|
| 3-Cl, 5-Cl | CH | N | Me | H |
| 3-Cl, 5-Cl | CH | N | Ph | H |
| 3-Cl, 5-Cl | CH | N | Cl | H |
| 3-Cl, 5-Cl | CH | N | Br | H |
| 3-Cl, 5-Cl | CH | N | —CN | H |
| 3-Cl, 5-Cl | CH | N | CO₂Me | H |
| 3-Cl, 5-Cl | CH | N | CONHMe | H |
| 3-Cl, 5-Cl | CH | N | H | Me |
| 3-Cl, 5-Cl | CH | N | H | Et |
| 3-Cl, 5-Cl | CH | N | H | n-Pr |
| 3-Cl, 5-Cl | CH | N | H | Ph |
| 3-Cl, 5-Cl | CH | N | H | NO₂ |
| 3-Cl, 5-Cl | CH | N | Me | Me |
| 3-Cl, 5-Cl | N | N | Br | CO₂Me |
| 3-Cl, 5-Cl | N | N | Br | CONHMe |
| 3-Cl, 5-Cl | N | N | H | H |
| 3-Cl, 5-Cl | N | N | Cl | H |
| 3-Cl, 5-Cl | N | N | Br | H |
| 3-Cl, 5-Cl | N | N | —CN | H |
| 3-Cl, 5-Cl | N | N | NO₂ | H |
| 3-Cl, 5-Cl | N | N | SMe | H |
| 3-Cl, 5-Cl | N | N | CO₂Me | H |
| 3-Cl, 5-Cl | N | N | Me | H |
| 3-Cl, 5-Cl | N | N | Ph | H |
| H | CH | N | H | H |
| 2-Cl | CH | N | H | H |
| 3-Cl | CH | N | H | H |
| 4-Cl | CH | N | H | H |
| 2-Cl, 4-Cl | CH | N | H | H |
| 2-F | CH | N | H | H |
| 3-F | CH | N | H | H |
| 4-F | CH | N | H | H |
| 2-F, 4-F | CH | N | H | H |
| 3-F, 4-F | CH | N | H | H |
| 3-F, 5-F | CH | N | H | H |
| 3-CF₃ | CH | N | H | H |
| 4-CF₃ | CH | N | H | H |
| 3-CF₃, 5-CF₃ | CH | N | H | H |
| 3-Br | CH | N | H | H |
| 4-Br | CH | N | H | H |
| 3-I | CH | N | H | H |
| 4-I | CH | N | H | H |
| 3-CN | CH | N | H | H |
| 4-CN | CH | N | H | H |
| 3-Me | CH | N | H | H |
| 4-Me | CH | N | H | H |
| 3-OMe | CH | N | H | H |
| 4-OMe | CH | N | H | H |
| 4-CF₃ | N | N | H | H |
| 3-CF₃, 5-CF₃ | N | N | H | H |
| 3-Br | N | N | H | H |
| 4-Br | N | N | H | H |
| 3-I | N | N | H | H |
| 4-I | N | N | H | H |
| 3-CN | N | N | H | H |
| 4-CN | N | N | H | H |
| 3-Me | N | N | H | H |
| 4-Me | N | N | H | H |
| 3-OMe | N | N | H | H |
| 4-OMe | N | N | H | H |

TABLE 4

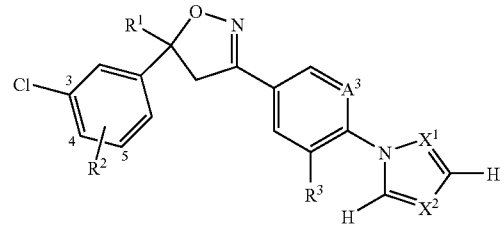

| R¹ | R² | R³ | X¹ | X² | A³ |
|---|---|---|---|---|---|
| Me | 4-Cl | H | N | CH | CH |
| Me | 5-Cl | H | N | CH | CH |
| Me | 4-Cl | H | CH | N | CH |
| Me | 5-Cl | H | CH | N | CH |
| Me | 4-Cl | H | N | N | CH |
| Me | 5-Cl | H | N | N | CH |
| Me | 4-Cl | Me | N | CH | CH |
| Me | 5-Cl | Me | N | CH | CH |
| Me | 4-Cl | Me | CH | N | CH |
| Me | 5-Cl | Me | CH | N | CH |
| Me | 4-Cl | Me | N | N | CH |
| Me | 5-Cl | Me | N | N | CH |
| Me | 4-Cl | Cl | N | CH | CH |
| Me | 5-Cl | Cl | N | CH | CH |
| Me | 4-Cl | Cl | CH | N | CH |
| Me | 5-Cl | Cl | CH | N | CH |
| Me | 4-Cl | Cl | N | N | CH |
| Me | 5-Cl | Cl | N | N | CH |
| CF₃ | 4-Cl | H | N | CH | N |
| CF₃ | 5-Cl | H | N | CH | N |
| CF₃ | 4-Cl | H | CH | N | N |
| CF₃ | 5-Cl | H | CH | N | N |
| CF₃ | 4-Cl | H | N | N | N |
| CF₃ | 5-Cl | H | N | N | N |
| CF₃ | 4-Cl | Me | N | CH | N |
| CF₃ | 5-Cl | Me | N | CN | N |
| CF₃ | 4-Cl | Me | CH | N | N |
| CF₃ | 5-Cl | Me | CH | N | N |
| CF₃ | 4-Cl | Me | N | N | N |
| CF₃ | 5-Cl | Me | N | N | N |
| CF₃ | 4-Cl | Cl | N | CH | N |
| CF₃ | 5-Cl | Cl | N | CH | N |
| CF₃ | 4-Cl | Cl | CH | N | N |
| CF₃ | 5-Cl | Cl | CH | N | N |
| CF₃ | 4-Cl | Cl | N | N | N |
| CF₃ | 5-Cl | Cl | N | N | N |

TABLE 5

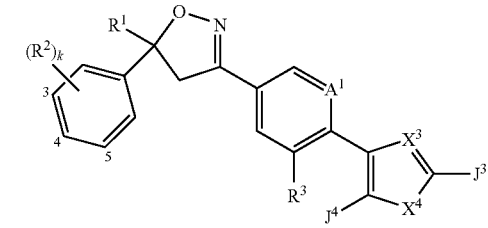

wherein k is 1, 2, 3, 4 or 5.

| R¹ | (R²)ₖ | R³ | X³ | X⁴ | J³ | J⁴ | A³ |
|---|---|---|---|---|---|---|---|
| CF₃ | 3-Cl, 4-Cl | H | CH | S | H | H | CH |
| CF₃ | 3-Cl, 4-Cl | H | CH | O | H | H | CH |
| CF₃ | 3-Cl, 4-Cl | H | CH | NMe | H | H | CH |
| CF₃ | 3-Cl, 4-Cl | H | N | S | H | H | CH |
| CF₃ | 3-Cl, 4-Cl | H | N | O | H | H | CH |
| CF₃ | 3-Cl, 5-Cl | H | CH | S | H | H | CH |
| CF₃ | 3-Cl, 5-Cl | H | CH | O | H | H | CH |
| CF₃ | 3-Cl, 5-Cl | H | CH | NMe | H | H | CH |

TABLE 5-continued

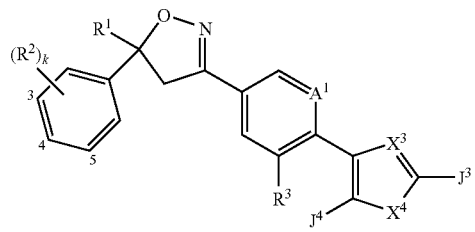

wherein k is 1, 2, 3, 4 or 5.

| R¹ | (R²)ₖ | R³ | X³ | X⁴ | J³ | J⁴ | A³ |
|---|---|---|---|---|---|---|---|
| CF₃ | 3-Cl, 5-Cl | H | N | S | H | H | CH |
| CF₃ | 3-Cl, 5-Cl | H | N | O | H | H | CH |
| CF₃ | 3-Cl, 4-Cl | Me | CH | S | H | H | CH |
| CF₃ | 3-Cl, 4-Cl | Me | CH | O | H | H | CH |
| CF₃ | 3-Cl, 4-Cl | Me | CH | NMe | H | H | CH |
| CF₃ | 3-Cl, 4-Cl | Me | N | S | H | H | CH |
| CF₃ | 3-Cl, 4-Cl | Me | N | O | H | H | CH |
| CF₃ | 3-Cl, 5-Cl | Me | CH | S | H | H | CH |
| CF₃ | 3-Cl, 5-Cl | Me | CH | O | H | H | CH |
| CF₃ | 3-Cl, 5-Cl | Me | CH | NMe | H | H | CH |
| CF₃ | 3-Cl, 5-Cl | Me | N | S | H | H | CH |
| CF₃ | 3-Cl, 5-Cl | Me | N | O | H | H | CH |
| CF₃ | 3-Cl, 4-Cl | H | CH | S | H | H | N |
| CF₃ | 3-Cl, 4-Cl | H | CH | O | H | H | N |
| CF₃ | 3-Cl, 4-Cl | H | CH | NMe | H | H | N |
| CF₃ | 3-Cl, 4-Cl | H | N | S | H | H | N |
| CF₃ | 3-Cl, 4-Cl | H | N | O | H | H | N |
| CF₃ | 3-Cl, 5-Cl | H | CH | S | H | H | N |
| CF₃ | 3-Cl, 5-Cl | H | CH | O | H | H | N |
| CF₃ | 3-Cl, 5-Cl | H | CH | NMe | H | H | N |
| CF₃ | 3-Cl, 5-Cl | H | N | S | H | H | N |
| CF₃ | 3-Cl, 5-Cl | H | N | O | H | H | N |
| Me | 3-Cl, 4-Cl | H | CH | S | H | H | CH |
| Me | 3-Cl, 4-Cl | H | CH | O | H | H | CH |
| Me | 3-Cl, 4-Cl | H | CH | NMe | H | H | CH |
| Me | 3-Cl, 4-Cl | H | N | S | H | H | CH |
| Me | 3-Cl, 4-Cl | H | N | O | H | H | CH |
| Me | 3-Cl, 5-Cl | H | CH | S | H | H | CH |
| Me | 3-Cl, 5-Cl | H | CH | O | H | H | CH |
| Me | 3-Cl, 5-Cl | H | CH | NMe | H | H | CH |
| Me | 3-Cl, 5-Cl | H | N | S | H | H | CH |
| Me | 3-Cl, 5-Cl | H | N | O | H | H | CH |
| CF₃ | 3-Cl, 4-Cl | H | CH | S | Cl | H | CH |
| CF₃ | 3-Cl, 4-Cl | H | CH | O | Cl | H | CH |
| CF₃ | 3-Cl, 4-Cl | H | CH | NMe | Cl | H | CH |
| CF₃ | 3-Cl, 4-Cl | H | N | S | Cl | H | CH |
| CF₃ | 3-Cl, 4-Cl | H | N | O | Cl | H | CH |
| CF₃ | 3-Cl, 5-Cl | H | CH | S | Cl | H | CH |
| CF₃ | 3-Cl, 5-Cl | H | CH | O | Cl | H | CH |
| CF₃ | 3-Cl, 5-Cl | H | CH | NMe | Cl | H | CH |
| CF₃ | 3-Cl, 5-Cl | H | N | S | Cl | H | CH |
| CF₃ | 3-Cl, 5-Cl | H | N | O | Cl | H | CH |
| CF₃ | 3-Cl, 4-Cl | H | CH | S | Cl | Cl | CH |
| CF₃ | 3-Cl, 4-Cl | H | CH | O | Cl | Cl | CH |
| CF₃ | 3-Cl, 4-Cl | H | CH | NMe | Cl | Cl | CH |
| CF₃ | 3-Cl, 4-Cl | H | N | S | Cl | Cl | CH |
| CF₃ | 3-Cl, 4-Cl | H | N | O | Cl | Cl | CH |
| CF₃ | 3-Cl, 5-Cl | H | CH | S | Cl | Cl | CH |
| CF₃ | 3-Cl, 5-Cl | H | CH | O | Cl | Cl | CH |
| CF₃ | 3-Cl, 5-Cl | H | CH | NMe | Cl | Cl | CH |
| CF₃ | 3-Cl, 5-Cl | H | N | S | Cl | Cl | CH |
| CF₃ | 3-Cl, 5-Cl | H | N | O | Cl | Cl | CH |

TABLE 6

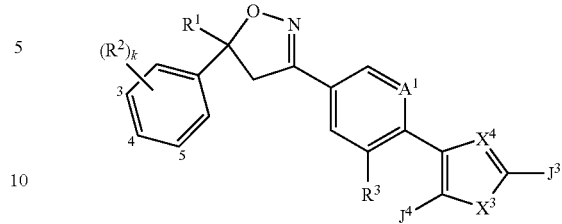

wherein k is 1, 2, 3, 4 or 5.

| R¹ | (R²)ₖ | R³ | X³ | X⁴ | J³ | J⁴ | A³ |
|---|---|---|---|---|---|---|---|
| CF₃ | 3-Cl, 4-Cl | H | CH | S | H | H | CH |
| CF₃ | 3-Cl, 4-Cl | H | CH | O | H | H | CH |
| CF₃ | 3-Cl, 4-Cl | H | CH | NMe | H | H | CH |
| CF₃ | 3-Cl, 4-Cl | H | N | S | H | H | CH |
| CF₃ | 3-Cl, 4-Cl | H | N | O | H | H | CH |
| CF₃ | 3-Cl, 5-Cl | H | CH | S | H | H | CH |
| CF₃ | 3-Cl, 5-Cl | H | CH | O | H | H | CH |
| CF₃ | 3-Cl, 5-Cl | H | CH | NMe | H | H | CH |
| CF₃ | 3-Cl, 5-Cl | H | N | S | H | H | CH |
| CF₃ | 3-Cl, 5-Cl | H | N | O | H | H | CH |
| CF₃ | 3-Cl, 4-Cl | Me | CH | S | H | H | CH |
| CF₃ | 3-Cl, 4-Cl | Me | CH | O | H | H | CH |
| CF₃ | 3-Cl, 4-Cl | Me | CH | NMe | H | H | CH |
| CF₃ | 3-Cl, 4-Cl | Me | N | S | H | H | CH |
| CF₃ | 3-Cl, 4-Cl | Me | N | O | H | H | CH |
| CF₃ | 3-Cl, 5-Cl | Me | CH | S | H | H | CH |
| CF₃ | 3-Cl, 5-Cl | Me | CH | O | H | H | CH |
| CF₃ | 3-Cl, 5-Cl | Me | CH | NMe | H | H | CH |
| CF₃ | 3-Cl, 5-Cl | Me | N | S | H | H | CH |
| CF₃ | 3-Cl, 5-Cl | Me | N | O | H | H | CH |
| CF₃ | 3-Cl, 4-Cl | H | CH | S | H | H | N |
| CF₃ | 3-Cl, 4-Cl | H | CH | O | H | H | N |
| CF₃ | 3-Cl, 4-Cl | H | CH | NMe | H | H | N |
| CF₃ | 3-Cl, 4-Cl | H | N | S | H | H | N |
| CF₃ | 3-Cl, 4-Cl | H | N | O | H | H | N |
| CF₃ | 3-Cl, 5-Cl | H | CH | S | H | H | N |
| CF₃ | 3-Cl, 5-Cl | H | CH | O | H | H | N |
| CF₃ | 3-Cl, 5-Cl | H | CH | NMe | H | H | N |
| CF₃ | 3-Cl, 5-Cl | H | N | S | H | H | N |
| CF₃ | 3-Cl, 5-Cl | H | N | O | H | H | N |
| Me | 3-Cl, 4-Cl | H | CH | S | H | H | CH |
| Me | 3-Cl, 4-Cl | H | CH | O | H | H | CH |
| Me | 3-Cl, 4-Cl | H | CH | NMe | H | H | CH |
| Me | 3-Cl, 4-Cl | H | N | S | H | H | CH |
| Me | 3-Cl, 4-Cl | H | N | O | H | H | CH |
| Me | 3-Cl, 5-Cl | H | CH | S | H | H | CH |
| Me | 3-Cl, 5-Cl | H | CH | O | H | H | CH |
| Me | 3-Cl, 5-Cl | H | CH | NMe | H | H | CH |
| Me | 3-Cl, 5-Cl | H | N | S | H | H | CH |
| Me | 3-Cl, 5-Cl | H | N | O | H | H | CH |
| CF₃ | 3-Cl, 4-Cl | H | CH | S | Cl | H | CH |
| CF₃ | 3-Cl, 4-Cl | H | CH | O | Cl | H | CH |
| CF₃ | 3-Cl, 4-Cl | H | CH | NMe | Cl | H | CH |
| CF₃ | 3-Cl, 4-Cl | H | N | S | Cl | H | CH |
| CF₃ | 3-Cl, 4-Cl | H | N | O | Cl | H | CH |
| CF₃ | 3-Cl, 5-Cl | H | CH | S | Cl | H | CH |
| CF₃ | 3-Cl, 5-Cl | H | CH | O | Cl | H | CH |
| CF₃ | 3-Cl, 5-Cl | H | CH | NMe | Cl | H | CH |
| CF₃ | 3-Cl, 5-Cl | H | N | S | Cl | H | CH |
| CF₃ | 3-Cl, 5-Cl | H | N | O | Cl | H | CH |
| CF₃ | 3-Cl, 4-Cl | H | CH | S | Cl | Cl | CH |
| CF₃ | 3-Cl, 4-Cl | H | CH | O | Cl | Cl | CH |
| CF₃ | 3-Cl, 4-Cl | H | CH | NMe | Cl | Cl | CH |
| CF₃ | 3-Cl, 4-Cl | H | N | S | Cl | Cl | CH |
| CF₃ | 3-Cl, 4-Cl | H | N | O | Cl | Cl | CH |
| CF₃ | 3-Cl, 5-Cl | H | CH | S | Cl | Cl | CH |
| CF₃ | 3-Cl, 5-Cl | H | CH | O | Cl | Cl | CH |
| CF₃ | 3-Cl, 5-Cl | H | CH | NMe | Cl | Cl | CH |
| CF₃ | 3-Cl, 5-Cl | H | N | S | Cl | Cl | CH |
| CF₃ | 3-Cl, 5-Cl | H | N | O | Cl | Cl | CH |

TABLE 7

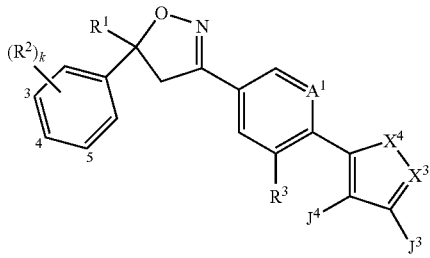

wherein k is 1, 2, 3, 4 or 5.

| R¹ | (R²)ₖ | R³ | X³ | X⁴ | J³ | J⁴ | A³ |
|---|---|---|---|---|---|---|---|
| CF₃ | 3-Cl, 4-Cl | H | CH | S | H | H | CH |
| CF₃ | 3-Cl, 4-Cl | H | CH | O | H | H | CH |
| CF₃ | 3-Cl, 4-Cl | H | CH | NMe | H | H | CH |
| CF₃ | 3-Cl, 4-Cl | H | N | S | H | H | CH |
| CF₃ | 3-Cl, 4-Cl | H | N | O | H | H | CH |
| CF₃ | 3-Cl, 5-Cl | H | CH | S | H | H | CH |
| CF₃ | 3-Cl, 5-Cl | H | CH | O | H | H | CH |
| CF₃ | 3-Cl, 5-Cl | H | CH | NMe | H | H | CH |
| CF₃ | 3-Cl, 5-Cl | H | N | S | H | H | CH |
| CF₃ | 3-Cl, 5-Cl | H | N | O | H | H | CH |
| CF₃ | 3-Cl, 4-Cl | Me | CH | S | H | H | CH |
| CF₃ | 3-Cl, 4-Cl | Me | CH | O | H | H | CH |
| CF₃ | 3-Cl, 4-Cl | Me | CH | NMe | H | H | CH |
| CF₃ | 3-Cl, 4-Cl | Me | N | S | H | H | CH |
| CF₃ | 3-Cl, 4-Cl | Me | N | O | H | H | CH |
| CF₃ | 3-Cl, 5-Cl | Me | CH | S | H | H | CH |
| CF₃ | 3-Cl, 5-Cl | Me | CH | O | H | H | CH |
| CF₃ | 3-Cl, 5-Cl | Me | CH | NMe | H | H | CH |
| CF₃ | 3-Cl, 5-Cl | Me | N | S | H | H | CH |
| CF₃ | 3-Cl, 5-Cl | Me | N | O | H | H | CH |
| CF₃ | 3-Cl, 4-Cl | H | CH | S | H | H | N |
| CF₃ | 3-Cl, 4-Cl | H | CH | O | H | H | N |
| CF₃ | 3-Cl, 4-Cl | H | CH | NMe | H | H | N |
| CF₃ | 3-Cl, 4-Cl | H | N | S | H | H | N |
| CF₃ | 3-Cl, 4-Cl | H | N | O | H | H | N |
| CF₃ | 3-Cl, 5-Cl | H | CH | S | H | H | N |
| CF₃ | 3-Cl, 5-Cl | H | CH | O | H | H | N |
| CF₃ | 3-Cl, 5-Cl | H | CH | NMe | H | H | N |
| CF₃ | 3-Cl, 5-Cl | H | N | S | H | H | N |
| CF₃ | 3-Cl, 5-Cl | H | N | O | H | H | N |
| Me | 3-Cl, 4-Cl | H | CH | S | H | H | CH |
| Me | 3-Cl, 4-Cl | H | CH | O | H | H | CH |
| Me | 3-Cl, 4-Cl | H | CH | NMe | H | H | CH |
| Me | 3-Cl, 4-Cl | H | N | S | H | H | CH |
| Me | 3-Cl, 4-Cl | H | N | O | H | H | CH |
| Me | 3-Cl, 5-Cl | H | CH | S | H | H | CH |
| Me | 3-Cl, 5-Cl | H | CH | O | H | H | CH |
| Me | 3-Cl, 5-Cl | H | CH | NMe | H | H | CH |
| Me | 3-Cl, 5-Cl | H | N | S | H | H | CH |
| Me | 3-Cl, 5-Cl | H | N | O | H | H | CH |
| CF₃ | 3-Cl, 4-Cl | H | CH | S | Cl | H | CH |
| CF₃ | 3-Cl, 4-Cl | H | CH | O | Cl | H | CH |
| CF₃ | 3-Cl, 4-Cl | H | CH | NMe | Cl | H | CH |
| CF₃ | 3-Cl, 4-Cl | H | N | S | Cl | H | CH |
| CF₃ | 3-Cl, 4-Cl | H | N | O | Cl | H | CH |
| CF₃ | 3-Cl, 5-Cl | H | CH | S | Cl | H | CH |
| CF₃ | 3-Cl, 5-Cl | H | CH | O | Cl | H | CH |
| CF₃ | 3-Cl, 5-Cl | H | CH | NMe | Cl | H | CH |
| CF₃ | 3-Cl, 5-Cl | H | N | S | Cl | H | CH |
| CF₃ | 3-Cl, 5-Cl | H | N | O | Cl | H | CH |
| CF₃ | 3-Cl, 4-Cl | H | CH | S | Cl | Cl | CH |
| CF₃ | 3-Cl, 4-Cl | H | CH | O | Cl | Cl | CH |
| CF₃ | 3-Cl, 4-Cl | H | CH | NMe | Cl | Cl | CH |
| CF₃ | 3-Cl, 4-Cl | H | N | S | Cl | Cl | CH |
| CF₃ | 3-Cl, 4-Cl | H | N | O | Cl | Cl | CH |
| CF₃ | 3-Cl, 5-Cl | H | CH | S | Cl | Cl | CH |
| CF₃ | 3-Cl, 5-Cl | H | CH | O | Cl | Cl | CH |
| CF₃ | 3-Cl, 5-Cl | H | CH | NMe | Cl | Cl | CH |
| CF₃ | 3-Cl, 5-Cl | H | N | S | Cl | Cl | CH |
| CF₃ | 3-Cl, 5-Cl | H | N | O | Cl | Cl | CH |

TABLE 8

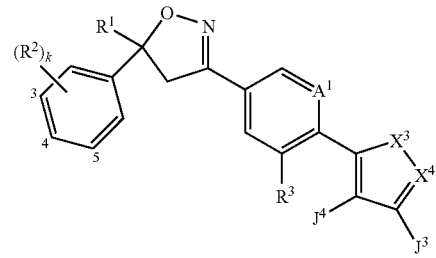

wherein k is 1, 2, 3, 4 or 5.

| R¹ | (R²)ₖ | R³ | X³ | X⁴ | J³ | J⁴ | A³ |
|---|---|---|---|---|---|---|---|
| CF₃ | 3-Cl, 4-Cl | H | CH | S | H | H | CH |
| CF₃ | 3-Cl, 4-Cl | H | CH | O | H | H | CH |
| CF₃ | 3-Cl, 4-Cl | H | CH | NMe | H | H | CH |
| CF₃ | 3-Cl, 4-Cl | H | N | S | H | H | CH |
| CF₃ | 3-Cl, 4-Cl | H | N | O | H | H | CH |
| CF₃ | 3-Cl, 5-Cl | H | CH | S | H | H | CH |
| CF₃ | 3-Cl, 5-Cl | H | CH | O | H | H | CH |
| CF₃ | 3-Cl, 5-Cl | H | CH | NMe | H | H | CH |
| CF₃ | 3-Cl, 5-Cl | H | N | S | H | H | CH |
| CF₃ | 3-Cl, 5-Cl | H | N | O | H | H | CH |
| CF₃ | 3-Cl, 4-Cl | Me | CH | S | H | H | CH |
| CF₃ | 3-Cl, 4-Cl | Me | CH | O | H | H | CH |
| CF₃ | 3-Cl, 4-Cl | Me | CH | NMe | H | H | CH |
| CF₃ | 3-Cl, 4-Cl | Me | N | S | H | H | CH |
| CF₃ | 3-Cl, 4-Cl | Me | N | O | H | H | CH |
| CF₃ | 3-Cl, 5-Cl | Me | CH | S | H | H | CH |
| CF₃ | 3-Cl, 5-Cl | Me | CH | O | H | H | CH |
| CF₃ | 3-Cl, 5-Cl | Me | CH | NMe | H | H | CH |
| CF₃ | 3-Cl, 5-Cl | Me | N | S | H | H | CH |
| CF₃ | 3-Cl, 5-Cl | Me | N | O | H | H | CH |
| CF₃ | 3-Cl, 4-Cl | H | CH | S | H | H | N |
| CF₃ | 3-Cl, 4-Cl | H | CH | O | H | H | N |
| CF₃ | 3-Cl, 4-Cl | H | CH | NMe | H | H | N |
| CF₃ | 3-Cl, 4-Cl | H | N | S | H | H | N |
| CF₃ | 3-Cl, 4-Cl | H | N | O | H | H | N |
| CF₃ | 3-Cl, 5-Cl | H | CH | S | H | H | N |
| CF₃ | 3-Cl, 5-Cl | H | CH | O | H | H | N |
| CF₃ | 3-Cl, 5-Cl | H | CH | NMe | H | H | N |
| CF₃ | 3-Cl, 5-Cl | H | N | S | H | H | N |
| CF₃ | 3-Cl, 5-Cl | H | N | O | H | H | N |
| Me | 3-Cl, 4-Cl | H | CH | S | H | H | CH |
| Me | 3-Cl, 4-Cl | H | CH | O | H | H | CH |
| Me | 3-Cl, 4-Cl | H | CH | NMe | H | H | CH |
| Me | 3-Cl, 4-Cl | H | N | S | H | H | CH |
| Me | 3-Cl, 4-Cl | H | N | O | H | H | CH |
| Me | 3-Cl, 5-Cl | H | CH | S | H | H | CH |
| Me | 3-Cl, 5-Cl | H | CH | O | H | H | CH |
| Me | 3-Cl, 5-Cl | H | CH | NMe | H | H | CH |
| Me | 3-Cl, 5-Cl | H | N | S | H | H | CH |
| Me | 3-Cl, 5-Cl | H | N | O | H | H | CH |
| CF₃ | 3-Cl, 4-Cl | H | CH | S | Cl | H | CH |
| CF₃ | 3-Cl, 4-Cl | H | CH | O | Cl | H | CH |
| CF₃ | 3-Cl, 4-Cl | H | CH | NMe | Cl | H | CH |
| CF₃ | 3-Cl, 4-Cl | H | N | S | Cl | H | CH |
| CF₃ | 3-Cl, 4-Cl | H | N | O | Cl | H | CH |
| CF₃ | 3-Cl, 5-Cl | H | CH | S | Cl | H | CH |
| CF₃ | 3-Cl, 5-Cl | H | CH | O | Cl | H | CH |
| CF₃ | 3-Cl, 5-Cl | H | CH | NMe | Cl | H | CH |
| CF₃ | 3-Cl, 5-Cl | H | N | S | Cl | H | CH |
| CF₃ | 3-Cl, 5-Cl | H | N | O | Cl | H | CH |
| CF₃ | 3-Cl, 4-Cl | H | CH | S | Cl | Cl | CH |
| CF₃ | 3-Cl, 4-Cl | H | CH | O | Cl | Cl | CH |
| CF₃ | 3-Cl, 4-Cl | H | CH | NMe | Cl | Cl | CH |
| CF₃ | 3-Cl, 4-Cl | H | N | S | Cl | Cl | CH |
| CF₃ | 3-Cl, 4-Cl | H | N | O | Cl | Cl | CH |
| CF₃ | 3-Cl, 5-Cl | H | CH | S | Cl | Cl | CH |
| CF₃ | 3-Cl, 5-Cl | H | CH | O | Cl | Cl | CH |
| CF₃ | 3-Cl, 5-Cl | H | CH | NMe | Cl | Cl | CH |
| CF₃ | 3-Cl, 5-Cl | H | N | S | Cl | Cl | CH |
| CF₃ | 3-Cl, 5-Cl | H | N | O | Cl | Cl | CH |

TABLE 9

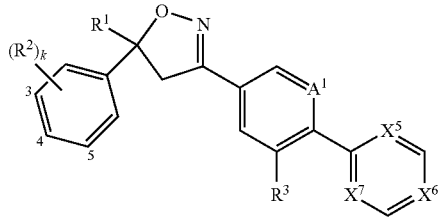

wherein k is 1, 2, 3, 4 or 5.

| R¹ | (R²)ₖ | R³ | A³ | X⁵ | X⁶ | X⁷ |
|---|---|---|---|---|---|---|
| CF₃ | 3-Cl, 4-Cl | H | CH | CH | CH | CH |
| CF₃ | 3-Cl, 4-Cl | H | CH | C—Cl | CH | CH |
| CF₃ | 3-Cl, 4-Cl | H | CH | C—Me | CH | CH |
| CF₃ | 3-Cl, 4-Cl | H | CH | C—F | CH | CH |
| CF₃ | 3-Cl, 4-Cl | H | CH | C—CO₂Me | CH | CH |
| CF₃ | 3-Cl, 4-Cl | H | CH | C—CONHMe | CH | CH |
| CF₃ | 3-Cl, 4-Cl | H | CH | CH | C—Cl | CH |
| CF₃ | 3-Cl, 4-Cl | H | CH | CH | C—Me | CH |
| CF₃ | 3-Cl, 4-Cl | H | CH | CH | C—F | CH |
| CF₃ | 3-Cl, 4-Cl | H | CH | CH | C—CO₂Me | CH |
| CF₃ | 3-Cl, 4-Cl | H | CH | CH | C—CONHMe | CH |
| CF₃ | 3-Cl, 5-Cl | H | CH | CH | CH | CH |
| CF₃ | 3-Cl, 5-Cl | H | CH | C—Cl | CH | CH |
| CF₃ | 3-Cl, 5-Cl | H | CH | C—Me | CH | CH |
| CF₃ | 3-Cl, 5-Cl | H | CH | C—F | CH | CH |
| CF₃ | 3-Cl, 5-Cl | H | CH | C—CO₂Me | CH | CH |
| CF₃ | 3-Cl, 5-Cl | H | CH | C—CONHMe | CH | CH |
| CF₃ | 3-Cl, 5-Cl | H | CH | CH | C—Cl | CH |
| CF₃ | 3-Cl, 5-Cl | H | CH | CH | C—Me | CH |
| CF₃ | 3-Cl, 5-Cl | H | CH | CH | C—F | CH |
| CF₃ | 3-Cl, 5-Cl | H | CH | CH | C—CO₂Me | CH |
| CF₃ | 3-Cl, 5-Cl | H | CH | CH | C—CONHMe | CH |
| CF₃ | 3-Cl, 4-Cl | Me | CH | CH | CH | CH |
| CF₃ | 3-Cl, 4-Cl | Me | CH | C—Cl | CH | CH |
| CF₃ | 3-Cl, 4-Cl | Me | CH | C—Me | CH | CH |
| CF₃ | 3-Cl, 4-Cl | Me | CH | C—F | CH | CH |
| CF₃ | 3-Cl, 4-Cl | Me | CH | C—CO₂Me | CH | CH |
| CF₃ | 3-Cl, 4-Cl | Me | CH | C—CONHMe | CH | CH |
| CF₃ | 3-Cl, 4-Cl | Me | CH | CH | C—Cl | CH |
| CF₃ | 3-Cl, 4-Cl | Me | CH | CH | C—Me | CH |
| CF₃ | 3-Cl, 4-Cl | Me | CH | CH | C—F | CH |
| CF₃ | 3-Cl, 4-Cl | Me | CH | CH | C—CO₂Me | CH |
| CF₃ | 3-Cl, 4-Cl | Me | CH | CH | C—CONHMe | CH |
| CF₃ | 3-Cl, 5-Cl | Me | CH | CH | CH | CH |
| CF₃ | 3-Cl, 5-Cl | Me | CH | C—Cl | CH | CH |
| CF₃ | 3-Cl, 5-Cl | Me | CH | C—Me | CH | CH |
| CF₃ | 3-Cl, 5-Cl | Me | CH | C—F | CH | CH |
| CF₃ | 3-Cl, 5-Cl | Me | CH | C—CO₂Me | CH | CH |
| CF₃ | 3-Cl, 5-Cl | Me | CH | C—CONHMe | CH | CH |
| CF₃ | 3-Cl, 5-Cl | Me | CH | CH | C—Cl | CH |
| CF₃ | 3-Cl, 5-Cl | Me | CH | CH | C—Me | CH |
| CF₃ | 3-Cl, 5-Cl | Me | CH | CH | C—F | CH |
| CF₃ | 3-Cl, 5-Cl | Me | CH | CH | C—CO₂Me | CH |
| CF₃ | 3-Cl, 5-Cl | Me | CH | CH | C—CONHMe | CH |
| CF₃ | 3-Cl, 4-Cl | H | CH | N | CH | CH |
| CF₃ | 3-Cl, 4-Cl | H | CH | CH | N | CH |
| CF₃ | 3-Cl, 4-Cl | Me | CH | N | CH | CH |
| CF₃ | 3-Cl, 4-Cl | Me | CH | CH | N | CH |
| CF₃ | 3-Cl, 4-Cl | H | CH | N | CH | C—Cl |
| CF₃ | 3-Cl, 4-Cl | H | CH | CH | N | C—Cl |
| CF₃ | 3-Cl, 4-Cl | Me | CH | N | CH | C—Cl |
| CF₃ | 3-Cl, 4-Cl | Me | CH | CH | N | C—Cl |
| CF₃ | 3-Cl, 4-Cl | H | CH | CH | C—Cl | N |
| CF₃ | 3-Cl, 4-Cl | Me | CH | CH | C—Cl | N |
| CF₃ | 3-Cl, 5-Cl | H | CH | N | CH | CH |
| CF₃ | 3-Cl, 5-Cl | H | CH | CH | N | CH |
| CF₃ | 3-Cl, 5-Cl | Me | CH | N | CH | CH |
| CF₃ | 3-Cl, 5-Cl | Me | CH | CH | N | CH |
| CF₃ | 3-Cl, 5-Cl | H | CH | N | CH | C—Cl |
| CF₃ | 3-Cl, 5-Cl | H | CH | CH | N | C—Cl |
| CF₃ | 3-Cl, 5-Cl | H | CH | CH | C—Cl | N |
| CF₃ | 3-Cl, 5-Cl | Me | CH | N | CH | C—Cl |

TABLE 9-continued

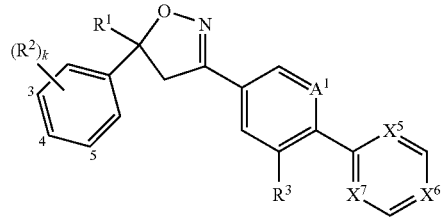

wherein k is 1, 2, 3, 4 or 5.

| R¹ | (R²)ₖ | R³ | A³ | X⁵ | X⁶ | X⁷ |
|---|---|---|---|---|---|---|
| CF₃ | 3-Cl, 5-Cl | Me | CH | CH | N | C—Cl |
| CF₃ | 3-Cl, 5-Cl | Me | CH | CH | C—Cl | N |

TABLE 10

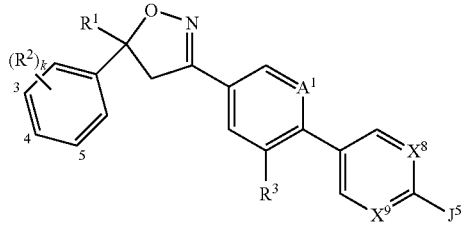

wherein k is 1, 2, 3, 4 or 5.

| R¹ | (R²)ₖ | R³ | A³ | X⁸ | X⁹ | J⁵ |
|---|---|---|---|---|---|---|
| CF₃ | 3-Cl, 4-Cl | H | CH | N | CH | H |
| CF₃ | 3-Cl, 4-Cl | H | CH | N | N | H |
| CF₃ | 3-Cl, 4-Cl | H | CH | N | C—Cl | H |
| CF₃ | 3-Cl, 4-Cl | Me | CH | N | CH | H |
| CF₃ | 3-Cl, 4-Cl | Me | CH | N | N | H |
| CF₃ | 3-Cl, 4-Cl | Me | CH | N | C—Cl | H |
| CF₃ | 3-Cl, 4-Cl | H | N | N | CH | H |
| CF₃ | 3-Cl, 4-Cl | H | N | N | C—Cl | H |
| CF₃ | 3-Cl, 4-Cl | Me | N | N | CH | H |
| CF₃ | 3-Cl, 4-Cl | Me | N | N | N | H |
| CF₃ | 3-Cl, 4-Cl | Me | N | N | C—Cl | H |
| CF₃ | 3-Cl, 5-Cl | H | CH | N | CH | H |
| CF₃ | 3-Cl, 5-Cl | H | CH | N | N | H |
| CF₃ | 3-Cl, 5-Cl | H | CH | N | C—Cl | H |
| CF₃ | 3-Cl, 5-Cl | Me | CH | N | CH | H |
| CF₃ | 3-Cl, 5-Cl | Me | CH | N | N | H |
| CF₃ | 3-Cl, 5-Cl | Me | CH | N | C—Cl | H |
| CF₃ | 3-Cl, 5-Cl | H | N | N | CH | H |
| CF₃ | 3-Cl, 5-Cl | H | N | N | N | H |
| CF₃ | 3-Cl, 5-Cl | H | N | N | C—Cl | H |
| CF₃ | 3-Cl, 5-Cl | Me | N | N | CH | H |
| CF₃ | 3-Cl, 5-Cl | Me | N | N | N | H |
| CF₃ | 3-Cl, 5-Cl | Me | N | N | C—Cl | H |
| CF₃ | 3-Cl, 4-Cl | H | CH | N | CH | Cl |
| CF₃ | 3-Cl, 4-Cl | H | CH | N | N | Cl |
| CF₃ | 3-Cl, 4-Cl | H | CH | N | C—Cl | Cl |
| CF₃ | 3-Cl, 4-Cl | Me | CH | N | CH | Cl |
| CF₃ | 3-Cl, 4-Cl | Me | CH | N | N | Cl |
| CF₃ | 3-Cl, 4-Cl | Me | CH | N | C—Cl | Cl |
| CF₃ | 3-Cl, 4-Cl | H | N | N | CH | Cl |
| CF₃ | 3-Cl, 4-Cl | H | N | N | N | Cl |
| CF₃ | 3-Cl, 4-Cl | H | N | N | C—Cl | Cl |
| CF₃ | 3-Cl, 4-Cl | Me | N | N | CH | Cl |
| CF₃ | 3-Cl, 4-Cl | Me | N | N | N | Cl |
| CF₃ | 3-Cl, 4-Cl | Me | N | N | C—Cl | Cl |
| CF₃ | 3-Cl, 5-Cl | H | CH | N | CH | Cl |
| CF₃ | 3-Cl, 5-Cl | H | CH | N | N | Cl |
| CF₃ | 3-Cl, 5-Cl | H | CH | N | C—Cl | Cl |
| CF₃ | 3-Cl, 5-Cl | Me | CH | N | CH | Cl |
| CF₃ | 3-Cl, 5-Cl | Me | CH | N | N | Cl |

TABLE 10-continued wherein k is 1, 2, 3, 4 or 5.

| R¹ | (R²)ₖ | R³ | A³ | X⁸ | X⁹ | J⁵ |
|---|---|---|---|---|---|---|
| CF₃ | 3-Cl, 5-Cl | Me | CH | N | C—Cl | Cl |
| CF₃ | 3-Cl, 5-Cl | H | N | N | CH | Cl |
| CF₃ | 3-Cl, 5-Cl | H | N | N | N | Cl |
| CF₃ | 3-Cl, 5-Cl | H | N | N | C—Cl | Cl |
| CF₃ | 3-Cl, 5-Cl | Me | N | N | CH | Cl |
| CF₃ | 3-Cl, 5-Cl | Me | N | N | N | Cl |
| CF₃ | 3-Cl, 5-Cl | Me | N | N | C—Cl | Cl |
| CF₃ | 3-Cl, 4-Cl | H | CH | N | CH | CF₃ |
| CF₃ | 3-Cl, 4-Cl | H | CH | N | N | CF₃ |
| CF₃ | 3-Cl, 4-Cl | H | CH | N | C—Cl | CF₃ |
| CF₃ | 3-Cl, 4-Cl | Me | CH | N | CH | CF₃ |
| CF₃ | 3-Cl, 4-Cl | Me | CH | N | N | CF₃ |
| CF₃ | 3-Cl, 4-Cl | Me | CH | N | C—Cl | CF₃ |
| CF₃ | 3-Cl, 4-Cl | H | N | N | CH | CF₃ |
| CF₃ | 3-Cl, 4-Cl | H | N | N | N | CF₃ |
| CF₃ | 3-Cl, 4-Cl | H | N | N | C—Cl | CF₃ |
| CF₃ | 3-Cl, 4-Cl | Me | N | N | CH | CF₃ |
| CF₃ | 3-Cl, 4-Cl | Me | N | N | N | CF₃ |
| CF₃ | 3-Cl, 4-Cl | Me | N | N | C—Cl | CF₃ |
| CF₃ | 3-Cl, 5-Cl | H | CH | N | CH | CF₃ |
| CF₃ | 3-Cl, 5-Cl | H | CH | N | N | CF₃ |
| CF₃ | 3-Cl, 5-Cl | H | CH | N | C—Cl | CF₃ |
| CF₃ | 3-Cl, 5-Cl | Me | CH | N | CH | CF₃ |
| CF₃ | 3-Cl, 5-Cl | Me | CH | N | N | CF₃ |
| CF₃ | 3-Cl, 5-Cl | Me | CH | N | C—Cl | CF₃ |
| CF₃ | 3-Cl, 5-Cl | H | N | N | CH | CF₃ |
| CF₃ | 3-Cl, 5-Cl | H | N | N | N | CF₃ |
| CF₃ | 3-Cl, 5-Cl | H | N | N | C—Cl | CF₃ |
| CF₃ | 3-Cl, 5-Cl | Me | N | N | CH | CF₃ |
| CF₃ | 3-Cl, 5-Cl | Me | N | N | N | CF₃ |
| CF₃ | 3-Cl, 5-Cl | Me | N | N | C—Cl | CF₃ |

TABLE 11

| B¹ | B² | B³ | R³ | A³ |
|---|---|---|---|---|
| C—Cl | CH | CH | Me | CH |
| C—Cl | CH | C—Cl | Me | CH |
| C—Br | CH | CH | Me | CH |
| C—Br | CH | C—Br | Me | CH |
| C—Cl | CH | CH | Me | N |
| C—Cl | CH | C—Cl | Me | N |
| C—Br | CH | CH | Me | N |
| C—Br | CH | C—Br | Me | N |
| C—Cl | CH | CH | F | CH |
| C—Cl | CH | C—Cl | F | CH |
| C—Br | CH | CH | F | CH |
| C—Br | CH | C—Br | F | CH |
| C—Cl | CH | CH | F | N |
| C—Cl | CH | C—Cl | F | N |

TABLE 11-continued

| B¹ | B² | B³ | R³ | A³ |
|---|---|---|---|---|
| C—Br | CH | CH | F | N |
| C—Br | CH | C—Br | F | N |
| C—Cl | CH | CH | Cl | CH |
| C—Cl | CH | C—Cl | Cl | CH |
| C—Br | CH | CH | Cl | CH |
| C—Br | CH | C—Br | Cl | CH |
| C—Cl | CH | CH | Cl | N |
| C—Cl | CH | C—Cl | Cl | N |
| C—Br | CH | CH | Cl | N |
| C—Br | CH | C—Br | Cl | N |
| C—Cl | CH | CH | Br | CH |
| C—Cl | CH | C—Cl | Br | CH |
| C—Br | CH | CH | Br | CH |
| C—Br | CH | C—Br | Br | CH |
| C—Cl | CH | CH | Br | N |
| C—Cl | CH | C—Cl | Br | N |
| C—Br | CH | CH | Br | N |
| C—Br | CH | C—Br | Br | N |
| C—Cl | CH | CH | I | CH |
| C—Cl | CH | C—Cl | I | CH |
| C—Br | CH | CH | I | CH |
| C—Br | CH | C—Br | I | CH |
| C—Cl | CH | CH | I | N |
| C—Cl | CH | C—Cl | I | N |
| C—Br | CH | CH | I | N |
| C—Br | CH | C—Br | I | N |
| C—Cl | CH | CH | —CN | CH |
| C—Cl | CH | C—Cl | —CN | CH |
| C—Br | CH | CH | —CN | CH |
| C—Br | CH | C—Br | —CN | CH |
| C—Cl | CH | CH | —CN | N |
| C—Cl | CH | C—Cl | —CN | N |
| C—Br | CH | CH | —CN | N |
| C—Br | CH | C—Br | —CN | N |
| C—Cl | CH | CH | CF₃ | CH |
| C—Cl | CH | C—Cl | CF₃ | CH |
| C—Br | CH | CH | CF₃ | CH |
| C—Br | CH | C—Br | CF₃ | CH |
| C—Cl | CH | CH | CF₃ | N |
| C—Cl | CH | C—Cl | CF₃ | N |
| C—Br | CH | CH | CF₃ | N |
| C—Br | CH | C—Br | CF₃ | N |
| C—Cl | CH | CH | OCF₃ | CH |
| C—Cl | CH | C—Cl | OCF₃ | CH |
| C—Br | CH | CH | OCF₃ | CH |
| C—Br | CH | C—Br | OCF₃ | CH |
| C—Cl | CH | CH | OCF₃ | N |
| C—Cl | CH | C—Cl | OCF₃ | N |
| C—Br | CH | CH | OCF₃ | N |
| C—Br | CH | C—Br | OCF₃ | N |
| C—Cl | CH | CH | OMe | CH |
| C—Cl | CH | C—Cl | OMe | CH |
| C—Br | CH | CH | OMe | CH |
| C—Br | CH | C—Br | OMe | CH |
| C—Cl | CH | CH | OMe | N |
| C—Cl | CH | C—Cl | OMe | N |
| C—Br | CH | CH | OMe | N |
| C—Br | CH | C—Br | OMe | N |
| C—Cl | N | CH | Me | CH |
| C—Cl | N | C—Cl | Me | CH |
| C—Br | N | CH | Me | CH |
| C—Br | N | C—Br | Me | CH |
| C—Cl | N | CH | F | CH |
| C—Cl | N | C—Cl | F | CH |
| C—Br | N | CH | F | CH |

TABLE 11-continued

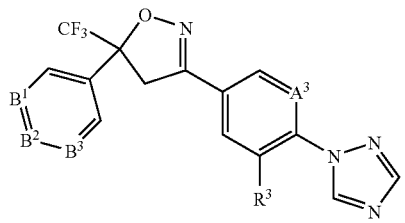

| B¹ | B² | B³ | R³ | A³ |
|---|---|---|---|---|
| C—Br | N | C—Br | F | CH |
| C—Cl | N | CH | Cl | CH |
| C—Cl | N | C—Cl | Cl | CH |
| C—Br | N | CH | Cl | CH |
| C—Br | N | C—Br | Cl | CH |
| C—Cl | N | CH | Br | CH |
| C—Cl | N | C—Cl | Br | CH |
| C—Br | N | CH | Br | CH |
| C—Br | N | C—Br | Br | CH |
| C—Cl | N | CH | I | CH |
| C—Cl | N | C—Cl | I | CH |
| C—Br | N | CH | I | CH |
| C—Br | N | C—Br | I | CH |
| C—Cl | N | CH | —CN | CH |
| C—Cl | N | C—Cl | —CN | CH |
| C—Br | N | CH | —CN | CH |
| C—Br | N | C—Br | —CN | CH |
| C—Cl | N | CH | CF₃ | CH |
| C—Cl | N | C—Cl | CF₃ | CH |
| C—Br | N | CH | CF₃ | CH |
| C—Br | N | C—Br | CF₃ | CH |
| C—Cl | N | CH | OCF₃ | CH |
| C—Cl | N | C—Cl | OCF₃ | CH |
| C—Br | N | CH | OCF₃ | CH |
| C—Br | N | C—Br | OCF₃ | CH |
| C—Cl | N | CH | OMe | CH |
| C—Cl | N | C—Cl | OMe | CH |
| C—Br | N | CH | OMe | CH |
| C—Br | N | C—Br | OMe | CH |
| C—Cl | C—Cl | CH | Me | CH |
| C—Cl | C—Cl | C—Cl | Me | CH |
| C—Br | C—Cl | CH | Me | CH |
| C—Br | C—Cl | C—Br | Me | CH |
| C—Cl | C—Cl | CH | Me | N |
| C—Cl | C—Cl | C—Cl | Me | N |
| C—Br | C—Cl | CH | Me | N |
| C—Br | C—Cl | C—Br | Me | N |
| C—Cl | C—Cl | CH | F | CH |
| C—Cl | C—Cl | C—Cl | F | CH |
| C—Br | C—Cl | CH | F | CH |
| C—Br | C—Cl | C—Br | F | CH |
| C—Cl | C—Cl | CH | F | N |
| C—Cl | C—Cl | C—Cl | F | N |
| C—Br | C—Cl | CH | F | N |
| C—Br | C—Cl | C—Br | F | N |
| C—Cl | C—Cl | CH | Cl | CH |
| C—Cl | C—Cl | C—Cl | Cl | CH |
| C—Br | C—Cl | CH | Cl | CH |
| C—Br | C—Cl | C—Br | Cl | CH |
| C—Cl | C—Cl | CH | Cl | N |
| C—Cl | C—Cl | C—Cl | Cl | N |
| C—Br | C—Cl | CH | Cl | N |
| C—Br | C—Cl | C—Br | Cl | N |
| C—Cl | C—Cl | CH | Br | CH |
| C—Cl | C—Cl | C—Cl | Br | CH |
| C—Br | C—Cl | CH | Br | CH |
| C—Br | C—Cl | C—Br | Br | CH |
| C—Cl | C—Cl | CH | Br | N |
| C—Cl | C—Cl | C—Cl | Br | N |
| C—Br | C—Cl | CH | Br | N |
| C—Br | C—Cl | C—Br | Br | N |
| C—Cl | C—Cl | CH | I | CH |
| C—Cl | C—Cl | C—Cl | I | CH |
| C—Br | C—Cl | CH | I | CH |
| C—Br | C—Cl | C—Br | I | CH |

TABLE 11-continued

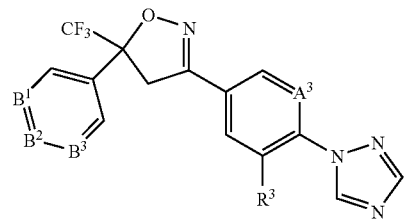

| B¹ | B² | B³ | R³ | A³ |
|---|---|---|---|---|
| C—Cl | C—Cl | CH | I | N |
| C—Cl | C—Cl | C—Cl | I | N |
| C—Br | C—Cl | CH | I | N |
| C—Br | C—Cl | C—Br | I | N |
| C—Cl | C—Cl | CH | —CN | CH |
| C—Cl | C—Cl | C—Cl | —CN | CH |
| C—Br | C—Cl | CH | —CN | CH |
| C—Br | C—Cl | C—Br | —CN | CH |
| C—Cl | C—Cl | CH | —CN | N |
| C—Cl | C—Cl | C—Cl | —CN | N |
| C—Br | C—Cl | CH | —CN | N |
| C—Br | C—Cl | C—Br | —CN | N |
| C—Cl | C—Cl | CH | CF₃ | CH |
| C—Cl | C—Cl | C—Cl | CF₃ | CH |
| C—Br | C—Cl | CH | CF₃ | CH |
| C—Br | C—Cl | C—Br | CF₃ | CH |
| C—Cl | C—Cl | CH | CF₃ | N |
| C—Cl | C—Cl | C—Cl | CF₃ | N |
| C—Br | C—Cl | CH | CF₃ | N |
| C—Br | C—Cl | C—Br | CF₃ | N |
| C—Cl | C—Cl | CH | OCF₃ | CH |
| C—Cl | C—Cl | C—Cl | OCF₃ | CH |
| C—Br | C—Cl | CH | OCF₃ | CH |
| C—Br | C—Cl | C—Br | OCF₃ | CH |
| C—Cl | C—Cl | CH | OCF₃ | N |
| C—Cl | C—Cl | C—Cl | OCF₃ | N |
| C—Br | C—Cl | CH | OCF₃ | N |
| C—Br | C—Cl | C—Br | OCF₃ | N |
| C—Cl | C—Cl | CH | OMe | CH |
| C—Cl | C—Cl | C—Cl | OMe | CH |
| C—Br | C—Cl | CH | OMe | CH |
| C—Br | C—Cl | C—Br | OMe | CH |
| C—Cl | C—Cl | CH | OMe | N |
| C—Cl | C—Cl | C—Cl | OMe | N |
| C—Br | C—Cl | CH | OMe | N |
| C—Br | C—Cl | C—Br | OMe | N |
| C—Cl | N | CH | Me | N |
| C—Cl | N | C—Cl | Me | N |
| C—Br | N | CH | Me | N |
| C—Br | N | C—Br | Me | N |
| C—Cl | N | CH | F | N |
| C—Cl | N | C—Cl | F | N |
| C—Br | N | CH | F | N |
| C—Br | N | C—Br | F | N |
| C—Cl | N | CH | Cl | N |
| C—Cl | N | C—Cl | Cl | N |
| C—Br | N | CH | Cl | N |
| C—Br | N | C—Br | Cl | N |
| C—Cl | N | CH | Br | N |
| C—Cl | N | C—Cl | Br | N |
| C—Br | N | CH | Br | N |
| C—Br | N | C—Br | Br | N |
| C—Cl | N | CH | I | N |
| C—Cl | N | C—Cl | I | N |
| C—Br | N | CH | I | N |
| C—Br | N | C—Br | I | N |
| C—Cl | N | CH | —CN | N |
| C—Cl | N | C—Cl | —CN | N |
| C—Br | N | CH | —CN | N |
| C—Br | N | C—Br | —CN | N |
| C—Cl | N | CH | CF₃ | N |
| C—Cl | N | C—Cl | CF₃ | N |
| C—Br | N | CH | CF₃ | N |
| C—Br | N | C—Br | CF₃ | N |
| C—Cl | N | CH | OCF₃ | N |

TABLE 11-continued structure: CF$_3$ on isoxazoline, B$^1$/B$^2$/B$^3$ aromatic ring, A$^3$ pyridine/phenyl with R$^3$ and 1,2,4-triazole substituent

| B$^1$ | B$^2$ | B$^3$ | R$^3$ | A$^3$ |
|---|---|---|---|---|
| C—Cl | N | C—Cl | OCF$_3$ | N |
| C—Br | N | CH | OCF$_3$ | N |
| C—Br | N | C—Br | OCF$_3$ | N |
| C—Cl | N | CH | OMe | N |
| C—Cl | N | C—Cl | OMe | N |
| C—Br | N | CH | OMe | N |
| C—Br | N | C—Br | OMe | N |

TABLE 12 structure with (R$^2$)$_k$ phenyl, CF$_3$-isoxazoline, A$^3$ ring, R$^3$, S(O)$_p$—R$^{25}$ wherein k is 1, 2, 3, 4 or 5.

| (R$^2$)$_k$ | R$^3$ | A$^3$ | p | R$^{25}$ |
|---|---|---|---|---|
| 3-Cl, 4-Cl | H | CH | 0 | Me |
| 3-Cl, 4-Cl | H | CH | 0 | CH$_2$F |
| 3-Cl, 4-Cl | H | CH | 0 | CHF$_2$ |
| 3-Cl, 4-Cl | H | CH | 0 | Et |
| 3-Cl, 4-Cl | H | CH | 0 | CH$_2$CF$_3$ |
| 3-Cl, 4-Cl | H | CH | 0 | CH$_2$CN |
| 3-Cl, 4-Cl | H | CH | 0 | n-Pr |
| 3-Cl, 4-Cl | H | CH | 0 | i-Pr |
| 3-Cl, 4-Cl | H | CH | 0 | CH$_2$(2-Py) |
| 3-Cl, 4-Cl | H | CH | 0 | c-Pr |
| 3-Cl, 4-Cl | H | CH | 0 | CH$_2$(c-Pr) |
| 3-Cl, 4-Cl | H | CH | 0 | CH$_2$C═CH$_2$ |
| 3-Cl, 4-Cl | H | CH | 0 | CH$_2$C≡CH |
| 3-Cl, 4-Cl | Me | CH | 0 | Me |
| 3-Cl, 4-Cl | Me | CH | 0 | CH$_2$F |
| 3-Cl, 4-Cl | Me | CH | 0 | CHF$_2$ |
| 3-Cl, 4-Cl | Me | CH | 0 | Et |
| 3-Cl, 4-Cl | Me | CH | 0 | CH$_2$CF$_3$ |
| 3-Cl, 4-Cl | Me | CH | 0 | CH$_2$CN |
| 3-Cl, 4-Cl | Me | CH | 0 | n-Pr |
| 3-Cl, 4-Cl | Me | CH | 0 | i-Pr |
| 3-Cl, 4-Cl | Me | CH | 0 | CH$_2$(2-Py) |
| 3-Cl, 4-Cl | Me | CH | 0 | c-Pr |
| 3-Cl, 4-Cl | Me | CH | 0 | CH$_2$(c-Pr) |
| 3-Cl, 4-Cl | Me | CH | 0 | CH$_2$C═CH$_2$ |
| 3-Cl, 4-Cl | Me | CH | 0 | CH$_2$C≡CH |
| 3-Cl, 4-Cl | Cl | CH | 0 | Me |
| 3-Cl, 4-Cl | Cl | CH | 0 | CH$_2$F |
| 3-Cl, 4-Cl | Cl | CH | 0 | CHF$_2$ |
| 3-Cl, 4-Cl | Cl | CH | 0 | Et |
| 3-Cl, 4-Cl | Cl | CH | 0 | CH$_2$CF$_3$ |
| 3-Cl, 4-Cl | Cl | CH | 0 | CH$_2$CN |
| 3-Cl, 4-Cl | Cl | CH | 0 | n-Pr |
| 3-Cl, 4-Cl | Cl | CH | 0 | i-Pr |
| 3-Cl, 4-Cl | Cl | CH | 0 | CH$_2$(2-Py) |
| 3-Cl, 4-Cl | Cl | CH | 0 | c-Pr |
| 3-Cl, 4-Cl | Cl | CH | 0 | CH$_2$(c-Pr) |
| 3-Cl, 4-Cl | Cl | CH | 0 | CH$_2$C═CH$_2$ |

TABLE 12-continued wherein k is 1, 2, 3, 4 or 5.

| (R$^2$)$_k$ | R$^3$ | A$^3$ | p | R$^{25}$ |
|---|---|---|---|---|
| 3-Cl, 4-Cl | Cl | CH | 0 | CH$_2$C≡CH |
| 3-Cl, 5-Cl | H | CH | 1 | Me |
| 3-Cl, 5-Cl | H | CH | 1 | CH$_2$F |
| 3-Cl, 5-Cl | H | CH | 1 | CHF$_2$ |
| 3-Cl, 5-Cl | H | CH | 1 | Et |
| 3-Cl, 5-Cl | H | CH | 1 | CH$_2$CF$_3$ |
| 3-Cl, 5-Cl | H | CH | 1 | CH$_2$CN |
| 3-Cl, 5-Cl | H | CH | 1 | n-Pr |
| 3-Cl, 5-Cl | H | CH | 1 | i-Pr |
| 3-Cl, 5-Cl | H | CH | 1 | CH$_2$(2-Py) |
| 3-Cl, 5-Cl | H | CH | 1 | c-Pr |
| 3-Cl, 5-Cl | H | CH | 1 | CH$_2$(c-Pr) |
| 3-Cl, 5-Cl | H | CH | 1 | CH$_2$C═CH$_2$ |
| 3-Cl, 5-Cl | H | CH | 1 | CH$_2$C≡CH |
| 3-Cl, 5-Cl | Me | CH | 1 | Me |
| 3-Cl, 5-Cl | Me | CH | 1 | CH$_2$F |
| 3-Cl, 5-Cl | Me | CH | 1 | CHF$_2$ |
| 3-Cl, 5-Cl | Me | CH | 1 | Et |
| 3-Cl, 5-Cl | Me | CH | 1 | CH$_2$CF$_3$ |
| 3-Cl, 5-Cl | Me | CH | 1 | CH$_2$CN |
| 3-Cl, 5-Cl | Me | CH | 1 | n-Pr |
| 3-Cl, 5-Cl | Me | CH | 1 | i-Pr |
| 3-Cl, 5-Cl | Me | CH | 1 | CH$_2$(2-Py) |
| 3-Cl, 5-Cl | Me | CH | 1 | c-Pr |
| 3-Cl, 5-Cl | Me | CH | 1 | CH$_2$(c-Pr) |
| 3-Cl, 5-Cl | Me | CH | 1 | CH$_2$C═CH$_2$ |
| 3-Cl, 5-Cl | Me | CH | 1 | CH$_2$C≡CH |
| 3-Cl, 5-Cl | Cl | CH | 1 | Me |
| 3-Cl, 5-Cl | Cl | CH | 1 | CH$_2$F |
| 3-Cl, 5-Cl | Cl | CH | 1 | CHF$_2$ |
| 3-Cl, 5-Cl | Cl | CH | 1 | Et |
| 3-Cl, 5-Cl | Cl | CH | 1 | CH$_2$CF$_3$ |
| 3-CL, 5-Cl | Cl | CH | 1 | CH$_2$CN |
| 3-Cl, 5-Cl | Cl | CH | 1 | n-Pr |
| 3-Cl, 5-Cl | Cl | CH | 1 | i-Pr |
| 3-Cl, 5-Cl | Cl | CH | 1 | CH$_2$(2-Py) |
| 3-Cl, 5-Cl | Cl | CH | 1 | c-Pr |
| 3-Cl, 5-Cl | Cl | CH | 1 | CH$_2$(c-Pr) |
| 3-Cl, 5-Cl | Cl | CH | 1 | CH$_2$C═CH$_2$ |
| 3-Cl, 5-Cl | Cl | CH | 1 | CH$_2$C≡CH |
| 3-Cl, 5-Cl | OMe | CH | 0 | Me |
| 3-Cl, 5-Cl | OMe | CH | 0 | CH$_2$F |
| 3-Cl, 5-Cl | OMe | CH | 0 | CHF$_2$ |
| 3-Cl, 5-Cl | OMe | CH | 0 | Et |
| 3-Cl, 5-Cl | OMe | CH | 0 | CH$_2$CF$_3$ |
| 3-Cl, 5-Cl | OMe | CH | 0 | CH$_2$CN |
| 3-Cl, 5-Cl | OMe | CH | 0 | n-Pr |
| 3-Cl, 5-Cl | OMe | CH | 0 | i-Pr |
| 3-Cl, 5-Cl | OMe | CH | 0 | CH$_2$(2-Py) |
| 3-Cl, 5-Cl | OMe | CH | 0 | c-Pr |
| 3-Cl, 5-Cl | OMe | CH | 0 | CH$_2$(c-Pr) |
| 3-Cl, 5-Cl | OMe | CH | 0 | CH$_2$C═CH$_2$ |
| 3-Cl, 5-Cl | OMe | CH | 0 | CH$_2$C≡CH |
| 3-Cl, 5-Cl | OMe | CH | 1 | Me |
| 3-Cl, 5-Cl | OMe | CH | 1 | CH$_2$F |
| 3-Cl, 5-Cl | OMe | CH | 1 | CHF$_2$ |
| 3-Cl, 5-Cl | OMe | CH | 1 | Et |
| 3-Cl, 5-Cl | OMe | CH | 1 | CH$_2$CF$_3$ |
| 3-Cl, 5-Cl | OMe | CH | 1 | CH$_2$CN |
| 3-Cl, 5-Cl | OMe | CH | 1 | n-Pr |
| 3-Cl, 5-Cl | OMe | CH | 1 | i-Pr |
| 3-Cl, 5-Cl | OMe | CH | 1 | CH$_2$(2-Py) |
| 3-Cl, 5-Cl | OMe | CH | 1 | c-Pr |
| 3-Cl, 5-Cl | OMe | CH | 1 | CH$_2$(c-Pr) |

TABLE 12-continued

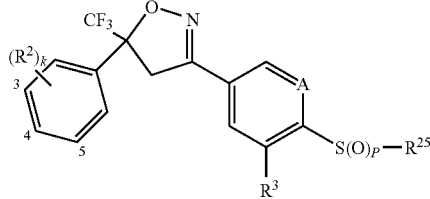
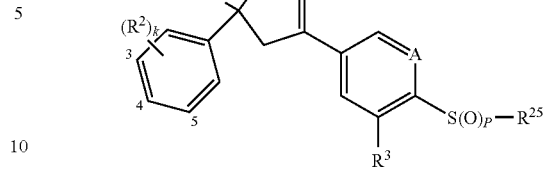

wherein k is 1, 2, 3, 4 or 5.

| (R²)ₖ | R³ | A³ | p | R²⁵ |
|---|---|---|---|---|
| 3-Cl, 5-Cl | OMe | CH | 1 | CH₂C═CH₂ |
| 3-Cl, 5-Cl | OMe | CH | 1 | CH₂C≡CH |
| 3-Cl, 5-Cl | OMe | CH | 2 | Me |
| 3-Cl, 5-Cl | OMe | CH | 2 | CH₂F |
| 3-Cl, 5-Cl | OMe | CH | 2 | CHF₂ |
| 3-Cl, 5-Cl | OMe | CH | 2 | Et |
| 3-Cl, 5-Cl | OMe | CH | 2 | CH₂CF₃ |
| 3-Cl, 5-Cl | OMe | CH | 2 | CH₂CN |
| 3-Cl, 5-Cl | OMe | CH | 2 | n-Pr |
| 3-Cl, 5-Cl | OMe | CH | 2 | i-Pr |
| 3-Cl, 5-Cl | OMe | CH | 2 | CH₂(2-Py) |
| 3-Cl, 5-Cl | OMe | CH | 2 | c-Pr |
| 3-Cl, 5-Cl | OMe | CH | 2 | CH₂(c-Pr) |
| 3-Cl, 5-Cl | OMe | CH | 2 | CH₂C═CH₂ |
| 3-Cl, 5-Cl | OMe | CH | 2 | CH₂C≡CH |
| 3-Cl, 5-Cl | CN | CH | 0 | Me |
| 3-Cl, 5-Cl | CN | CH | 0 | CH₂F |
| 3-Cl, 5-Cl | CN | CH | 0 | CHF₂ |
| 3-Cl, 5-Cl | CN | CH | 0 | Et |
| 3-Cl, 5-Cl | CN | CH | 0 | CH₂CF₃ |
| 3-Cl, 5-Cl | CN | CH | 0 | CH₂CN |
| 3-Cl, 5-Cl | CN | CH | 0 | n-Pr |
| 3-Cl, 5-Cl | CN | CH | 0 | i-Pr |
| 3-Cl, 5-Cl | CN | CH | 0 | CH₂(2-Py) |
| 3-Cl, 5-Cl | CN | CH | 0 | c-Pr |
| 3-Cl, 5-Cl | CN | CH | 0 | CH₂(c-Pr) |
| 3-Cl, 5-Cl | CN | CH | 0 | CH₂C═CH₂ |
| 3-Cl, 5-Cl | CN | CH | 0 | CH₂C≡CH |
| 3-Cl, 5-Cl | CN | CH | 2 | Me |
| 3-Cl, 5-Cl | CN | CH | 2 | CH₂F |
| 3-Cl, 5-Cl | CN | CH | 2 | CHF₂ |
| 3-Cl, 5-Cl | CN | CH | 2 | Et |
| 3-Cl, 5-Cl | CN | CH | 2 | CH₂CF₃ |
| 3-Cl, 5-Cl | CN | CH | 2 | CH₂CN |
| 3-Cl, 5-Cl | CN | CH | 2 | n-Pr |
| 3-Cl, 5-Cl | H | N | 0 | Me |
| 3-Cl, 5-Cl | H | N | 0 | Et |
| 3-Cl, 5-Cl | H | N | 0 | CH₂CF₃ |
| 3-Cl, 5-Cl | H | N | 0 | CH₂CN |
| 3-Cl, 5-Cl | H | N | 0 | n-Pr |
| 3-Cl, 5-Cl | H | N | 0 | i-Pr |
| 3-Cl, 5-Cl | H | N | 0 | CH₂(2-Py) |
| 3-Cl, 5-Cl | Me | N | 0 | Me |
| 3-Cl, 5-Cl | Me | N | 0 | Et |
| 3-Cl, 5-Cl | Me | N | 0 | CH₂CF₃ |
| 3-Cl, 5-Cl | Me | N | 0 | CH₂CN |
| 3-Cl, 5-Cl | Me | N | 0 | n-Pr |
| 3-Cl, 5-Cl | Me | N | 0 | i-Pr |
| 3-Cl, 5-Cl | Me | N | 0 | CH₂(2-Py) |
| 3-Cl, 5-Cl | CF₃ | N | 0 | Me |
| 3-Cl, 5-Cl | CF₃ | N | 0 | Et |
| 3-Cl, 5-Cl | CF₃ | N | 0 | CH₂CF₃ |
| 3-Cl, 5-Cl | CF₃ | N | 0 | CH₂CN |
| 3-Cl, 5-Cl | CF₃ | N | 0 | n-Pr |
| 3-Cl, 5-Cl | CF₃ | N | 0 | i-Pr |
| 3-Cl, 5-Cl | CF₃ | N | 0 | CH₂(2-Py) |
| 3-Cl, 5-Cl | H | CH | 0 | Me |
| 3-Cl, 5-Cl | H | CH | 0 | CH₂F |
| 3-Cl, 5-Cl | H | CH | 0 | CHF₂ |
| 3-Cl, 5-Cl | H | CH | 0 | Et |
| 3-Cl, 5-Cl | H | CH | 0 | CH₂CF₃ |
| 3-Cl, 5-Cl | H | CH | 0 | CH₂CN |
| 3-Cl, 5-Cl | H | CH | 0 | n-Pr |
| 3-Cl, 5-Cl | H | CH | 0 | i-Pr |
| 3-Cl, 5-Cl | H | CH | 0 | CH₂(2-Py) |
| 3-Cl, 5-Cl | H | CH | 0 | c-Pr |
| 3-Cl, 5-Cl | H | CH | 0 | CH₂(c-Pr) |
| 3-Cl, 5-Cl | H | CH | 0 | CH₂C═CH₂ |
| 3-Cl, 5-Cl | H | CH | 0 | CH₂C≡CH |
| 3-Cl, 5-Cl | Me | CH | 0 | Me |
| 3-Cl, 5-Cl | Me | CH | 0 | CH₂F |
| 3-Cl, 5-Cl | Me | CH | 0 | CHF₂ |
| 3-Cl, 5-Cl | Me | CH | 0 | Et |
| 3-Cl, 5-Cl | Me | CH | 0 | CH₂CF₃ |
| 3-Cl, 5-Cl | Me | CH | 0 | CH₂CN |
| 3-Cl, 5-Cl | Me | CH | 0 | n-Pr |
| 3-Cl, 5-Cl | Me | CH | 0 | i-Pr |
| 3-Cl, 5-Cl | Me | CH | 0 | CH₂(2-Py) |
| 3-Cl, 5-Cl | Me | CH | 0 | c-Pr |
| 3-Cl, 5-Cl | Me | CH | 0 | CH₂(c-Pr) |
| 3-Cl, 5-Cl | Me | CH | 0 | CH₂C═CH₂ |
| 3-Cl, 5-Cl | Me | CH | 0 | CH₂C≡CH |
| 3-Cl, 5-Cl | Cl | CH | 0 | Me |
| 3-Cl, 5-Cl | Cl | CH | 0 | CH₂F |
| 3-Cl, 5-Cl | Cl | CH | 0 | CHF₂ |
| 3-Cl, 5-Cl | Cl | CH | 0 | Et |
| 3-Cl, 5-Cl | Cl | CH | 0 | CH₂CF₃ |
| 3-Cl, 5-Cl | Cl | CH | 0 | CH₂CN |
| 3-Cl, 5-Cl | Cl | CH | 0 | n-Pr |
| 3-Cl, 5-Cl | Cl | CH | 0 | i-Pr |
| 3-Cl, 5-Cl | Cl | CH | 0 | CH₂(2-Py) |
| 3-Cl, 5-Cl | Cl | CH | 0 | c-Pr |
| 3-Cl, 5-Cl | Cl | CH | 0 | CH₂(c-Pr) |
| 3-Cl, 5-Cl | Cl | CH | 0 | CH₂C═CH₂ |
| 3-Cl, 5-Cl | Cl | CH | 0 | CH₂C≡CH |
| 3-Cl, 5-Cl | H | CH | 2 | Me |
| 3-Cl, 5-Cl | H | CH | 2 | CH₂F |
| 3-Cl, 5-Cl | H | CH | 2 | CHF₂ |
| 3-Cl, 5-Cl | H | CH | 2 | Et |
| 3-Cl, 5-Cl | H | CH | 2 | CH₂CF₃ |
| 3-Cl, 5-Cl | H | CH | 2 | CH₂CN |
| 3-Cl, 5-Cl | H | CH | 2 | n-Pr |
| 3-Cl, 5-Cl | H | CH | 2 | i-Pr |
| 3-Cl, 5-Cl | H | CH | 2 | CH₂(2-Py) |
| 3-Cl, 5-Cl | H | CH | 2 | c-Pr |
| 3-Cl, 5-Cl | H | CH | 2 | CH₂(c-Pr) |
| 3-Cl, 5-Cl | H | CH | 2 | CH₂C═CH₂ |
| 3-Cl, 5-Cl | H | CH | 2 | CH₂C≡CH |
| 3-Cl, 5-Cl | Me | CH | 2 | Me |
| 3-Cl, 5-Cl | Me | CH | 2 | CH₂F |
| 3-Cl, 5-Cl | Me | CH | 2 | CHF₂ |
| 3-Cl, 5-Cl | Me | CH | 2 | Et |
| 3-Cl, 5-Cl | Me | CH | 2 | CH₂CF₃ |
| 3-Cl, 5-Cl | Me | CH | 2 | CH₂CN |
| 3-Cl, 5-Cl | Me | CH | 2 | n-Pr |
| 3-Cl, 5-Cl | Me | CH | 2 | i-Pr |
| 3-Cl, 5-Cl | Me | CH | 2 | CH₂(2-Py) |
| 3-Cl, 5-Cl | Me | CH | 2 | c-Pr |
| 3-Cl, 5-Cl | Me | CH | 2 | CH₂(c-Pr) |
| 3-Cl, 5-Cl | Me | CH | 2 | CH₂C═CH₂ |
| 3-Cl, 5-Cl | Me | CH | 2 | CH₂C≡CH |
| 3-Cl, 5-Cl | Cl | CH | 2 | Me |
| 3-Cl, 5-Cl | Cl | CH | 2 | CH₂F |
| 3-Cl, 5-Cl | Cl | CH | 2 | CHF₂ |
| 3-Cl, 5-Cl | Cl | CH | 2 | Et |
| 3-Cl, 5-Cl | Cl | CH | 2 | CH₂CF₃ |
| 3-Cl, 5-Cl | Cl | CH | 2 | CH₂CN |
| 3-Cl, 5-Cl | Cl | CH | 2 | n-Pr |

TABLE 12-continued

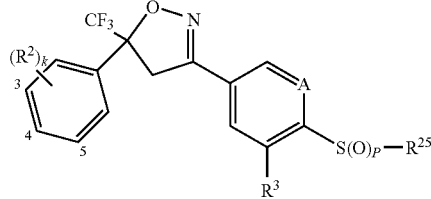

wherein k is 1, 2, 3, 4 or 5.

| (R²)ₖ | R³ | A³ | p | R²⁵ |
|---|---|---|---|---|
| 3-Cl, 5-Cl | Cl | CH | 2 | i-Pr |
| 3-Cl, 5-Cl | Cl | CH | 2 | CH₂(2-Py) |
| 3-Cl, 5-Cl | Cl | CH | 2 | c-Pr |
| 3-Cl, 5-Cl | Cl | CH | 2 | CH₂(c-Pr) |
| 3-Cl, 5-Cl | Cl | CH | 2 | CH₂C=CH₂ |
| 3-Cl, 5-Cl | Cl | CH | 2 | CH₂C≡CH |
| 3-Cl, 5-Cl | CF₃ | CH | 0 | Me |
| 3-Cl, 5-Cl | CF₃ | CH | 0 | CH₂F |
| 3-Cl, 5-Cl | CF₃ | CH | 0 | CHF₂ |
| 3-Cl, 5-Cl | CF₃ | CH | 0 | Et |
| 3-Cl, 5-Cl | CF₃ | CH | 0 | CH₂CF₃ |
| 3-Cl, 5-Cl | CF₃ | CH | 0 | CH₂CN |
| 3-Cl, 5-Cl | CF₃ | CH | 0 | n-Pr |
| 3-Cl, 5-Cl | CF₃ | CH | 0 | i-Pr |
| 3-Cl, 5-Cl | CF₃ | CH | 0 | CH₂(2-Py) |
| 3-Cl, 5-Cl | CF₃ | CH | 0 | c-Pr |
| 3-Cl, 5-Cl | CF₃ | CH | 0 | CH₂(c-Pr) |
| 3-Cl, 5-Cl | CF₃ | CH | 0 | CH₂C=CH₂ |
| 3-Cl, 5-Cl | CF₃ | CH | 0 | CH₂C≡CH |
| 3-Cl, 5-Cl | CF₃ | CH | 1 | Me |
| 3-Cl, 5-Cl | CF₃ | CH | 1 | CH₂F |
| 3-Cl, 5-Cl | CF₃ | CH | 1 | CHF₂ |
| 3-Cl, 5-Cl | CF₃ | CH | 1 | Et |
| 3-Cl, 5-Cl | CF₃ | CH | 1 | CH₂CF₃ |
| 3-Cl, 5-Cl | CF₃ | CH | 1 | CH₂CN |
| 3-Cl, 5-Cl | CF₃ | CH | 1 | n-Pr |
| 3-Cl, 5-Cl | CF₃ | CH | 1 | i-Pr |
| 3-Cl, 5-Cl | CF₃ | CH | 1 | CH₂(2-Py) |
| 3-Cl, 5-Cl | CF₃ | CH | 1 | c-Pr |
| 3-Cl, 5-Cl | CF₃ | CH | 1 | CH₂(c-Pr) |
| 3-Cl, 5-Cl | CF₃ | CH | 1 | CH₂C=CH₂ |
| 3-Cl, 5-Cl | CF₃ | CH | 1 | CH₂C≡CH |
| 3-Cl, 5-Cl | CF₃ | CH | 2 | Me |
| 3-Cl, 5-Cl | CF₃ | CH | 2 | CH₂F |
| 3-Cl, 5-Cl | CF₃ | CH | 2 | CHF₂ |
| 3-Cl, 5-Cl | CF₃ | CH | 2 | Et |
| 3-Cl, 5-Cl | CF₃ | CH | 2 | CH₂CF₃ |
| 3-Cl, 5-Cl | CF₃ | CH | 2 | CH₂CN |
| 3-Cl, 5-Cl | CF₃ | CH | 2 | n-Pr |
| 3-Cl, 5-Cl | CF₃ | CH | 2 | i-Pr |
| 3-Cl, 5-Cl | CF₃ | CH | 2 | CH₂(2-Py) |
| 3-Cl, 5-Cl | CF₃ | CH | 2 | c-Pr |
| 3-Cl, 5-Cl | CF₃ | CH | 2 | CH₂(c-Pr) |
| 3-Cl, 5-Cl | CF₃ | CH | 2 | CH₂C=CH₂ |
| 3-Cl, 5-Cl | CF₃ | CH | 2 | CH₂C≡CH |
| 3-Cl, 5-Cl | CN | CH | 1 | Me |
| 3-Cl, 5-Cl | CN | CH | 1 | CH₂F |
| 3-Cl, 5-Cl | CN | CH | 1 | CHF₂ |
| 3-Cl, 5-Cl | CN | CH | 1 | Et |
| 3-Cl, 5-Cl | CN | CH | 1 | CH₂CF₃ |
| 3-Cl, 5-Cl | CN | CH | 1 | CH₂CN |
| 3-Cl, 5-Cl | CN | CH | 1 | n-Pr |
| 3-Cl, 5-Cl | CN | CH | 1 | i-Pr |
| 3-Cl, 5-Cl | CN | CH | 1 | CH₂(2-Py) |
| 3-Cl, 5-Cl | CN | CH | 1 | c-Pr |
| 3-Cl, 5-Cl | CN | CH | 1 | CH₂(c-Pr) |
| 3-Cl, 5-Cl | CN | CH | 1 | CH₂C=CH₂ |
| 3-Cl, 5-Cl | CN | CH | 1 | CH₂C≡CH |
| 3-Cl, 5-Cl | CN | CH | 2 | i-Pr |
| 3-Cl, 5-Cl | CN | CH | 2 | CH₂(2-Py) |
| 3-Cl, 5-Cl | CN | CH | 2 | c-Pr |
| 3-Cl, 5-Cl | CN | CH | 2 | CH₂(c-Pr) |
| 3-Cl, 5-Cl | CN | CH | 2 | CH₂C=CH₂ |
| 3-Cl, 5-Cl | CN | CH | 2 | CH₂C≡CH |

TABLE 12-continued

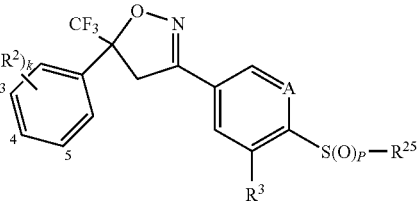

wherein k is 1, 2, 3, 4 or 5.

| (R²)ₖ | R³ | A³ | p | R²⁵ |
|---|---|---|---|---|
| 3-Cl, 5-Cl | Cl | N | 0 | Me |
| 3-Cl, 5-Cl | Cl | N | 0 | Et |
| 3-Cl, 5-Cl | Cl | N | 0 | CH₂CF₃ |
| 3-Cl, 5-Cl | Cl | N | 0 | CH₂CN |
| 3-Cl, 5-Cl | Cl | N | 0 | n-Pr |
| 3-Cl, 5-Cl | Cl | N | 0 | i-Pr |
| 3-Cl, 5-Cl | Cl | N | 0 | CH₂(2-Py) |
| 3-Cl, 5-Cl | OMe | N | 0 | Me |
| 3-Cl, 5-Cl | OMe | N | 0 | Et |
| 3-Cl, 5-Cl | OMe | N | 0 | CH₂CF₃ |
| 3-Cl, 5-Cl | OMe | N | 0 | CH₂CN |
| 3-Cl, 5-Cl | OMe | N | 0 | n-Pr |
| 3-Cl, 5-Cl | OMe | N | 0 | i-Pr |
| 3-Cl, 5-Cl | OMe | N | 0 | CH₂(2-Py) |
| 3-Cl, 5-Cl | CN | N | 0 | Me |
| 3-Cl, 5-Cl | CN | N | 0 | Et |
| 3-Cl, 5-Cl | CN | N | 0 | CH₂CF₃ |
| 3-Cl, 5-Cl | CN | N | 0 | CH₂CN |
| 3-Cl, 5-Cl | CN | N | 0 | n-Pr |
| 3-Cl, 5-Cl | CN | N | 0 | i-Pr |
| 3-Cl, 5-Cl | CN | N | 0 | CH₂(2-Py) |

TABLE 13 wherein k is 1, 2, 3, 4 or 5.

| (R²)ₖ | R³ | A³ | R²⁸ | R²⁹ |
|---|---|---|---|---|
| 3-Cl, 5-Cl | H | CH | H | Me |
| 3-Cl, 5-Cl | H | CH | H | Et |
| 3-Cl, 5-Cl | H | CH | H | CH₂CF₃ |
| 3-Cl, 5-Cl | H | CH | H | i-Pr |
| 3-Cl, 5-Cl | H | CH | H | c-Pr |
| 3-Cl, 5-Cl | Cl | CH | H | Me |
| 3-Cl, 5-Cl | Cl | CH | H | Et |
| 3-Cl, 5-Cl | Cl | CH | H | CH₂CF₃ |
| 3-Cl, 5-Cl | Cl | CH | H | i-Pr |
| 3-Cl, 5-Cl | Cl | CH | H | c-Pr |
| 3-Cl, 5-Cl | Me | CH | H | Me |
| 3-Cl, 5-Cl | Me | CH | H | Et |
| 3-Cl, 5-Cl | Me | CH | H | CH₂CF₃ |
| 3-Cl, 5-Cl | Me | CH | H | i-Pr |
| 3-Cl, 5-Cl | Me | CH | H | c-Pr |
| 3-Cl, 5-Cl | CN | CH | H | Me |
| 3-Cl, 5-Cl | CN | CH | H | Et |
| 3-Cl, 5-Cl | CN | CH | H | CH₂CF₃ |
| 3-Cl, 5-Cl | CN | CH | H | i-Pr |
| 3-Cl, 5-Cl | CN | CH | H | c-Pr |
| 3-Cl, 5-Cl | H | CH | CN | Me |
| 3-Cl, 5-Cl | H | CH | CN | Et |
| 3-Cl, 5-Cl | H | CH | CN | CH₂CF₃ |

TABLE 13-continued

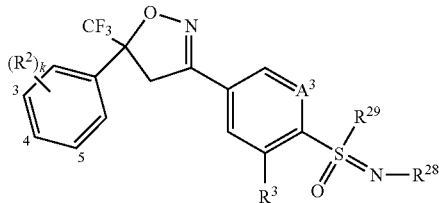

wherein k is 1, 2, 3, 4 or 5.

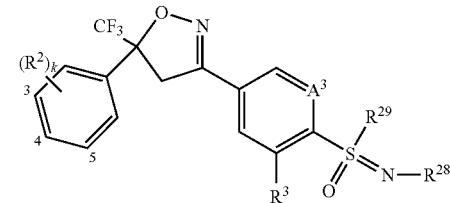

wherein k is 1, 2, 3, 4 or 5.

| (R²)ₖ | R³ | A³ | R²⁸ | R²⁹ |
|---|---|---|---|---|
| 3-Cl, 5-Cl | H | CH | CN | i-Pr |
| 3-Cl, 5-Cl | H | CH | CN | c-Pr |
| 3-Cl, 5-Cl | Cl | CH | CN | Me |
| 3-Cl, 5-Cl | Cl | CH | CN | Et |
| 3-Cl, 5-Cl | Cl | CH | CN | CH₂CF₃ |
| 3-Cl, 5-Cl | Cl | CH | CN | i-Pr |
| 3-Cl, 5-Cl | Cl | CH | CN | c-Pr |
| 3-Cl, 5-Cl | Me | CH | CN | Me |
| 3-Cl, 5-Cl | Me | CH | CN | Et |
| 3-Cl, 5-Cl | Me | CH | CN | CH₂CF₃ |
| 3-Cl, 5-Cl | Me | CH | CN | i-Pr |
| 3-Cl, 5-Cl | Me | CH | CN | c-Pr |
| 3-Cl, 5-Cl | CN | CH | CN | Me |
| 3-Cl, 5-Cl | CN | CH | CN | Et |
| 3-Cl, 5-Cl | CN | CH | CN | CH₂CF₃ |
| 3-Cl, 5-Cl | CN | CH | CN | i-Pr |
| 3-Cl, 5-Cl | CN | CH | CN | c-Pr |
| 3-Cl, 5-Cl | H | N | H | Me |
| 3-Cl, 5-Cl | H | N | H | Et |
| 3-Cl, 5-Cl | H | N | H | CH₂CF₃ |
| 3-Cl, 5-Cl | H | N | H | i-Pr |
| 3-Cl, 5-Cl | H | N | H | c-Pr |
| 3-Cl, 5-Cl | H | N | CN | Me |
| 3-Cl, 5-Cl | H | N | CN | Er |
| 3-Cl, 5-Cl | H | N | CN | CH₂CF₃ |
| 3-Cl, 5-Cl | H | N | CN | i-Pr |
| 3-Cl, 5-Cl | H | N | CN | c-Pr |
| 3-Cl, 5-Cl | Cl | N | H | Me |
| 3-Cl, 5-Cl | Cl | N | H | Et |
| 3-Cl, 5-Cl | Cl | N | H | CH₂CF₃ |
| 3-Cl, 5-Cl | Cl | N | H | i-Pr |
| 3-Cl, 5-Cl | Cl | N | H | c-Pr |
| 3-Cl, 5-Cl | Cl | N | CN | Me |
| 3-Cl, 5-Cl | Cl | N | CN | Et |
| 3-Cl, 5-Cl | Cl | N | CN | CH₂CF₃ |
| 3-Cl, 5-Cl | Cl | N | CN | i-Pr |
| 3-Cl, 5-Cl | Cl | N | CN | c-Pr |
| 3-Cl, 5-Cl | Me | N | H | Me |
| 3-Cl, 5-Cl | Me | N | H | Et |
| 3-Cl, 5-Cl | Me | N | H | CH₂CF₃ |
| 3-Cl, 5-Cl | Me | N | H | i-Pr |
| 3-Cl, 5-Cl | Me | N | H | c-Pr |
| 3-Cl, 5-Cl | Me | N | CN | Me |
| 3-Cl, 5-Cl | Me | N | CN | Et |
| 3-Cl, 5-Cl | Me | N | CN | CH₂CF₃ |
| 3-Cl, 5-Cl | Me | N | CN | i-Pr |
| 3-Cl, 5-Cl | Me | N | CN | c-Pr |
| 3-Cl, 5-Cl | CN | N | H | Me |
| 3-Cl, 5-Cl | CN | N | H | Et |
| 3-Cl; 5-Cl | CN | N | H | CH₂CF₃ |
| 3-Cl, 5-Cl | CN | N | H | i-Pr |
| 3-Cl, 5-Cl | CN | N | H | c-Pr |
| 3-Cl, 5-Cl | CN | N | CN | Me |
| 3-Cl, 5-Cl | CN | N | CN | Et |
| 3-Cl, 5-Cl | CN | N | CN | CH₂CF₃ |
| 3-Cl; 5-Cl | CN | N | CN | i-Pr |
| 3-Cl, 5-Cl | CN | N | CN | c-Pr |
| 3-Cl, 5-Cl | H | CH | COCF₃ | Me |
| 3-Cl, 5-Cl | H | CH | COCF₃ | Et |
| 3-Cl, 5-Cl | H | CH | COCF₃ | CH₂CF₃ |
| 3-Cl, 5-Cl | H | CH | COCF₃ | i-Pr |
| 3-Cl, 5-Cl | H | CH | COCF₃ | c-Pr |
| 3-Cl, 5-Cl | Cl | CH | COCF₃ | Me |
| 3-Cl, 5-Cl | Cl | CH | COCF₃ | Et |
| 3-Cl, 5-Cl | Cl | CH | COCF₃ | CH₂CF₃ |
| 3-Cl, 5-Cl | Cl | CH | COCF₃ | i-Pr |
| 3-Cl, 5-Cl | Cl | CH | COCF₃ | c-Pr |
| 3-Cl, 5-Cl | Me | CH | COCF₃ | Me |
| 3-Cl, 5-Cl | Me | CH | COCF₃ | Et |
| 3-Cl, 5-Cl | Me | CH | COCF₃ | CH₂CF₃ |
| 3-Cl, 5-Cl | Me | CH | COCF₃ | i-Pr |
| 3-Cl, 5-Cl | Me | CH | COCF₃ | c-Pr |
| 3-Cl, 5-Cl | CN | CH | COCF₃ | Me |
| 3-Cl, 5-Cl | CN | CH | COCF₃ | Et |
| 3-Cl, 5-Cl | CN | CH | COCF₃ | CH₂CF₃ |
| 3-Cl, 5-Cl | CN | CH | COCF₃ | i-Pr |
| 3-Cl, 5-Cl | CN | CH | COCF₃ | cPr |
| 3-Cl, 5-Cl | H | CH | NO₂ | Me |
| 3-Cl, 5-Cl | H | CH | NO₂ | Et |
| 3-Cl, 5-Cl | H | CH | NO₂ | CH₂CF₃ |
| 3-Cl, 5-Cl | H | CH | NO₂ | i-Pr |
| 3-Cl, 5-Cl | H | CH | NO₂ | c-Pr |
| 3-Cl, 5-Cl | Cl | CH | NO₂ | Me |
| 3-Cl, 5-Cl | Cl | CH | NO₂ | Et |
| 3-Cl, 5-Cl | Cl | CH | NO₂ | CH₂CF₃ |
| 3-Cl, 5-Cl | Cl | CH | NO₂ | i-Pr |
| 3-Cl, 5-Cl | Cl | CH | NO₂ | c-Pr |
| 3-Cl, 5-Cl | Me | CH | NO₂ | Me |
| 3-Cl, 5-Cl | Me | CH | NO₂ | Et |
| 3-Cl, 5-Cl | Me | CH | NO₂ | CH₂CF₃ |
| 3-Cl, 5-Cl | Me | CH | NO₂ | i-Pr |
| 3-Cl, 5-Cl | Me | CH | NO₂ | c-Pr |
| 3-Cl, 5-Cl | CN | CH | NO₂ | Me |
| 3-Cl, 5-Cl | CN | CH | NO₂ | Et |
| 3-Cl, 5-Cl | CN | CH | NO₂ | CH₂CF₃ |
| 3-Cl, 5-Cl | CN | CH | NO₂ | i-Pr |
| 3-Cl, 5-Cl | CN | CH | NO₂ | c-Pr |
| 3-Cl, 5-Cl | H | N | COCF₃ | Me |
| 3-Cl, 5-Cl | H | N | COCF₃ | Et |
| 3-Cl, 5-Cl | H | N | COCF₃ | CH₂CF₃ |
| 3-Cl, 5-Cl | H | N | COCF₃ | i-Pr |
| 3-Cl, 5-Cl | H | N | COCF₃ | c-Pr |
| 3-Cl, 5-Cl | H | N | NO₂ | Me |
| 3-Cl, 5-Cl | H | N | NO₂ | Et |
| 3-Cl, 5-Cl | H | N | NO₂ | CH₂CF₃ |
| 3-Cl, 5-Cl | H | N | NO₂ | i-Pr |
| 3-Cl, 5-Cl | H | N | NO₂ | c-Pr |
| 3-Cl, 5-Cl | Cl | N | COCF₃ | Me |
| 3-Cl, 5-Cl | Cl | N | COCF₃ | Et |
| 3-Cl, 5-Cl | Cl | N | COCF₃ | CH₂CF₃ |
| 3-Cl, 5-Cl | Cl | N | COCF₃ | i-Pr |
| 3-Cl, 5-Cl | Cl | N | COCF₃ | c-Pr |
| 3-Cl, 5-Cl | Cl | N | NO₂ | Me |
| 3-Cl, 5-Cl | Cl | N | NO₂ | Et |
| 3-Cl, 5-Cl | Cl | N | NO₂ | CH₂CF₃ |
| 3-Cl, 5-Cl | Cl | N | NO₂ | i-Pr |
| 3-Cl, 5-Cl | Cl | N | NO₂ | c-Pr |
| 3-Cl, 5-Cl | Me | N | COCF₃ | Me |
| 3-Cl, 5-Cl | Me | N | COCF₃ | Et |
| 3-Cl, 5-Cl | Me | N | COCF₃ | CH₂CF₃ |
| 3-Cl, 5-Cl | Me | N | COCF₃ | i-Pr |
| 3-Cl, 5-Cl | Me | N | COCF₃ | c-Pr |
| 3-Cl, 5-Cl | Me | N | NO₂ | Me |
| 3-Cl, 5-Cl | Me | N | NO₂ | Et |
| 3-Cl, 5-Cl | Me | N | NO₂ | CH₂CF₃ |
| 3-Cl, 5-Cl | Me | N | NO₂ | i-Pr |
| 3-Cl, 5-Cl | Me | N | NO₂ | c-Pr |
| 3-Cl, 5-Cl | CN | N | COCF₃ | Me |

TABLE 13-continued

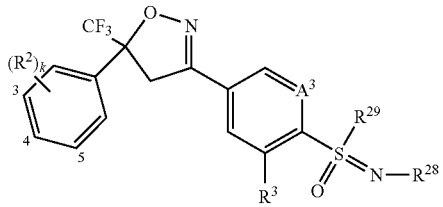

wherein k is 1, 2, 3, 4 or 5.

| $(R^2)_k$ | $R^3$ | $A^3$ | $R^{28}$ | $R^{29}$ |
|---|---|---|---|---|
| 3-Cl, 5-Cl | CN | N | COCF$_3$ | Et |
| 3-Cl, 5-Cl | CN | N | COCF$_3$ | CH$_2$CF$_3$ |
| 3-Cl, 5-Cl | CN | N | COCF$_3$ | i-Pr |
| 3-Cl, 5-Cl | CN | N | COCF$_3$ | c-Pr |
| 3-Cl, 5-Cl | CN | N | NO$_2$ | Me |
| 3-Cl, 5-Cl | CN | N | NO$_2$ | Et |
| 3-Cl, 5-Cl | CN | N | NO$_2$ | CH$_2$CF$_3$ |
| 3-Cl, 5-Cl | CN | N | NO$_2$ | i-Pr |
| 3-Cl, 5-Cl | CN | N | NO$_2$ | c-Pr |

Formulation/Utility

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials,* annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying- to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering,* Dec. 4, 1967, pp 147-48, *Perry's Chemical Engineer's Handbook,* 4th Ed., McGraw-Hill, New York 1963, pages 8-57 and following, and WO 91/13546. Pellets can be prepared as described in U.S. Pat. No. 4,172, 714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989, and *Developments in formulation technology*, PJB Publications, Richmond, UK, 2000.

In the following Examples, all percentages are by weight and all formulations are prepared in conventional ways. Compound numbers refer to compounds in Index Tables A-D. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

High Strength Concentrate

| | |
|---|---|
| Compound 9 | 98.5% |
| silica aerogel | 0.5% |
| synthetic amorphous fine silica | 1.0% |

Example B

Wettable Powder

| | |
|---|---|
| Compound 14 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 26 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 38 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 42 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 63 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| Compound 72 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

Fertilizer Stick

| | |
|---|---|
| Compound 107 | 2.5% |
| pyrrolidone-styrene copolymer | 4.8% |
| tristyrylphenyl 16-ethoxylate | 2.3% |
| talc | 0.8% |
| corn starch | 5.0% |

-continued

| | |
|---|---|
| Nitrophoska ® Permanent 15-9-15 slow-release fertilizer (BASF) | 36.0% |
| kaolin | 38.0% |
| water | 10.6% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present invention are suitable for systemic and/or non-systemic control of infestation or infection by parasites on animals. Compounds and compositions of the present invention are particularly suitable for combating external parasitic or disease transmitting pests. Compounds and compositions of the present invention are suitable for combating parasites that infest agricultural working animals, such as cattle, sheep, goats, horses, pigs, donkeys, camels, buffalos, rabbits, hens, turkeys, ducks, geese and bees; pet animals and domestic animals such as dogs, cats, pet birds and aquarium fish; as well as so-called experimental animals, such as hamsters, guinea pigs, rats and mice. By combating these parasites, fatalities and performance reduction (in terms of meat, milk, wool, skins, eggs, honey, etc.) are reduced, so that applying a composition comprising a compound of the present invention allows more economic and simple husbandry of animals.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped, armyworm (*Spodoptera orinthogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* War), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga* incertulas Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Caiposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuscbel), granary weevil (*Sitophilus grananius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus vestitus*), Denver billbug (*Sphenophorus cicatrtus* Fahaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephal borealis* Arrow), southern masked chafer (*Cyclocephala immaculata* Olivier or *C. lurida* Bland) dung beetle and white grub (*Aphodius* spp.), black turfgrass ataenius (*Ataenius spretulus* Haldeman), green June beetle (*Cotinis nitida* Linnaeus), Asiatic garden beetle (*Maladera catanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomnic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Einpoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae. Also included are eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* Mcregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor varabilis* Say), lone star tick (*Amblyomma americanum* Linnaeus)) and scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borelli* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.); cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontoternes obesus* Rambur), Kalotermitidae (e.g., *Cryptotermes* sp.), and Rhinotermitidae (e.g., *Reticulitermes* sp., *Coptoternes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutiternes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention also have activity on members from the order Hemiptera including: *Acrosternum hilare* Say (green stink bug), *Anasa tristis* De Geer (squash bug), *Blissus Leucopterus* leucopterus Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of compounds of this invention for controlling silverleaf whitefly (*Bemisia argentifolii*). Of note is use of compounds of this invention for controlling western flower thrips (*Frankliniella occidentalis*). Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*). Of note is use of compounds of this invention for controlling fall armyworm (*Spodoprera frugiperda*).

Compounds of this invention can also be mixed with one or more other biologically active compounds or agents including insecticides, fungicides, nematocides, bactericides, acaricides, herbicides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, an N-oxide or salt thereof, and an effective amount of at least one additional biologically active compound or agent and can further comprise at least one of a surfactant, a solid diluent or a liquid diluent. The other biologically active compounds or agents can be formulated in compositions comprising at least one of a surfactant, solid or liquid diluent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Other biologically active compounds or agents useful in the compositions of the present invention can be selected from invertebrate pest control agents having a different mode of action or a different chemical class including macrocyclic lactones, neonicotinoids, octopamine receptor ligands, ryanodine receptor ligands, ecdysone agonists, sodium channel modulators, chitin synthesis inhibitors, nereisotoxin analogs, mitochondrial electron transport inhibitors, cholinesterase inhibitors, cyclodiene insecticides, molting inhibitors, GABA (γ-aminobutyric acid)-regulated chloride channel blockers, juvenile hormone mimics, lipid biosynthesis inhibitors and biological agents including nucleopolyhedrovirus (NPV), a member of *Bacillus thuringiensis*, an encapsulated delta-endotoxin of *Bacillus thuringiensis*; and a naturally occurring or a genetically modified viral insecticide. Of note are additional biologically active compounds or agents selected from insecticides of the group consisting of pyrethroids, carbamates, neonicotinoids, neuronal sodium channel blockers, insecticidal macrocyclic lactones, γ-aminobutyric acid antagonists, insecticidal ureas and juvenile hormone mimics, a member of *Bacillus thuringiensis*, a *Bacillus thuringiensis* delta-endotoxin, and a naturally occurring or a genetically modified viral insecticide.

Of note is a composition of the present invention wherein at least one additional biologically active compound or agent is selected from insecticides of the group consisting of macrocyclic lactones, neonicotinoids, octopamine receptor ligands, ryanodine receptor ligands, ecdysone agonists, sodium channel modulators, chitin synthesis inhibitors, nereisotoxin analogs, mitochondrial electron transport inhibitors, cholinesterase inhibitors, cyclodiene insecticides, molting inhibitors, GABA-regulated chloride channel blockers, juvenile hormone mimics, biological agents, and lipid biosynthesis inhibitors.

Examples of such biologically active compounds or agents with which compounds of this invention can be formulated are: insecticides such as abamectin, acephate, acetamiprid, acetoprole, amidoflumet (S-1955), avermectin, azadirachtin, azinphos-methyl, bifenthrin, bifenazate, bistrifluoron, buprofezin, carbofuran, cartap, chlorfenapyr, chlorfluazuron; chlorantraniliprole (DPX-E2Y45), chlorpyrifos, chlorpyrifos-methyl, chromafenozide, clothianidin, cyflumetofen, cyfluthrin, beta-cyfluthrin, cyhalothrin, gamma-cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflurixzone, metaldehyde, methamidophos, methidathion, methomyl, methoprene, methoxychlor, metofluthrin, monocrotophos, methoxyfenozide, monocrotophos, nitenpyram, nithiazine, novaluron, noviflumuron (XDE007), oxamyl, parathion, parathion-methyl, permethrin, phorate, phosalone, phosmet, phosphamidon, pirimicarb, profenofos, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, tiosultap-sodium, tolfenpyrad, tralomethrin, triazamate, trichlorfon and triflumuron; fungicides such as acibenzolar, aldimorph, amisulbrom, azaconazole, azoxystrobin, benalaxyl, benomyl, bentiavalicarb, benthiavalicarb-isopropyl, binomial, biphenyl, bittanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencararid, fenfuram, fenhexamide, fenoxanil, fenpiclonil, fenpropicdin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazble, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole; myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarbhydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simneconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, tritiсonazole, uniconazole, validamycin, vinclozolin, zineb, ziram, and zoxamide; nematocides such as aldicarb, imicyafos, oxamyl and fenariphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai, Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedroviuus (NPV) such as *Helicoverpa zea* nucleopolyhedrovirus (HzNPV), *Anagrapha falcifera* nucleopolyhedrovirus (AfrPV); and granulosis vius (GV) such as *Cydia pomonella* granulosis virus (CpGV).

Compounds of this invention and compositions thereof can be applied to plants genetically transformed to express proteins toxic to invertebrate pests (such as *Bacillus thuringiensis* delta-endotoxins). The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

Of note is a composition of the present invention wherein at least one additional biologically active compound or agent is selected from the group consisting of abamectin, acephate, acetamiprid, acetoprole, aldicarb, amidoflumet, amitraz, avermectin, azadirachtin, azinphos-methyl, bifenthrin, bifenazate, bistrifluoron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyflumetofen, cyfluthrin, beta-cyfluthrin, cyhalothrin, gamma-cyhalothrin, lambda-cyhalothrin; cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron; fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone; ryanodine, spinetoram, spinosad, spiridiclofen, spiromesifen (BSN 2060), spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron, *Bacillus thuringiensis* subsp. *aizawai, Bacillus thuringiensis* subsp. *kurstaki*, nucleopolyhedrovirus, an encapsulated delta-endotoxin of *Bacillus thuringiensis*, baculovirus, entomopathogenic bacteria, entomopathogenic virus and entomopathogenic fungi.

Of particular note is a composition of the present invention wherein the at least one additional biologically active compound or agent is selected from the group consisting of abamectin, acephate, acetamiprid, acetoprole, amidoflumet, avermectin, azadirachtin, azinphos-methyl, bifenthrin, bifenazate, bistrifluron, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim, flufenoxuron, fonophos, gamma-cyhalothrin, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, protrifenbute, pymetrozine, pyrafluprole, pyrethrin, pyridalyl, pyrifluquinazon, pyriprole, pyriproxyfen, rotenone, ryanodine, S1812 (Valent), spinosad, spiridiclofen, spiromesifen, spirotetramat, sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron, aldicarb, imicyafos, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben, tebufenpyrad, *Bacillus thuringiensis aizawai*, *Bacillus thuringiensis kurstaki*, *Bacillus thuringiensis* delta endotoxin, baculovirus, entomopathogenic bacteria, entomopathogenic virus and entomopathogenic fungi.

Also of note is a composition of the present invention wherein at least one additional biologically active compound or agent is selected from the group consisting of abamectin, acetamiprid, amitraz, avermectin, azadirachtin, bifenthrin, buprofezin, cartap, chlorantraniliprole, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin; endosulfan, esfenvalerate, ethiprole; fenothiocarb, fenoxycarb, fenvalerate, fipronil, flonicamid, flubendiamide, flufenoxuron; hexaflumuron, hydramethylnon, imidacloprid, indoxacarb, lufenuron; metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai, Bacillus thuringiensis* subsp. *kurstaki*, nucleopolyhedrovirus and an encapsulated delta-endotoxin of *Bacillus thuringiensis.*

Of further note is a composition of the present invention wherein the at least one additional biologically active compound or agent is selected from the group consisting of abamectin, acetamiprid, amitraz, an anthranilic diamide, avermectin, azadirachtin, beta-cyfluthrin, bifenthrin, buprofezin, cartap, chlorfenapyr, chlorpyrifos, chlothianidin, cyfluthrin, cyhalothrin, cypermetrin, cyromazine, deltamethrin, dieldrin, dinotefruan, diofenolan, emamectin, emamectin benzoate, endosulfan, esfenvalerate, tethiprole, fenothiocarb, fenoxycarb, fenvalerate, fipronil, flonicamid, flufenoxuron, hexaflumuron, hydramethylnon, imidacloprid, indoxacarb, lambda-cyhalothrin, lufenuron, metaflumizone, methomyl, methoprene, methoxyfenozide, nitenpyram, nithiazine, novaluron, NPR, oxamyl, pymetrozine, pyrethrin, pyridaben, pyridalyl, pyriproxyfen, ryanodine, spinosal, spirodiclofen, spiromesifen, tebufenozide, thiacloprid, thiamethoxam, thiodicarb, tralomethrin, triazamate, triflumuron, *Bacillus thuringiensis, Bacillus thuringiensis* delta toxin, and *Beauvaria bassiana.*

For embodiments where one or more of these various mixing partners are used, the weight ratio of these various mixing partners (in total) to the compound of Formula 1 is typically between about 1:3006 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of invertebrate pests controlled beyond the spectrum controlled by the compound of Formula 1 alone.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Of note is a combination of a compound of Formula 1 with at least one other invertebrate pest control active ingredient. Of particular note is such a combination where the other invertebrate pest control active ingredient has different site of action from the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but a different site of action. Contacting a plant genetically modified to express an invertebrate pest compound (e.g., protein) or the locus of the plant with a biologically effective amount of a compound of this invention can also provide a broader spectrum of plant protection and be advantageous for resistance management.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1, an N-oxide, or a salt thereof, (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |

TABLE A-continued

| Invertebrate Pest Control Agent | Mode of Action or Chemical Class | Typical Weight Ratio |
|---|---|---|
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

One embodiment of invertebrate pest control agents (e.g., insecticides and acaricides) for mixing with compounds of this invention include sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine, anthranilic diamides such as chlorantraniliprole (see U.S. Pat. No. 6,747, 047, PCT Publications WO 2003/015518 and WO 2004/067528) and flubendiamide (see U.S. Pat. No. 6,603,044); nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of biological agents for mixing with compounds of this invention include nucleopolyhedrovirus such as HzNPV and AfNPV; *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi. Of note is the composition of the present invention wherein the at least one additional biologically active compound or agent is selected from the Invertebrate Pest Control Agents listed in Table A above. Also of note is the composition of the present invention wherein the at least one additional biologically active compound or agent is selected from the group consisting of cypermethrin, cyhalothrin, cyfluthrin, beta-cyfluthrin, esfenvalerate, fenvalerate, tralomethrin, fenothiocarb, methomyl, oxamyl, thiodicarb, acetamiprid, clothianidin, imidacloprid, thiamethoxam, thiacloprid, indoxacarb, spinosad, abamectin, avermectin, emamectin, endosulfan, ethiprole, fipronil, flufenoxuron, triflumuron, diofenolan, pyriproxyfen, pymetrozine, amitraz, *Bacillus thuringiensis aisawai*, *Bacillus thuringiensis kurstaki*, *Bacillus thuringiensis* delta endotoxin and entomophagous fungi.

The weight ratios of a compound, including a compound of Formula 1, an N-oxide or a salt thereof, to the additional invertebrate pest control agent typically are between 1000:1 and 1:1000, with one embodiment being between 500:1 and 1:500, another embodiment being between 250:1 and, 1:200 and another embodiment being between 100:1 and 1:50.

Listed below in Table B are embodiments of specific compositions comprising a compound of Formula 1 (compound numbers refer to compounds in Index Tables A-D) and an additional invertebrate pest control agent.

TABLE B

| Mixture No. | Comp. No. | and | Invertebrate Pest Control Agent |
|---|---|---|---|
| A-1 | 9 | and | Abamectin |
| A-2 | 9 | and | Acetamiprid |
| A-3 | 9 | and | Amitraz |
| A-4 | 9 | and | Avermectin |
| A-5 | 9 | and | Azadirachtin |
| A-6 | 9 | and | Beta-cyfluthrin |

TABLE B-continued

| Mixture No. | Comp. No. | and | Invertebrate Pest Control Agent |
|---|---|---|---|
| A-7 | 9 | and | Bifenthrin |
| A-8 | 9 | and | Buprofezin |
| A-9 | 9 | and | Cartap |
| A-10 | 9 | and | Chlorantraniliprole |
| A-11 | 9 | and | Chlorfenapyr |
| A-12 | 9 | and | Chlorpyrifos |
| A-13 | 9 | and | Clothianidin |
| A-14 | 9 | and | Cyfluthrin |
| A-15 | 9 | and | Cyhalothrin |
| A-16 | 9 | and | Cypermethrin |
| A-17 | 9 | and | Cyromazine |
| A-18 | 9 | and | Deltamethrin |
| A-19 | 9 | and | Dieldrin |
| A-20 | 9 | and | Dinotefuran |
| A-21 | 9 | and | Diofenolan |
| A-22 | 9 | and | Emamectin |
| A-23 | 9 | and | Endosulfan |
| A-24 | 9 | and | Esfenvalerate |
| A-25 | 9 | and | Ethiprole |
| A-26 | 9 | and | Fenothiocarb |
| A-27 | 9 | and | Fenoxycarb |
| A-28 | 9 | and | Fenvalerate |
| A-29 | 9 | and | Fipronil |
| A-30 | 9 | and | Flonicamid |
| A-31 | 9 | and | Flubendiamide |
| A-32 | 9 | and | Flufenoxuron |
| A-33 | 9 | and | Hexaflumuron |
| A-34 | 9 | and | Hydramethylnon |
| A-35 | 9 | and | Imidacloprid |
| A-36 | 9 | and | Indoxacarb |
| A-37 | 9 | and | Lambda-cyhalothrin |
| A-38 | 9 | and | Lufenuron |
| A-39 | 9 | and | Metaflumizone |
| A-40 | 9 | and | Methomyl |
| A-41 | 9 | and | Methoprene |
| A-42 | 9 | and | Methoxyfenozide |
| A-43 | 9 | and | Nitenpyram |
| A-44 | 9 | and | Nithiazine |
| A-45 | 9 | and | Novaluron |
| A-46 | 9 | and | Oxamyl |
| A-47 | 9 | and | Pymetrozine |
| A-48 | 9 | and | Pyrethrin |
| A-49 | 9 | and | Pyridaben |
| A-50 | 9 | and | Pyridalyl |
| A-51 | 9 | and | Pyriproxyfen |
| A-52 | 9 | and | Ryanodine |
| A-53 | 9 | and | Spinetoram |
| A-54 | 9 | and | Spinosad |
| A-55 | 9 | and | Spirodiclofen |
| A-56 | 9 | and | Spiromesifen |
| A-57 | 9 | and | Tebufenozide |
| A-58 | 9 | and | Thiacloprid |
| A-59 | 9 | and | Thiamethoxam |
| A-60 | 9 | and | Thiodicarb |
| A-61 | 9 | and | Thiosultap-sodium |
| A-62 | 9 | and | Tralomethrin |
| A-63 | 9 | and | Triazamate |
| A-64 | 9 | and | Triflumuron |
| A-65 | 9 | and | *Bacillus thuringiensis* |
| A-66 | 9 | and | *Bacillus thuringiensis* delta-endotoxin |
| A-67 | 9 | and | NPV (e.g., Gemstar) |
| B-1 | 42 | and | Abamectin |
| B-2 | 42 | and | Acetamiprid |
| B-3 | 42 | and | Amitraz |
| B-4 | 42 | and | Avermectin |
| B-5 | 42 | and | Azadirachtin |
| B-6 | 42 | and | Beta-cyfluthrin |
| B-7 | 42 | and | Bifenthrin |
| B-8 | 42 | and | Buprofezin |
| B-9 | 42 | and | Cartap |
| B-10 | 42 | and | Chlorantraniliprole |
| B-11 | 42 | and | Chlorfenapyr |
| B-12 | 42 | and | Chlorpyrifos |
| B-13 | 42 | and | Clothianidin |
| B-14 | 42 | and | Cyfluthrin |
| B-15 | 42 | and | Cyhalothrin |
| B-16 | 42 | and | Cypermethrin |
| B-17 | 42 | and | Cyromazine |
| B-18 | 42 | and | Deltamethrin |
| B-19 | 42 | and | Dieldrin |
| B-20 | 42 | and | Dinotefuran |
| B-21 | 42 | and | Diofenolan |
| B-22 | 42 | and | Emamectin |
| B-23 | 42 | and | Endosulfan |
| B-24 | 42 | and | Esfenvalerate |
| B-25 | 42 | and | Ethiprole |
| B-26 | 42 | and | Fenothiocarb |
| B-27 | 42 | and | Fenoxycarb |
| B-28 | 42 | and | Fenvalerate |
| B-29 | 42 | and | Fipronil |
| B-30 | 42 | and | Flonicamid |
| B-31 | 42 | and | Flubendiamide |
| B-32 | 42 | and | Flufenoxuron |
| B-33 | 42 | and | Hexaflumuron |
| B-34 | 42 | and | Hydramethylnon |
| B-35 | 42 | and | Imidacloprid |
| B-36 | 42 | and | Indoxacarb |
| B-37 | 42 | and | Lambda-cyhalothrin |
| B-38 | 42 | and | Lufenuron |
| B-39 | 42 | and | Metaflumizone |
| B-40 | 42 | and | Methomyl |
| B-41 | 42 | and | Methoprene |
| B-42 | 42 | and | Methoxyfenozide |
| B-43 | 42 | and | Nitenpyram |
| B-44 | 42 | and | Nithiazine |
| B-45 | 42 | and | Novaluron |
| B-46 | 42 | and | Oxamyl |
| B-47 | 42 | and | Pymetrozine |
| B-48 | 42 | and | Pyrethrin |
| B-49 | 42 | and | Pyridaben |
| B-50 | 42 | and | Pyridalyl |
| B-51 | 42 | and | Pyriproxyfen |
| B-52 | 42 | and | Ryanodine |
| B-53 | 42 | and | Spinetoram |
| B-54 | 42 | and | Spinosad |
| B-55 | 42 | and | Spirodiclofen |
| B-56 | 42 | and | Spiromesifen |
| B-57 | 42 | and | Tebufenozide |
| B-58 | 42 | and | Thiacloprid |
| B-59 | 42 | and | Thiamethoxam |
| B-60 | 42 | and | Thiodicarb |
| B-61 | 42 | and | Thiosultap-sodium |
| B-62 | 42 | and | Tralomethrin |
| B-63 | 42 | and | Triazamate |
| B-64 | 42 | and | Triflumuron |
| B-65 | 42 | and | *Bacillus thuringiensis* |
| B-66 | 42 | and | *Bacillus thuringiensis* delta-endotoxin |
| B-67 | 42 | and | NPV (e.g., Gemstar) |
| C-1 | 107 | and | Abamectin |
| C-2 | 107 | and | Acetamiprid |
| C-3 | 107 | and | Amitraz |
| C-4 | 107 | and | Avermectin |
| C-5 | 107 | and | Azadirachtin |
| C-6 | 107 | and | Beta-cyfluthrin |
| C-7 | 107 | and | Bifenthrin |
| C-8 | 107 | and | Buprofezin |
| C-9 | 107 | and | Cartap |
| C-10 | 107 | and | Chlorantraniliprole |
| C-11 | 107 | and | Chlorfenapyr |
| C-12 | 107 | and | Chlorpyrifos |
| C-13 | 107 | and | Clothianidin |
| C-14 | 107 | and | Cyfluthrin |
| C-15 | 107 | and | Cyhalothrin |
| C-16 | 107 | and | Cypermethrin |
| C-17 | 107 | and | Cyromazine |
| C-18 | 107 | and | Deltamethrin |
| C-19 | 107 | and | Dieldrin |
| C-20 | 107 | and | Dinotefuran |
| C-21 | 107 | and | Diofenolan |
| C-22 | 107 | and | Emamectin |

TABLE B-continued

| Mixture No. | Comp. No. | and | Invertebrate Pest Control Agent |
|---|---|---|---|
| C-23 | 107 | and | Endosulfan |
| C-24 | 107 | and | Esfenvalerate |
| C-25 | 107 | and | Ethiprole |
| C-26 | 107 | and | Fenothiocarb |
| C-27 | 107 | and | Fenoxycarb |
| C-28 | 107 | and | Fenvalerate |
| C-29 | 107 | and | Fipronil |
| C-30 | 107 | and | Flonicamid |
| C-31 | 107 | and | Flubendiamide |
| C-32 | 107 | and | Flufenoxuron |
| C-33 | 107 | and | Hexaflumuron |
| C-34 | 107 | and | Hydramethylnon |
| C-35 | 107 | and | Imidacloprid |
| C-36 | 107 | and | Indoxacarb |
| C-37 | 107 | and | Lambda-cyhalothrin |
| C-38 | 107 | and | Lufenuron |
| C-39 | 107 | and | Metaflumizone |
| C-40 | 107 | and | Methomyl |
| C-41 | 107 | and | Methoprene |
| C-42 | 107 | and | Methoxyfenozide |
| C-43 | 107 | and | Nitenpyram |
| C-44 | 107 | and | Nithiazine |
| C-45 | 107 | and | Novaluron |
| C-46 | 107 | and | Oxamyl |
| C-47 | 107 | and | Pymetrozine |
| C-48 | 107 | and | Pyrethrin |
| C-49 | 107 | and | Pyridaben |
| C-50 | 107 | and | Pyridalyl |
| C-51 | 107 | and | Pyriproxyfen |
| C-52 | 107 | and | Ryanodine |
| C-53 | 107 | and | Spinetoram |
| C-54 | 107 | and | Spinosad |
| C-55 | 107 | and | Spirodiclofen |
| C-56 | 107 | and | Spiromesifen |
| C-57 | 107 | and | Tebufenozide |
| C-58 | 107 | and | Thiacloprid |
| C-59 | 107 | and | Thiamethoxam |
| C-60 | 107 | and | Thiodicarb |
| C-61 | 107 | and | Thiosultap-sodium |
| C-62 | 107 | and | Tralomethrin |
| C-63 | 107 | and | Triazamate |
| C-64 | 107 | and | Triflumuron |
| C-65 | 107 | and | *Bacillus thuringiensis* |
| C-66 | 107 | and | *Bacillus thuringiensis* delta-endotoxin |
| C-67 | 107 | and | NPV (e.g., Gemstar) |
| D-1 | 208 | and | Abamectin |
| D-2 | 208 | and | Acetamiprid |
| D-3 | 208 | and | Amitraz |
| D-4 | 208 | and | Avermectin |
| D-5 | 208 | and | Azadirachtin |
| D-6 | 208 | and | Beta-cyfluthrin |
| D-7 | 208 | and | Bifenthrin |
| D-8 | 208 | and | Buprofezin |
| D-9 | 208 | and | Cartap |
| D-10 | 208 | and | Chlorantraniliprole |
| D-11 | 208 | and | Chlorfenapyr |
| D-12 | 208 | and | Chlorpyrifos |
| D-13 | 208 | and | Clothianidin |
| D-14 | 208 | and | Cyfluthrin |
| D-15 | 208 | and | Cyhalothrin |
| D-16 | 208 | and | Cypermethrin |
| D-17 | 208 | and | Cyromazine |
| D-18 | 208 | and | Deltamethrin |
| D-19 | 208 | and | Dieldrin |
| D-20 | 208 | and | Dinotefuran |
| D-21 | 208 | and | Diofenolan |
| D-22 | 208 | and | Emamectin |
| D-23 | 208 | and | Endosulfan |
| D-24 | 208 | and | Esfenvalerate |
| D-25 | 208 | and | Ethiprole |
| D-26 | 208 | and | Fenothiocarb |
| D-27 | 208 | and | Fenoxycarb |
| D-28 | 208 | and | Fenvalerate |
| D-29 | 208 | and | Fipronil |
| D-30 | 208 | and | Flonicamid |
| D-31 | 208 | and | Flubendiamide |
| D-32 | 208 | and | Flufenoxuron |
| D-33 | 208 | and | Hexaflumuron |
| D-34 | 208 | and | Hydramethylnon |
| D-35 | 208 | and | Imidacloprid |
| D-36 | 208 | and | Indoxacarb |
| D-37 | 208 | and | Lambda-cyhalothrin |
| D-38 | 208 | and | Lufenuron |
| D-39 | 208 | and | Metaflumizone |
| D-40 | 208 | and | Methomyl |
| D-41 | 208 | and | Methoprene |
| D-42 | 208 | and | Methoxyfenozide |
| D-43 | 208 | and | Nitenpyram |
| D-44 | 208 | and | Nithiazine |
| D-45 | 208 | and | Novaluron |
| D-46 | 208 | and | Oxamyl |
| D-47 | 208 | and | Pymetrozine |
| D-48 | 208 | and | Pyrethrin |
| D-49 | 208 | and | Pyridaben |
| D-50 | 208 | and | Pyridalyl |
| D-51 | 208 | and | Pyriproxyfen |
| D-52 | 208 | and | Ryanodine |
| D-53 | 208 | and | Spinetoram |
| D-54 | 208 | and | Spinosad |
| D-55 | 208 | and | Spirodiclofen |
| D-56 | 208 | and | Spiromesifen |
| D-57 | 208 | and | Tebufenozide |
| D-58 | 208 | and | Thiacloprid |
| D-59 | 208 | and | Thiamethoxam |
| D-60 | 208 | and | Thiodicarb |
| D-61 | 208 | and | Thiosultap-sodium |
| D-62 | 208 | and | Tralomethrin |
| D-63 | 208 | and | Triazamate |
| D-64 | 208 | and | Triflumuron |
| D-65 | 208 | and | *Bacillus thuringiensis* |
| D-66 | 208 | and | *Bacillus thuringiensis* delta-endotoxin |
| D-67 | 208 | and | NPV (e.g., Gemstar) |
| E-1 | 65 | and | Abamectin |
| E-2 | 65 | and | Acetamiprid |
| E-3 | 65 | and | Amitraz |
| E-4 | 65 | and | Avermectin |
| E-5 | 65 | and | Azadirachtin |
| E-6 | 65 | and | Beta-cyfluthrin |
| E-7 | 65 | and | Bifenthrin |
| E-8 | 65 | and | Buprofezin |
| E-9 | 65 | and | Cartap |
| E-10 | 65 | and | Chlorantraniliprole |
| E-11 | 65 | and | Chlorfenapyr |
| E-12 | 65 | and | Chlorpyrifos |
| E-13 | 65 | and | Clothianidin |
| E-14 | 65 | and | Cyfluthrin |
| E-15 | 65 | and | Cyhalothrin |
| E-16 | 65 | and | Cypermethrin |
| E-17 | 65 | and | Cyromazine |
| E-18 | 65 | and | Deltamethrin |
| E-19 | 65 | and | Dieldrin |
| E-20 | 65 | and | Dinotefuran |
| E-21 | 65 | and | Diofenolan |
| E-22 | 65 | and | Emamectin |
| E-23 | 65 | and | Endosulfan |
| E-24 | 65 | and | Esfenvalerate |
| E-25 | 65 | and | Ethiprole |
| E-26 | 65 | and | Fenothiocarb |
| E-27 | 65 | and | Fenoxycarb |
| E-28 | 65 | and | Fenvalerate |
| E-29 | 65 | and | Fipronil |
| E-30 | 65 | and | Flonicamid |
| E-31 | 65 | and | Flubendiamide |
| E-32 | 65 | and | Flufenoxuron |
| E-33 | 65 | and | Hexaflumuron |
| E-34 | 65 | and | Hydramethylnon |
| E-35 | 65 | and | Imidacloprid |
| E-36 | 65 | and | Indoxacarb |
| E-37 | 65 | and | Lambda-cyhalothrin |
| E-38 | 65 | and | Lufenuron |

TABLE B-continued

| Mixture No. | Comp. No. | and | Invertebrate Pest Control Agent |
|---|---|---|---|
| E-39 | 65 | and | Metaflumizone |
| E-40 | 65 | and | Methomyl |
| E-41 | 65 | and | Methoprene |
| E-42 | 65 | and | Methoxyfenozide |
| E-43 | 65 | and | Nitenpyram |
| E-44 | 65 | and | Nithiazine |
| E-45 | 65 | and | Novaluron |
| E-46 | 65 | and | Oxamyl |
| E-47 | 65 | and | Pymetrozine |
| E-48 | 65 | and | Pyrethrin |
| E-49 | 65 | and | Pyridaben |
| E-50 | 65 | and | Pyridalyl |
| E-51 | 65 | and | Pyriproxyfen |
| E-52 | 65 | and | Ryanodine |
| E-53 | 65 | and | Spinetoram |
| E-54 | 65 | and | Spinosad |
| E-55 | 65 | and | Spirodiclofen |
| E-56 | 65 | and | Spiromesifen |
| E-57 | 65 | and | Tebufenozide |
| E-58 | 65 | and | Thiacloprid |
| E-59 | 65 | and | Thiamethoxam |
| E-60 | 65 | and | Thiodicarb |
| E-61 | 65 | and | Thiosultap-sodium |
| E-62 | 65 | and | Tralomethrin |
| E-63 | 65 | and | Triazamate |
| E-64 | 65 | and | Triflumuron |
| E-65 | 65 | and | *Bacillus thuringiensis* |
| E-66 | 65 | and | *Bacillus thuringiensis* delta-endotoxin |
| E-67 | 65 | and | NPV (e.g., Gemstar) |
| F-1 | 69 | and | Abamectin |
| F-2 | 69 | and | Acetamiprid |
| F-3 | 69 | and | Amitraz |
| F-4 | 69 | and | Avermectin |
| F-5 | 69 | and | Azadirachtin |
| F-6 | 69 | and | Beta-cyfluthrin |
| F-7 | 69 | and | Bifenthrin |
| F-8 | 69 | and | Buprofezin |
| F-9 | 69 | and | Cartap |
| F-10 | 69 | and | Chlorantraniliprole |
| F-11 | 69 | and | Chlorfenapyr |
| F-12 | 69 | and | Chlorpyrifos |
| F-13 | 69 | and | Clothianidin |
| F-14 | 69 | and | Cyfluthrin |
| F-15 | 69 | and | Cyhalothrin |
| F-16 | 69 | and | Cypermethrin |
| F-17 | 69 | and | Cyromazine |
| F-18 | 69 | and | Deltamethrin |
| F-19 | 69 | and | Dieldrin |
| F-20 | 69 | and | Dinotefuran |
| F-21 | 69 | and | Diofenolan |
| F-22 | 69 | and | Emamectin |
| F-23 | 69 | and | Endosulfan |
| F-24 | 69 | and | Esfenvalerate |
| F-25 | 69 | and | Ethiprole |
| F-26 | 69 | and | Fenothiocarb |
| F-27 | 69 | and | Fenoxycarb |
| F-28 | 69 | and | Fenvalerate |
| F-29 | 69 | and | Fipronil |
| F-30 | 69 | and | Flonicamid |
| F-31 | 69 | and | Flubendiamide |
| F-32 | 69 | and | Flufenoxuron |
| F-33 | 69 | and | Hexaflumuron |
| F-34 | 69 | and | Hydramethylnon |
| F-35 | 69 | and | Imidacloprid |
| F-36 | 69 | and | Indoxacarb |
| F-37 | 69 | and | Lambda-cyhalothrin |
| F-38 | 69 | and | Lufenuron |
| F-39 | 69 | and | Metaflumizone |
| F-40 | 69 | and | Methomyl |
| F-41 | 69 | and | Methoprene |
| F-42 | 69 | and | Methoxyfenozide |
| F-43 | 69 | and | Nitenpyram |
| F-44 | 69 | and | Nithiazine |
| F-45 | 69 | and | Novaluron |
| F-46 | 69 | and | Oxamyl |

TABLE B-continued

| Mixture No. | Comp. No. | and | Invertebrate Pest Control Agent |
|---|---|---|---|
| F-47 | 69 | and | Pymetrozine |
| F-48 | 69 | and | Pyrethrin |
| F-49 | 69 | and | Pyridaben |
| F-50 | 69 | and | Pyridalyl |
| F-51 | 69 | and | Pyriproxyfen |
| F-52 | 69 | and | Ryanodine |
| F-53 | 69 | and | Spinetoram |
| F-54 | 69 | and | Spinosad |
| F-55 | 69 | and | Spirodiclofen |
| F-56 | 69 | and | Spiromesifen |
| F-57 | 69 | and | Tebufenozide |
| F-58 | 69 | and | Thiacloprid |
| F-59 | 69 | and | Thiamethoxam |
| F-60 | 69 | and | Thiodicarb |
| F-61 | 69 | and | Thiosultap-sodium |
| F-62 | 69 | and | Tralomethrin |
| F-63 | 69 | and | Triazamate |
| F-64 | 69 | and | Triflumuron |
| F-65 | 69 | and | *Bacillus thuringiensis* |
| F-66 | 69 | and | *Bacillus thuringiensis* delta-endotoxin |
| F-67 | 69 | and | NPV (e.g., Gemstar) |

The specific mixtures listed in Table B typically combine a compound of Formula 1 with the other invertebrate pest agent in the ratios specified in Table A.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one; additional biologically active compound or agent include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment Progress and Prospects*, 1994 BCPC Monograph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic applications include protecting an animal, particularly a vertebrate, more particularly a homeothermic vertebrate (e.g., mammal or bird) and most particularly a mammal, from an invertebrate parasitic pest by administering a parasiticidally effective (i.e. biologically effective) amount of a compound of the invention, typically in the form of a composition formulated for veterinary use, to the animal to be protected. Therefore of note is a method for protecting an animal comprising administering to the animal a parasiticidally effective amount of a compound of the invention. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal. Examples of invertebrate parasitic pests controlled by administering a parasiticidally effective amount of a compound of the invention to an animal to be protected include ectoparasites (arthropods, acarines, etc) and endoparasites (helminths, e.g., nematodes, trematodes, cestodes, acanthocephalans, etc.). In particular, the compounds of this invention are effective against ectoparasites including: flies such as *Haemarobia* (*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucitia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lices such as *Bovicola* (*Damalinia*) *bovis, Bovicola equi, Haematopinus asini, Felicola subrostratus, Heterodoxus spiniger; Lignonathus setosus* and *Trichodectes canis*; keds such as *Melophagus ovinus*; mites such as *Psoroptes* spp., *Sarcoptes scabei, Chorioptes bovis, Demodex equi, Cheyletielta* spp., *Noloedres cati, Trombicula* spp. and *Otodectes cyanotis* (ear mites); ticks such as *Ixodes* spp., *Boophilus* spp., *Rhipicephalus* spp., *Amblyomna* spp., *Dermacentor* spp., *Hyalomma* spp. and *Haemaphysalis* spp.; and fleas such as *Ctenocephalides felis* (cat flea) and *Ctenocephalides canis* (dog flea).

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal), implants; by nasal administration; by topical administration, for example, in the form of immersion or dipping, spraying, washing, coating with powder, or application to a small area of the animal, and through articles such as neck collars, ear tags, tail bands, limb bands or halters which comprise compounds or compositions of the present invention.

Typically a parasiticidal composition according to the present invention comprises a mixture of a compound of Formula 1, an N-oxide or a salt thereof, with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of the invention and at least one carrier.

For parenteral administration including intravenous, intramuscular and subcutaneous injection, a compound of the present invention can be formulated in suspension, solution or emulsion in oily or aqueous vehicles, and may contain adjuncts such as suspending, stabilizing and/or dispersing agents. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation.

For oral administration including solutions (the most readily available form for absorption), emulsions, suspensions, pastes, gels, capsules, tablets, boluses powders, granules, rumen-retention and feed/water/lick blocks, a compound of the present invention can be formulated with binders/fillers known in the art to be suitable for oral administration compositions, such as sugars (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthangum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

Compounds of the present invention have been discovered to have favorable pharmacokinetic and pharmacodynamic properties providing systemic availability from oral administration and ingestion. Therefore after ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present invention and one or more topically suitable carriers. In applications of a parasiticidal composition topically to the exterior of an animal as a line or spot (i.e. "spot-on" treatment), the active ingredient is expected to migrate over the surface of the active to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Solvents commonly used as carriers, in such formulations include propylene glycol, paraffins, aromatics, esters such as isopropyl myristate, glycol ethers, and alcohols such as ethanol and n-propanol.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a compound of Formula 1, an N-oxide or a salt thereof, is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation.

For oral administration to homeothermic animals, the daily dosage of a compound of the present invention typically ranges from about 0.01 mg/kg to about 100 mg/kg, more typically from about 0.5 mg/kg to about 100 mg/kg, of animal body weight. For topical (e.g., dermal) administration, dips and sprays typically contain from about 0.5 ppm to about 5000 ppm, more typically from about 1 ppm to about 3000 ppm, of a compound of the present invention.

The following abbreviations are used in the Index Tables A-D which follow: t is tertiary, s is secondary, n is normal, i is iso, c is cyclo, Me is methyl, Et is ethyl, Pr is propyl, i-Pr is isopropyl, Bu is butyl, c-Pr is cyclopropyl, t-Bu is tert-butyl, Ph is phenyl, OMe is methoxy, $CF_3$ means trifluoromethyl, —CN is cyano and —$NO_2$ is nitro. The abbreviation "Ex." stands for "Example" and is followed by a number indicating in which example the compound is prepared. In Index Tables A, B and C, $(R^2)_k$ refers to the combination of $(R^2)_n$ as shown with instances of $CR^2$ for $B^1$, $B^2$ and $B^3$, and thus k is 1, 2, 3, 4 or 5 for Index Tables A, B and C.

INDEX TABLE A

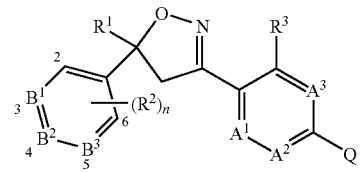

wherein $B^1$, $B^2$ and $B^3$ are $CR^2$, and $R^3$ is H.

| Compound | $R^1$ | $(R^2)_k$ | $A^1$ | $A^2$ | $A^3$ | Q | m.p. (° C.) |
|---|---|---|---|---|---|---|---|
| 1 (Ex. 1) | $CF_3$ | 3-Cl, 5-Cl | CH | CH | CH | 1H-pyrazol-1-yl | 174-175* |
| 2 (Ex. 2) | $CF_3$ | 3-Cl, 5-Cl | CH | C-Me | CH | 1H-pyrazol-1-yl | * |
| 3 (Ex. 3) | $CF_3$ | 3-Cl, 5-Cl | CH | CH | CH | 2-pyridinyl | * |
| 4 | $CF_3$ | 3-Cl, 5-Cl | CH | CH | CH | 5-$CF_3$-1H-imidazol-2-yl | 135-136* |
| 5 | $CF_3$ | 3-Cl, 5-Cl | CH | CH | CH | 1H-imidazol-2-yl | 175-176 |
| 6 | $CF_3$ | 3-Cl, 5-Cl | CH | CH | CH | 4-(1,1-dimethylethyl)-2-thiazolyl | * |
| 7 | $CF_3$ | 3-Cl, 5-Cl | CH | CH | CH | 1,2,3-thiadiazol-4-yl | 178-179 |
| 8 | $CF_3$ | 3-Cl, 5-Cl | CH | C-Me | CH | 3-($CF_3$)-1H-pyrazol-1-yl | * |
| 9 | $CF_3$ | 3-Cl, 5-Cl | CH | CH | CH | 1H-1,2,4-triazol-1-yl | 181-182 |
| 10 | $CF_3$ | 3-Cl, 5-Cl | CH | CH | CH | 2-thienyl | 189-190 |
| 11 | $CF_3$ | 3-Cl, 5-Cl | CH | CH | CH | 4-Br-3-Me-1H-pyrazol-1-yl | 129-131 |
| 12 | $CF_3$ | 3-Cl, 5-Cl | CH | CH | CH | 3-(4-pyridinyl)-1H-pyrazol-1-yl | * |
| 13 | $CF_3$ | 3-Cl, 5-Cl | CH | CH | CH | 4-iodo-1H-pyrazol-1-yl | 174175 |
| 14 | $CF_3$ | 3-Cl, 5-Cl | CH | C-Me | CH | 1H-1,2,4-triazol-1-yl | 126-127 |
| 15 | $CF_3$ | 3-Cl, 5-Cl | CH | CH | CH | (4-Cl-Ph)-1H-pyrazol-1-yl | 214-215 |
| 16 | $CF_3$ | 3-Cl, 5-Cl | CH | C—F | CH | 1H-1,2,4-triazol-1-yl | 135-137 |
| 17 | $CF_3$ | 3-Cl, 5-Cl | CH | C—F | CH | 1H-pyrazol-1-yl | 115-123 |
| 18 | $CF_3$ | 3-Cl, 5-Cl | CH | C-Me | CH | 1H-1,2,3-triazol-1-yl | * |
| 19 | $CF_3$ | 3-Cl, 5-Cl | CH | CH | CH | 1H-1,2,3-triazol-1-yl | 131-132 |
| 20 | $CF_3$ | 3-Cl, 5-Cl | CH | CH | CH | 3-($CF_3$)-1H-1,2,4-triazol-1-yl | * |
| 21 | $CF_3$ | H | CH | CH | CH | 1H-1,2,4-triazol-1-yl | 133-134 |

INDEX TABLE A-continued

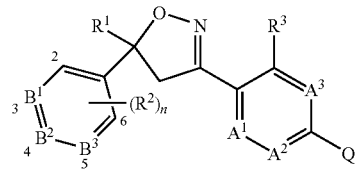

wherein $B^1$, $B^2$ and $B^3$ are $CR^2$, and $R^3$ is H.

| Compound | $R^1$ | $(R^2)_k$ | $A^1$ | $A^2$ | $A^3$ | Q | m.p. (° C.) |
|---|---|---|---|---|---|---|---|
| 22 | $CF_3$ | 3-Cl, 4-Cl | CH | CH | CH | 1H-1,2,4-triazol-1-yl | 166-167 |
| 23 | $CF_3$ | 3-Cl | CH | CH | CH | 1H-1,2,4-triazol-1-yl | 142-143 |
| 24 | $CF_3$ | 3-$CF_3$, 5-$CF_3$ | CH | CH | CH | 1H-1,2,4-triazol-1-yl | 116-117 |
| 25 | $CF_3$ | 3-F, 5-F | CH | CH | CH | 1H-1,2,4-triazol-1-yl | 164-165 |
| 26 | $CF_3$ | 3-Br, 5-Br | CH | CH | CH | 1H-1,2,4-triazol-1-yl | 165-366 |
| 27 | $CF_3$ | 2-Cl | CH | CH | CH | 1H-1,2,4-triazol-1-yl | 178-179 |
| 28 | $CF_3$ | 3-Cl, 6-F | CH | CH | CH | 1H-1,2,4-triazol-1-yl | * |
| 29 | $CF_3$ | 3-Cl, 5-Cl | CH | CH | CH | 1H-pyrrol-1-yl | 202-203 |
| 30 | $CF_3$ | 3-Cl, 5-Cl | C—Cl | CH | CH | 1H-1,2,4-triazol-1-yl | 141-143 |
| 31 | $CF_3$ | 3-Cl, 5-Cl | CH | C—$CF_3$ | CH | 1H-1,2,4-triazal-1-yl | * |
| 32 | $CF_3$ | 3-Cl, 4-F | CH | CH | CH | 1H-1,2,4-triazol-1-yl | 170-171 |
| 33 | $CF_3$ | 3-Cl, 5-Cl | CH | CH | CH | 4-morpholinyl | 139-140 |
| 34 | Et | 3-Cl, 5-Cl | CH | CH | CH | 1H-1,2,4-triazol-1-yl | 134-135 |
| 35 | Me | 3-Cl, 5-Cl | CH | CH | CH | 1H-1,2,4-triazol-1-yl | 151-152 |
| 36 | $CF_3$ | 3Cl, 5-Cl | CH | C—Cl | CH | 1H-1,2,4-triazol-1-yl | * |
| 37 | $CF_3$ | 3-Cl, 5-Cl | CH | C—Cl | CH | 1H-1,2,3-triazol-1-yl | 164-165 |
| 38 | $CF_3$ | 3-Cl, 5-Cl | CH | C—$NO_2$ | CH | 1H-1,2,4-triazol-1-yl | 61-62 |
| 39 | $CF_3$ | 3-Cl, 5-Cl | C—Cl | CH | CH | 1H-pyrazol-1-yl | 116-118 |
| 40 | $CF_3$ | 3-Cl, 5-Cl | CH | C—$NO_2$ | CH | 1H-pyrazol-1-yl | 141-142 |
| 41 | $CF_3$ | 3-Cl, 5-Cl | CH | CH | CH | 4-(2-pyridinyl)-1-piperazinyl | 178-179 |
| 42 | $CF_3$ | 3-Cl, 5-Cl | CH | C—CN | CH | 1H-1,2,4-triazol-1-yl | 64-66 |
| 43** | $CF_3$ | 3-Cl, 5-Cl | CH | CH | CH | 1H-1,2,4-triazol-1-yl | * |
| 44** | $CF_3$ | 3-Cl, 5-Cl | CH | CH | CH | 1H-1,2,4-triazol-1-yl | * |
| 45 | $CF_3$ | 3-Me, 5-Me | CH | CH | CH | 1H-1,2,4-triazol-1-yl | 156-157 |
| 46 | $CF_3$ | 3-Br, 5-Me | CH | CH | CH | 1H-1,2,4-triazol-1-yl | 187-188 |
| 47 | $CF_3$ | 3-Br, 5-F | CH | CH | CH | 1H-1,2,4-triazol-1-yl | 144145 |
| 48 | $CF_3$ | 3-Br, 5-OMe | CH | CH | CH | 1H-1,2,4-triazol-1-yl | 130-131 |
| 49 | —CN | 3-Cl, 4-Cl | CH | CH | CH | 1H-1,2,4-triazol-1-yl | * |
| 50 | $CF_3$ | 3-CN | CH | CH | CH | 1H-1,2,4-triazol-1-yl | 186-187 |
| 51 | $CF_3$ | 3-CN, 5-Me | CH | CH | CH | 1H-1,2,4-triazol-1-yl | 234-235 |
| 52 | $CF_3$ | 3-CN, 5-CN | CH | CH | CH | 1H-1,2,4-biazol-1-yl | 223-224 |
| 53 | $CF_3$ | 3-CN, 4-F | CH | CH | CH | 1H-1,2,4-triazol-1-yl | 188-189 |
| 54 | $CF_3$ | 2-Cl, 3-Cl | CH | CH | CH | 1H-1,2,4-triazol-1-yl | 270-171 |
| 55 | $CF_3$ | 3-OMe, 4-OMe | CH | CH | CH | 1H-1,2,4-triazol-1-yl | 169-170 |
| 56 | $CF_3$ | 3-Br, 2-F | CH | CH | CH | 1H-1,2,4-triazol-1-yl | 1.67-168 |
| 57 | $CF_3$ | 3-Cl, 5-Cl | CH | C—CN | CH | 1H-pyrazol-1-yl | 164-165 |
| 58 | $CF_3$ | 3-Cl, 5-Cl | CH | C—$NH_2$ | CH | 1H-1,2,4-triazol-1-yl | 240-241 |
| 59 | $CF_3$ | 3-Cl, 5-Cl | CH | C—$NHCOCH_3$ | CH | 1H-1,2,4-tnazal-1-yl | 221-222 |
| 60 | $CF_3$ | 3-Cl, 5-Cl | CH | C—$NHCO_2CH_3$ | CH | 1H-1,2,4-triazol-1-yl | 91-92 |
| 61 | $CF_3$ | 3-Cl, 5-Cl | CH | C—CN | CH | 1H-imidazol-1-yl | 150-153 |
| 62 | $CF_3$ | 3-Cl, 5-Cl | CH | C—OMe | CH | 1H-1,2,4-triazol-1-yl | 179-180 |
| 63 | $CF_3$ | 3-Cl, 5-Cl | CH | C—Br | CH | 1H-1,2,4-triazol-1-yl | 72-73 |
| 64 | $CF_3$ | 3-Cl, 5-Cl | CH | C—$CONH_2$ | CH | 1H-1,2,4-triazol-1-yl | * |
| 65 | $CF_3$ | 3-Cl, 5-Cl | CH | C—$CSNH_2$ | CH | 1H-1,2,4-triazol-1-yl | 139-140 |
| 66 | $CF_3$ | 3-Cl, 5-Cl | CH | C—CN | CH | 5-(Me)-1H-1,2,4-triazol-1-yl | * |
| 67 | $CF_3$ | 3-Cl, 5-Cl | CH | C—CN | CH | 3-($CO_2Me$)-1H-1,2,4-triazol-1-yl | 102-103 |
| 68 | $CF_3$ | 3-Cl, 5-Cl | CH | C—CN | CH | 3-(CN)-1H-1,2,4-triazol-1-yl | 80-81 |
| 69 | $CF_3$ | 3-Cl, 5-Cl | CH | C—CN | CH | 3-($NH_2$)-1H-1,2,4-triazol-1-yl | 102-103 |
| 70 | $CF_3$ | 3-Cl, 5-Cl | CH | C—CN | CH | 3-(Br)-1H-1,2,4-triazol-1-yl | 84-85 |
| 71 | $CF_3$ | 3-Cl, 5-Cl | CH | C—CN | CH | 2H-tetrazol-2-yl | 143-153 |
| 72 | $CF_3$ | 3-Cl, 5-Cl | CH | C—CN | CH | 1H-tetrazol-1-yl | 84-85 |
| 73 | $CF_3$ | 3-Cl, 5-Cl | CH | C—CN | CH | 3-(4-pyridinyl)-1H-pyrazol-1-yl | 203-204 |
| 74 | $CF_3$ | 3-Cl, 5-Cl | CH | C—$CO_2CH_3$ | CH | 1H-1,2,4-triazol-1-yl | * |
| 75 | $CF_3$ | 3-Cl, 5-Cl | CH | C—Br | CH | 5-($NH_2$)-1H-1,2,4-triazol-1-yl | * |
| 76 | $CF_3$ | 3-Cl, 5-Cl | CH | C—I | CH | 1H-1,2,4-triazol-1-yl | * |
| 77 | $CF_3$ | 3-Cl, 5-Cl | CH | C—CN | CH | 3-(2-pyridinyl)-1H-1,2,4-triazol-1-yl | 90-91 |
| 78 | $CF_3$ | 3-Cl, 5-Cl | CH | C—Br | CH | 3-(2-pyridinyl)-1H-1,2,4-triazol-1-yl | 71-72 |
| 79 | $CF_3$ | 3-Cl, 5-Cl | CH | CH | CH | 5-(Br)-1H-1,2,4-triazol-1-yl | * |
| 80 | $CF_3$ | 3-Cl, 5-Cl | CH | CH | CH | 4H-1,2,4-triazol-4-yl | >250 |
| 81 | $CF_3$ | 3-Cl, 5-Cl | CH | CH | N | 1H-1,2,4-triazol-1-yl | 160-162 |
| 82 | $CF_3$ | 3-Cl, 5-Cl | CH | C—Cl | N | 1H-1,2,4-triazol-1-yl | 144-145 |
| 83 | $CF_3$ | 3-Cl, 5-Cl | CH | CH | CH | 3-($CF_3$)-1H-pyrazol-1-yl | 110-112 |
| 84 | $CF_3$ | 3-Cl, 5-Cl | CH | C-Me | CH | 5-(2-pyridinyl)-1H-1,2,4-triazol-3-yl | 232-233 |
| 85 | $CF_3$ | 3-Cl, 5-Cl | CH | CH | CH | 4-(2-pyridinyl)-2-thiazolyl | 198-199 |
| 86 | $CF_3$ | 3-Cl, 5-Cl | CH | CH | CH | 5-pyrimidinyl | * |
| 87 | $CF_3$ | 3-Cl, 5-Cl | CH | CH | CH | 2-pyrazinyl | * |

INDEX TABLE A-continued

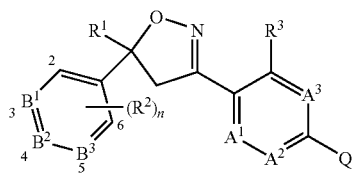

wherein $B^1$, $B^2$ and $B^3$ are $CR^2$, and $R^3$ is H.

| Compound | $R^1$ | $(R^2)_k$ | $A^1$ | $A^2$ | $A^3$ | Q | m.p. (° C.) |
|---|---|---|---|---|---|---|---|
| 88 | $CF_3$ | 3-Cl, 5-Cl | CH | CH | CH | 3-pyridinyl | * |
| 89 | $CF_3$ | 3-Br, 5-Br | CH | C—CN | CH | 1H-1,2,4-triazol-1-yl | * |

*See Index Table E for $^1$H NMR data.

**Compounds 43 and 44 are enantiomeric isomers separated by chiral column chromatography, though the absolute configuration of each compound has not been determined yet.

INDEX TABLE B

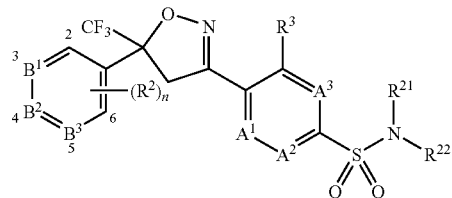

wherein $B^1$, $B^2$ and $B^3$ are $CR^2$, and $R^3$ is H.

| Compound | $(R^2)_k$ | $A^1$ | $A^2$ | $A^3$ | $R^{21}$ | $R^{22}$ | m.p. (° C.) |
|---|---|---|---|---|---|---|---|
| 101 | H | CH | C-Me | CH | H | i-Pr | * |
| 102 | 3-Cl, 5-Cl | CH | C-Me | CH | H | i-Pr | * |
| 103 | 3-Cl, 5-Cl | CH | C-Me | CH | H | $CH_2CF_3$ | * |
| 104 | H | CH | C-Me | CH | H | $CH_2CF_3$ | * |
| 105 | 3-Cl, 5-Cl | CH | C-Me | CH | H | $CH(CH_3)CH_2CH_3$ | * |
| 106 | 3-Cl, 4-Cl | CH | C-Me | CH | H | $CH(CH_3)CH_2CH_3$ | * |
| 107 | 3-Cl, 5-Cl | CH | C-Me | CH | H | $CH_2$-c-Pr | 105-106 |
| 108 | 3-Cl, 5-Cl | CH | C-Me | CH | Me | Me | 142-143 |
| 109 | 3-Cl, 5-Cl | CH | C-Me | CH | H | $CH_2CN$ | 64-65 |
| 110 | 3-Cl, 5-Cl | CH | C-Me | CH | Me | $CH_2Ph$ | * |
| 111 | 3-Cl, 5-Cl | CH | C-Me | CH | H | Me | 140-142 |
| 112 | 3-Cl, 5-Cl | CH | C-Me | CH | H | $C(CH_3)_2CH_2SCH_3$ | 88-89 |
| 113 (Ex.4) | 3-Cl, 5-Cl | CH | C-Me | CH | H | $CH_2$-2-pyridinyl | 57-58 |
| 114 | 3-Cl, 5-Cl | CH | CH | CH | H | $CH_2$-2-pyridinyl | * |
| 115 | 3-Cl,5-Cl | CH | CH | CH | H | i-Pr | 133-134 |
| 116 | 3-Cl, 5-Cl | CH | CH | CH | H | $CH_2CN$ | 113-114 |
| 117 | 3-Cl, 5-Cl | CH | CH | CH | H | $CH_2CF_3$ | 154-155 |
| 118 | 3-Cl, 5-Cl | CH | CH | CH | H | Me | 58-59 |
| 119 | 3-Cl, 5-Cl | CH | C-Me | CH | H | H | 129-130 |
| 120 | 3-Cl, 5-Cl | CH | C-Me | CH | H | $CH_2C$≡CH | * |
| 121 | 3-Cl, 5-Cl | CH | C-Me | CH | H | $CH_2C$=$CH_2$ | 73-74 |
| 122 | 3-Cl, 5-Cl | CH | C-Me | CH | H | n-Pr | 101-102 |
| 123 | 3-Cl, 5-Cl | CH | C-Me | CH | H | Et | 105-106 |
| 124 | 3-Cl, 5-Cl | CH | CH | N | Me | Me | 137-138 |
| 125 | 3-Cl, 5-Cl | CH | C—CN | CH | Me | Me | 197-198 |

*See Index Table E for $^1$H NMR data.

INDEX TABLE C

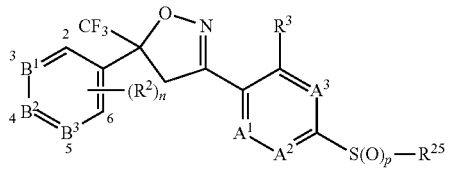

wherein $B^1$, $B^2$ and $B^3$ are $CR^2$, and $R^3$ is H.

| Compound | $(R^2)_k$ | $A^1$ | $A^2$ | $A^3$ | $R^{25}$ | p | m.p. (°C.) |
|---|---|---|---|---|---|---|---|
| 201 | H | CH | CH | CH | Me | 2 | 164-166 |
| 202 | 3-Cl, 5-Cl | CH | CH | CH | CH$_2$-Ph | 0 | 108-109 |
| 203 | 3-Cl, 5-Cl | CH | C—NO$_2$ | CH | CH$_2$-Ph | 0 | 106-108 |
| 204 | 3-Cl, 5-Cl | CH | CH | N | CH$_2$-Ph | 0 | 110-111 |
| 205 | 3-Cl, 5-Cl | CH | C—Br | CH | Me | 0 | * |
| 206 (Ex. 5) | 3-Cl, 5-Cl | CH | C—CN | CH | Me | 0 | ** |
| 207 | 3-Cl, 5-Cl | CH | C—CN | CH | Me | 1 |  |
| 208 (Ex. 6) | 3-Cl, 5-Cl | CH | C—CN | CH | Me | 2 | ** |

INDEX TABLE C-continued

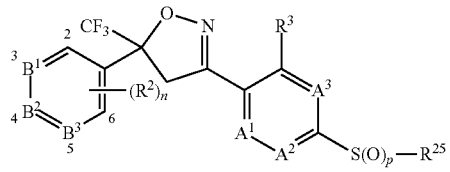

wherein $B^1$, $B^2$ and $B^3$ are $CR^2$, and $R^3$ is H.

| Compound | $(R^2)_k$ | $A^1$ | $A^2$ | $A^3$ | $R^{25}$ | p | m.p. (°C.) |
|---|---|---|---|---|---|---|---|
| 209 (Ex. 7) | 3-Cl, 5-Cl | CH | CH | CH | Me | 2 | ** |
| 210 | 3-Cl, 5-Cl | CH | C—CN | CH | Et | 0 | * |
| 211 | 3-Cl, 5-Cl | CH | C—CN | CH | Et | 2 | * |
| 212 | 3-Cl, 5-Cl | CH | C—Br | CH | Me | 2 | * |
| 213 | 3-Cl, 5-Cl | CH | C-Me | CH | Me | 2 | * |
| 214 | 3-Cl, 5-Cl | CH | C—CN | CH | CH$_2$CF$_3$ | 2 | * |

*See Index Table E for $^1$H NMR data.
**See the specific Example for $^1$H NMR data.

INDEX TABLE D

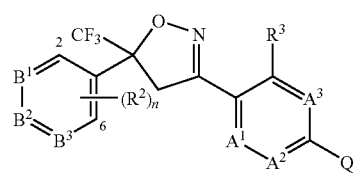

wherein $R^3$ is H.

| Compound | $B^1$ | $B^2$ | $B^3$ | $(R^2)_n$ | $A^1$ | $A^2$ | $A^3$ | Q | m.p. (°C.) |
|---|---|---|---|---|---|---|---|---|---|
| 301 | C—Cl | N | CH | H | CH | 2-CN | CH | 1H-1,2,4-triazol-1-yl | 181-182 |

INDEX TABLE E

| Compd. No. | $^1$H NMR Data (CDCl$_3$ solution unless indicated otherwise)$^a$ |
|---|---|
| 1 | (DMSO-d$_6$) δ 8.63 (d, 1H), 8.00 (d, 2H) 7.84 (m, 4H), 7.64 (d, 2H), 6.60 (m, 1H), 4.38 (AB quartet, 2H). |
| 2 | δ 7.75 (d, 1H), 7.64 (d, 2H), 7.58 (dd, 1H), 7.52 (d, 2H), 7.43 (m, 2H), 6.48 (t, 1H), 4.11 (d, 1H), 3.73 (d, 1H), 2.34 (s, 3H). |
| 3 | δ 8.8 (m, 1H), 8.05 (m, 2H), 7.8 (m, 3H), 7.76 (d, 2H), 7.2 (d, 2H), 4.2 (d, 1H), 3.8 (d, 1H). |
| 6 | δ 8.01 (d, 2H), 7.64 (d, 2H), 7.70 (d, 2H), 7.53 (s, 2H), 7.43 (s, 1H), 6.95 (s, 1H), 4.11 (d, 1H), 3.72 (d, 1H), 1.40 (s, 9H). |
| 8 | δ 7.65 (m, 2H), 7.58 (d, 2H), 7.50 (s, 2H), 7.41 (s, 1H), 7.40 (m, 1H), 6.72 (s, 1H), 3.70 (d, 1H), 2.29 (s, 3H). |
| 12 | δ 8.35 (d, 1H), 8.22-8.19 (m, 1H), 8.07 (s, 1H), 7.87 (d, 2H), 7.80-7.78 (m, 4H), 7.54 (s, 2H), 7.44 (s, 1H), 6.91 (s, 1H), 4.13 (d, 1H), 3.74 (d, 1H). |
| 18 | δ 7.84 (s, 2H), 7.77 (d, 1H), 7.64 (s, 1H), 7.59 (d, 1H), 7.50 (m, 2H), 7.41 (s, 1H), 7.23 (s, 1H), 4.10 (d, 1H), 3.71 (d, 1H), 2.46 (s, 3H). |
| 20 | δ 8.44 (s, 1H), 8.17 (s, 1H), 7.60 (d, 2H), 7.50 (s, 2H), 7.42 (s, 1H), 6.64 (d, 2H), 4.05 (d, 1H), 3.66 (d, 1H). |
| 28 | δ 8.12-8.09 (m, 3H), 7.59-7.56 (m, 5H), 7.44 (s, 1H), 4.21 (d, 1H), 3.83 (d, 1H). |
| 31 | δ 8.37 (s, 1H), 8.17 (s, 1H), 8.10 (s, 1H), 8.04 (d, 1H), 7.66 (d, 1H), 7.52 (d, 1H), 7.45 (s, 1H), 4.17 (d, 1H), 3.71 (d, 1H). |
| 36 | δ 8.66 (s, 1H), 8.16 (s, 1H), 7.89 (s, 1H), 7.73 (s, 1H), 7.51 (s, 2H), 7.48 (s, 1H), 4.10 (d, 1H), 3.73 (d, 1H). |
| 43 | δ 8.69 (s, 1H), 8.16 (s, 1H), 7.81-7.78 (m, 4H), 7.52 (s, 2H), 7.44 (s, 1H), 4.12 (d, 1H), 3.74 (d, 1H). |
| 44 | δ 8.66 (s, 1H), 8.14 (s, 1H), 7.81-7.78 (m, 4H), 7.53 (s, 2H), 7.44 (s, 1H), 4.13 (d, 1H), 3.74 (d, 1H). |
| 49 | δ 8.686 (s, 1H), 7.86-7.70 (m, 6H), 7.58 (s, 1H), 7.50 (s, 1H), 4.28 (d, 1H), 3.79 (d, 1H). |
| 64 | δ 8.47 (s, 1H), 8.16 (s, 1H), 8.02 (s, 1H), 7.98 (d, 1H), 7.57 (d, 1H), 7.51 (s, 2H), 7.45 (s, 1H), 6.05 (br s, NH), 5.63 (br s, NH), 4.13 (d, 1H), 3.76 (d, 1H). |

INDEX TABLE E-continued

| Compd. No. | $^1$H NMR Data (CDCl$_3$ solution unless indicated otherwise)$^a$ |
|---|---|
| 66 | δ 8.01-8.09 (m, 3H), 7.61 (d, 1H), 7.51 (s, 2H), 7.46 (s, 1H), 4.12 (d, 1H), 3.75 (d, 1H), 2.53 (s, 3H). |
| 74 | δ 8.39 (s, 1H), 8.14 (s, 1H), 8.12 (s, 1H), 8.04 (d, 1H), 7.60 (d, 1H), 7.52 (s, 2H), 7.45 (s, 1H), 4.14 (d, 1H), 3.77 (s, 3H), 3.76 (d, 1H). |
| 75 | δ 8.29 (s, 1H), 7.97 (s, 1H), 7.70 (d, 1H), 7.60 (d, 1H), 7.48 (s, 2H), 7.41 (s, 1H), 4.26 (br s, NH$_2$), 4.05 (d, 1H), 3.78 (d, 1H). |
| 76 | δ 8.47 (s, 1H), 8.26 (s, 1H), 8.16 (s, 1H), 7.82 (d, 1H), 7.51 (s, 2H), 7.50 (d, 1H), 7.45 (s, 1H), 4.10 (d, 1H), 3.72 (d, 1H). |
| 79 | δ 8.30 (d, 2H), 7.85 (d, 2H), 7.74 (m, 1H), 7.51 (s, 2H), 7.45 (s, 1H), 4.11 (d, 1H), 3.73 (d, 1H). |
| 86 | δ 9.25 (s, 1H), 8.98 (s, 2H), 7.84 (m, 2H), 7.66 (m, 2H), 7.53 (s, 2H), 7.43 (s, 1H), 4.13 (d, 1H), 3.75 (d, 1H). |
| 87 | (Acetone-d$_6$) δ 9.26 (s, 1H), 8.72 (s, 1H), 8.62 (s, 1H), 8.29 (m, 2H), 7.96 (m, 2H), 7.70 (s, 2H), 7.65 (s, 1H), 4.48 (d, 1H), 4.33 (d, 1H). |
| 88 | δ 8.87 (m, 1H), 8.64 (m, 1H), 7.90 (m, 1H), 7.78 (m, 2H), 7.66 (m, 2H), 7.53 (s, 2H), 7.44 (s, 1H), 7.42 (m, 1H) 4.13 (d, 1H), 3.74 (d, 1H). |
| 89 | δ 8.89 (s, 1H), 8.22 (s, 1H), 8.11 (s, 1H), 8.09 (d, 1H), 7.93 (d, 1H), 7.77 (s, 1H), 7.70 (s, 2H), 4.14 (d, 1H), 3.77 (d, 1H). |
| 101 | δ 8.11 (d, 1H), 7.68 (s, 1H), 7.6 (m, 3H), 7.44 (m, 3H), 3.77 (d, 1H), 2.65 (s, 3H), 2.63 (m, 1H), 1.32 (d, 6H). |
| 102 | δ 8.06 (d, 1H), 7.65 (s, 1H), 7.58 (d, 1H), 7.51 (s, 2H), 7.44 (s, 1H), 4.39 (d, 1H), 4.10, (d, 1H), 3.72, (d, 1H), 2.674 (s, 3H), 2.67 (m, 1H), 1.1 (d, 6H). |
| 103 | δ 8.04 (d, 1H), 7.67 (s, 1H), 7.58 (d, 1H), 7.50 (s, 2H), 7.44 (s, 1H), 4.97 (t, 1H), 4.1 (d, 1H), 3.71 (m, 3H), 2.68 (s, 3H). |
| 104 | δ 8.02 (d, 1H), 7.69 (s, 1H), 7.6 (m, 3H), 7.4 (m, 3H), 4.94 (t, 1H), 4.1 (d, 1H), 3.79 (d, 1H), 3.7 (m, 1H), 2.68 (s, 3H). |
| 105 | δ 8.13 (d, 1H), 7.68 (s, 1H), 7.64 (d, 1H), 7.5 (s, 2H), 7.44 (s, 1H), 4.1 (d, 1H), 3.72 (d, 1H), 3.25 (d, 2H), 2.73 (s, 3H), 2.1 (m, 1H), 0.98 (m, 6H). |
| 106 | δ 8.11 (d, 1H), 7.72 (d, 1H), 7.68 (s, 1H), 7.65 (d, 1H), 7.53 (d, 1H), 7.46 (d, 1H), 4.1 (d, 1H), 3.7 (d, 1H), 3.24 (d, 2H), 2.72 (s, 3H), 2.13 (m, 1H), 0.98 (m, 6H). |
| 110 | δ 7.99 (d, 1H), 7.67 (s, 1H), 7.6 (d, 1H), 7.52 (s, 2H), 7.44 (s, 1H), 7.3-7.4 (m, 4H), 7.24 (s, 1H), 4.316 (s, 1H), 4.1 (d, 1H), 3.72 (d, 1H), 2.70 (s, 3H), 2.69 (s, 3H). |
| 114 | δ 8.44 (d, 1H), 7.92, (d, 2H), 7.74 (d, 1H), 7.6 (t, 1H), 7.5 (s, 2H), 7.44 (s, 1H), 7.15 (d, 2H), 6.13 (br s, 1H), 4.27 (d, 2H), 4.07 (d, 1H), 3.69 (d, 1H). |
| 120 | δ 8.05 (d, 1H), 7.67 (s, 1H), 7.57 (d, 1H), 7.51 (s, 2H), 7.44 (s, 1H), 4.73 (t, 1H), 4.1 (d, 1H), 3.85 (d, 2H), 3.75 (d, 1H), 2.7 (s, 3H), 2.09 (s, 1H). |
| 205 | δ 7.78 (s, 1H), 7.6 (m, 1H), 7.5 (s, 2H), 7.4 (s, 1H), 7.15 (m, 1H), 4.05 (d, 1H), 3.62 (d, 1H), 2.5 (s, 3H). |
| 207 | δ 8.2 (m, 1H), 8.1 (m, 1H), 8.08 (m, 1H), 7.5 (s, 2H), 7.45 (s, 1H), 4.1 (d, 1H), 3.75 (d, 1H), 2.9 (s, 3H). |
| 210 | δ 7.85 (m, 1H), 7.8 (s, 1H), 7.5 (s, 2H), 7.42 (s, 1H), 7.39 (m, 1H), 4.04 (d, 1H), 3.66 (d, 1H), 3.1 (q, 2H), 1.4 (t, 3H). |
| 211 | δ 8.22 (m, 1H), 8.2 (s, 1H), 8.06 (m, 1H), 7.5 (s, 2H), 7.46 (s, 1H), 4.12 (d, 1H), 3.78 (d, 1H, 3.4 (q, 2H), 1.33 (t, 3H). |
| 212 | (Acetone-d$_6$) δ 8.22 (m, 1H), 8.21 (s, 1H), 8.05 (m, 1H), 7.67 (s, 2H), 7.66 (s, 1H), 4.53 (d, 1H), 4.38 (d, 1H), 3.36 (s, 3H). |
| 213 | (Acetone-d$_6$) δ 8.06 (m, 1H), 7.85 (s, 1H), 7.83 (m, 1H), 7.67 (s, 2H), 7.65 (m, 1H), 4.48 (d, 1H), 4.15 (d, 1H), 3.19 (s, 3H), 2.76 (s, 3H). |
| 214 | δ 8.3 (m, 1H), 8.25 (s, 1H), 8.1 (m, 1H), 7.5 (s, 2H), 7.45 (s, 1H), 4.26 (q, 2H), 4.12 (d, 1H), 3.87 (d, 1H). |

$^a$$^1$H NMR data are in ppm downfield from tetramethylsilane. Couplings are designated by (s)—singlet, (d)—doublet, (t)—triplet, (q)—quartet, (m)—multiplet, (dd)—doublet of doublets, (br s)—broad singlet.

Biological Examples of the Invention

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-D for compound descriptions.

Test A

For evaluating control of diamondback moth (*Plutella xylostella*) the test unit consisted of a small open container with a 12-14 day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77™ Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co. Wheaton, Ill., USA) positioned 1.27 cm (0:5 inches) above the top of each test unit. All experimental compounds in these tests were sprayed at 250 ppm replicated three times. After spraying of the formulated test compound, each test unit was allowed to dry for 1 hour and then a black, screened cap was placed on top. The test units were held for 6 days in a growth chamber at 25° C. and 70% relative humidity. The level of control efficacy of the test compound was then visually assessed based on the foliage feeding damage and the larval mortality of each test unit.

Of the compounds of Formula 1 tested the following provided very good to excellent levels of control efficacy (20% or less feeding damage or 80% or more mortality): 1, 2, 3, 5, 9, 14, 16, 17, 18, 19, 21, 22, 23, 24, 25, 26, 27, 28, 30, 32, 34, 35, 36, 37, 38, 40, 42, 45, 46, 47, 48, 50, 52, 53, 56, 57, 59, 60, 61, 62, 63, 64, 65, 66, 68, 69, 70, 71, 72, 75, 76, 79, 80, 81, 82, 84, 86, 87, 89, 102, 103, 105, 107, 108, 109, 111, 112, 113, 114, 115, 116, 117, 118, 119, 120, 121, 122, 123, 205, 206, 207, 208, 209, 210, 211, 212, 213 and 301.

Test B

For evaluating control of fall armyworm (*Spodoptera frugiperda*) the test unit consisted of a small open container with a 4-5-day-old corn (maize) plant inside. This was pre-infested (using a core sampler) with 10-15 1-day-old larvae on a piece of insect diet.

Test compounds 1, 2 and 3 were formulated and sprayed at 250 ppm as described for Test A. The applications were replicated three times. After spraying, the test units were maintained in a growth chamber and then visually rated as described for Test A.

Of the compounds of Formula 1 tested, the following provided excellent levels of control efficacy (20% or less feeding damage or 80% or more mortality): 1, 2, 5, 9, 11, 14, 16, 17, 18, 19, 21, 22, 23, 24, 25, 26, 27, 28, 29, 30, 31, 32, 33, 34, 35, 36, 37, 38, 40, 42, 43, 44, 45, 46, 47, 48, 50, 52, 53, 56, 57, 58, 59, 60, 61, 62, 63, 65, 66, 68, 69, 70, 71, 72, 74, 75, 76, 79, 80, 81, 82, 86, 89, 105, 107, 108, 110, 111, 112, 113, 115, 117, 118, 119, 120, 121, 122, 123, 202, 205; 206, 207, 208, 209, 210, 211, 212 and 213.

Test C

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The larvae moved onto the test plant as the leaf piece desiccated. After pre-infestation, the soil of the test unit was covered with a layer of sand.

All test compounds were formulated and sprayed at 250 ppm as described for Test A and replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds of Formula 1 tested, the following resulted in 80% or more mortality: 2, 9, 14, 17, 31, 36, 38, 42, 61, 63, 65, 69, 72, 75, 76 and 89.

Test D

For evaluating control of potato leafhopper (*Empoasca fabae* Harris) through contact and/or systemic means, the test unit consisted of a small open container with a 5-6-day-old Longio bean plant (primary leaves-emerged) inside. White sand was added to the top of the soil and one of the primary leaves was excised prior to application. Test compounds were formulated and sprayed at 250 ppm and replicated three times as described for Test A. After spraying, the test units were allowed to dry for 1 hour before they were post-infested with 5 potato leafhoppers (18 to 21 day old adults). A black, screened cap was placed on the top of the cylinder. The test units were held for 6 days in a growth chamber at 19-21° C. and 50-70% relative humidity. Each test unit was then visually assessed for insect mortality.

Of the compounds of Formula 1 tested, the following resulted in 80% or more mortality: 9, 14, 16, 18, 19, 22, 24, 26, 31, 32, 36, 37, 38, 42, 47, 60, 63, 65, 69, 70, 71, 72, 76, 79, 81, 82, 89, 107, 108, 111, 207 and 212.

Test E

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test C, and the soil of the test unit was covered with a layer of sand. Test compounds were formulated and sprayed at 250 ppm as described for Test A. The applications were replicated three times. After spraying of the formulated test compound, each test unit was allowed to dry for 1 hour and then a black screened cap was placed on top. The test units were held for 6 days in a growth chamber at 19-21° C. and 50-70% relative humidity. Each test unit was then visually assessed for insect mortality.

Of the compounds of Formula 1 tested, the following resulted in 80% or more mortality: 2, 9, 14, 19, 26, 32, 35, 38, 42, 69, 76 and 89.

Test F

For evaluating control of the Western Flower Thrips (*Fraukliniella occidentalis*) through contact and/or systemic means, the test unit consisted of a small open container with a 5-7-day-old Longio Bean plant inside.

Test compounds were formulated and sprayed at 250 ppm and replicated three times as described for Test A. After spraying, the test units were allowed to dry for 1 hour, then 22-27 adult thrips were added to the unit and then a black, screened cap was placed on top. The test units were held for 7 days at 25° C. and 45-55% relative humidity. Each test unit was then visually assessed for insect mortality.

Of the compounds of Formula 1 tested, the following resulted in 80% or more mortality: 9, 14, 16, 17, 19, 22, 24, 26, 31, 32, 36, 37, 38, 42, 47, 63, 65, 69, 70, 72, 74, 76, 79, 81, 82, 89, 205, 209, 212 and 301.

Test G

For evaluating control of silverleaf whitefly (*Bemisia tabaci*), the test unit consisted of a 14-21-day-old cotton plant grown in Redi-Earth® media (Scotts Co.) with at least two true leaves infested with 2nd and 3rd instar nymphs on the underside of the leaves.

Test compounds were formulated in no more than 2 mL of acetone and then diluted with water to 25-30 mL. The formulated compounds were applied using a flat fan air-assisted nozzle (Spraying Systems 122440) at 10 psi (69 kPa). Plants were sprayed to run-off on a turntable sprayer. All experimental compounds in this screen were sprayed at 250 ppm and replicated three times. After spraying of the test compound, the test units were held for 6 days in a growth chamber at 50-60% relative humidity and 28° C. daytime and 24° C. nighttime temperature. Then the leaves were removed and then dead and live nymphs were counted to calculate percent mortality.

Of the compounds of Formula 1 tested, the following provided very good to excellent levels of control efficacy (80% or more mortality): 9, 14, 42, 63 and 76.

Test H

For evaluating control of the cat flea (*Ctenocephalides felis* Bouche), a CD-1® mouse (about 30 g, male, obtained from Charles River Laboratories, Wilmington, Mass.) was orally dosed with a test compound in an amount of 10 mg/kg solubilized in propylene glycol/glycerol formal (60:40). Two hours after oral administration of the test compound, approximately 8 to 16 adult fleas were applied to each mouse. The fleas were then evaluated for mortality 48 hours after flea application to the mouse.

Of the compounds tested, the following compounds caused 20% or more mortality: 42*, 65*, 69* and 205.

* means the compound caused 50% or more mortality.

What is claimed is:

1. A compound of Formula 1, an N-oxide, or a salt thereof,

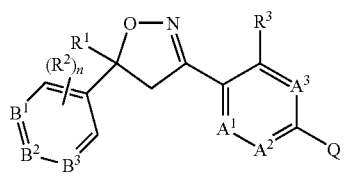

1 wherein:
$A^1$, $A^2$ and $A^3$ are independently $CR^3$;
$B^1$, $B^2$ and $B^3$ are independently $CR^2$;
$R^1$ is $C_1$-$C_3$ alkyl substituted with;
each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;
each $R^3$ is independently H, halogen, $C_1$-$C_6$ alkyl, $C_1$-$C_6$ haloalkyl, $C_2$-$C_6$ alkenyl, $C_3$-$C_6$ haloalkenyl, $C_2$-$C_6$ alkynyl, $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —N($R^4$)$R^5$, —C(W)N($R^4$)$R^5$, —C(W)O$R^5$, —CN or —NO$_2$;
Q is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N($R^4$)$R^5$, —C(W)N($R^4$)$R^5$, —C(O)O$R^5$ and $R^8$; or —S(O)$_2$N($R^{21}$)$R^{22}$, —S(O)$_p$$R^{25}$ or —S(O)(=N$R^{28}$)$R^{29}$;
each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$;

each $R^7$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN, —NO$_2$ or $Q^1$;
each $R^8$ is independently a pyridinyl ring, optionally substituted with one or more substituents independently selected from $R^9$;
each $R^9$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —COOH, —CN or —NO$_2$;
each $Q^1$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, —C(W)N($R^{10}$)$R^{11}$, —C(O)O$R^{11}$ and $R^{12}$;
each $R^{10}$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
each $R^{11}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or $R^{12}$;
each $R^{12}$ is independently a phenyl ring or a pyridinyl ring, each ring optionally substituted with one or more substituents independently selected from $R^{13}$;
each $R^{13}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —COOH, —CN or —NO$_2$;
$R^{21}$ is H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
$R^{22}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{23}$;
each $R^{23}$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$; or a phenyl ring or a pyridinyl ring, each ring optionally substituted with one or more substituents independently selected from $R^{24}$;
each $R^{24}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —COOH, —CN or —NO$_2$;
$R^{25}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{26}$;

each $R^{26}$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylcarbonyl, $C_2$-$C_7$ alkoxycarbonyl, —CN or —$NO_2$; or a phenyl ring or a pyridinyl ring, each ring optionally substituted with one or more substituents independently selected from $R^{27}$;

each $R^{27}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —COOH, —CN or —$NO_2$;

$R^{28}$ is H, halogen, —CN, —$NO_2$, $C_2$-$C_7$ alkylcarbonyl, $C_2$-$C_7$ haloalkylcarbonyl, $C_2$-$C_7$ alkoxycarbonyl, $C_2$-$C_7$ alkylaminocarbonyl, $C_3$-$C_7$ dialkylaminocarbonyl, $C_1$-$C_6$ alkylsulfonyl or $C_1$-$C_6$ haloalkylsulfonyl; or $R^{28}$ is $C_1$-$C_6$ alkyl, $C_3$-$C_6$ cycloalkyl, ($C_1$-$C_6$ alkoxy)-($C_1$-$C_6$ alkyl) or $C_1$-$C_6$ alkylthio, each optionally substituted with halogen, $C_1$-$C_6$ alkyl, $C_1$-$C_6$ haloalkyl, $C_1$-$C_6$ cycloalkyl, $C_1$-$C_6$ halocycloalkyl, $C_1$-$C_6$ alkoxy, $C_1$-$C_6$ haloalkoxy, —CN or —$NO_2$;

$R^{29}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{26}$;

each W is independently O or S;

p is 0, 1 or 2; and n is 1 or 2.

2. A compound of claim 1 wherein each $R^2$ is independently H, halogen, $C_1$-$C_6$ haloalkyl, $C_1$-$C_6$ haloalkoxy or —CN;

each $R^3$ is independently H, halogen, $C_1$-$C_6$ alkyl, $C_1$-$C_6$ haloalkyl, $C_2$-$C_6$ alkenyl, $C_3$-$C_6$ haloalkenyl, $C_2$-$C_6$ alkynyl, $C_3$-$C_6$ haloalkynyl, $C_3$-$C_6$ cycloalkyl, $C_1$-$C_6$ alkoxy, $C_1$-$C_6$ haloalkoxy, —N($R^4$)$R^5$, —C(W)N($R^4$)$R^5$, —CN or —$NO_2$;

each $R^4$ is independently H, $C_1$-$C_4$ alkyl, $C_2$-$C_4$ alkylcarbonyl or $C_2$-$C_4$ alkoxycarbonyl;

each $R^5$ is independently H; or $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^7$;

each $R^7$ is independently halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, —CN, —$NO_2$ or $Q^1$;

$Q^1$ is a phenyl ring, a pyridinyl ring, a thiazolyl ring, a pyrazolyl ring, a triazolyl ring or an imidazolyl ring, each ring optionally substituted with one or more substituents independently selected from halogen, $C_1$-$C_3$ alkyl, $C_1$-$C_3$ haloalkyl, —CN, —C(W)N($R^{10}$)$R^{11}$, C(O)O$R^{11}$ and $R^{12}$;

each $R^{10}$ is independently H, $C_1$-$C_4$ alkyl, $C_2$-$C_4$ alkylcarbonyl or $C_2$-$C_4$ alkoxycarbonyl; and each $R^{11}$ is independently H; or $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl or $R^{12}$.

3. A compound of claim 2 wherein

Q is a phenyl ring, a pyridinyl ring, a pyrimidinyl ring, a triazinyl ring, a pyrazolyl ring, a triazolyl ring, a tetrazolyl ring, an imidazolyl ring, an oxazolyl ring, an isoxazolyl ring, a thiazolyl ring or an isothiazolyl ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —N($R^4$)$R^5$, —C(W)N($R^4$)$R^5$, —C(O)O$R^5$ and $R^8$.

4. A compound of claim 3 wherein each $R^2$ is independently H, $CF_3$, $OCF_3$, halogen or —CN;

each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$;

each $R^4$ is H;

Q is a pyrazolyl ring, a triazolyl ring, a tetrazolyl ring or an imidazolyl ring, each ring attached through nitrogen and optionally substituted with one or more substituents independently selected from halogen, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, —CN, —$NO_2$, —N($R^4$)$R^5$, —C(W)N($R^4$)$R^5$, —C(O)O$R^5$ and $R^8$; and W is O.

5. A compound of claim 4 wherein $B^2$ is CH;

$R^1$ is $CF_3$;

each $R^2$ is independently H or halogen;

each $R^3$ is independently H, halogen, $C_1$-$C_2$ alkyl, —C≡CH, —CN or —$NO_2$; and Q is a pyrazolyl ring, a triazolyl ring, a tetrazolyl ring or an imidazolyl ring, each ring attached through nitrogen and optionally substituted with one or more substituents independently selected from halogen, $C_1$-$C_4$ alkyl, $C_1$-$C_4$ haloalkyl, —CN and —$NH_2$.

6. A compound of claim 2 wherein

Q is —S(O)$_2$N($R^{21}$)$R^{22}$, —S(O)$_p$$R^{25}$ or —S(O)(=$NR^{28}$)$R^{29}$;

$R^{21}$ is H or $C_1$-$C_6$ alkyl;

$R^{22}$ is $C_1$-$C_4$ alkyl optionally substituted with one or more substituents independently selected from $R^{23}$;

each $R^{23}$ is independently halogen, $C_1$-$C_4$ alkylthio, —CN, a phenyl ring or a pyridinyl ring;

$R^{25}$ is $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^{26}$; and each $R^{26}$ is independently halogen, $C_1$-$C_4$ alkoxy, $C_1$-$C_4$ alkylthio, $C_1$-$C_4$ alkylsulfinyl, $C_1$-$C_4$ alkylsulfonyl, —CN or —$NO_2$;

$R^{28}$ is H, halogen, $C_1$-$C_4$ alkyl, —CN, —$NO_2$, $C_2$-$C_7$ haloalkylcarbonyl or $C_2$-$C_7$ alkoxycarbonyl; and $R^{29}$ is $C_1$-$C_4$ alkyl, $C_3$-$C_4$ alkenyl, $C_3$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more substituents independently selected from $R^{26}$.

7. A compound of claim 6 wherein each $R^2$ is independently H, $CF_3$, $OCF_3$, halogen or —CN;

each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —$NO_2$;

each $R^4$ is H;

Q is —S(O)$_2$N($R^{21}$)$R^{22}$;

$R^{21}$ is H or methyl; and

W is O.

8. A compound of claim 7 wherein
$B^2$ is CH;
$R^1$ is $CF_3$;
each $R^2$ is independently H or halogen; and
each $R^3$ is independently H, halogen, $C_1$-$C_2$ alkyl, —C≡CH, —CN or —NO$_2$.

9. A compound of claim 6 wherein
each $R^2$ is independently H, $CF_3$, $OCF_3$, halogen or —CN;
each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —NO$_2$;
each $R^4$ is H;
Q is —S(O)$_p$$R^{25}$;
$R^{25}$ is $C_1$-$C_4$ alkyl optionally substituted with one or more substituents independently selected from $R^{26}$;
each $R^{26}$ is independently halogen or —CN;
W is O; and
p is 1 or 2.

10. A compound of claim 9 wherein
$B^2$ is CH;
$R^1$ is $CF_3$;
each $R^2$ is independently H or halogen; and
each $R^3$ is independently H, halogen, $C_1$-$C_2$ alkyl, —C≡CH, —CN or —NO$_2$.

11. A compound of claim 6 wherein
each $R^2$ is independently H, $CF_3$, $OCF_3$, halogen or —CN;
each $R^3$ is independently H, halogen, $C_1$-$C_4$ alkyl, $C_1$-$C_4$ haloalkyl, $C_2$-$C_4$ alkenyl, $C_3$-$C_4$ haloalkenyl, $C_2$-$C_4$ alkynyl, $C_3$-$C_4$ haloalkynyl, cyclopropyl, $C_1$-$C_4$ alkoxy, —C(W)N($R^4$)$R^5$, —CN or —NO$_2$;
each $R^4$ is H;
Q is —S(O)(=N$R^{28}$)$R^{29}$;
$R^{28}$ is H, $C_1$-$C_4$ alkyl, —CN or —NO$_2$;
$R^{29}$ is $C_1$-$C_4$ alkyl optionally substituted with one or more substituents independently selected from $R^{26}$;
each $R^{26}$ is independently halogen or —CN; and
W is O.

12. A compound of claim 11 wherein
$B^2$ is CH;
$R^1$ is $CF_3$;
each $R^2$ is independently H or halogen; and
each $R^3$ is independently H, halogen, $C_1$-$C_2$ alkyl, —C≡CH, —CN or —NO$_2$.

13. A compound of claim 1 that is selected from the group consisting of:
5-(3,5-dichlorophenyl)-4,5-dihydro-3-[4-(1H-pyrazol-1-yl)phenyl]-5-(trifluoromethyl)isoxazole;
5-(3,5-dichlorophenyl)-4,5-dihydro-3-[3-methyl-4-(1H-pyrazol-1-yl)phenyl]-5-(trifluoromethyl)isoxazole;
2-[4-[5-(3,5-dichlorophenyl)-4,5-dihydro-5-(trifluoromethyl)-3-isoxazolyl]phenyl]pyridine;
5-(3,5-dichlorophenyl)-4,5-dihydro-3-[4-(1H-imidazol-1-yl)phenyl]-5-(trifluoromethyl)isoxazole;
1-[4-[5-(3,5-dichlorophenyl)-4,5-dihydro-5-(trifluoromethyl)-3-isoxazolyl]phenyl]-1H-1,2,4-triazole;
1-[4-[5-(3,5-dichlorophenyl)-4,5-dihydro-5-(trifluoromethyl)-3-isoxazolyl]-2-methylphenyl]-1H-1,2,4-triazole;
1-[4-[5-(3,5-dichlorophenyl)-4,5-dihydro-5-(trifluoromethyl)-3-isoxazolyl]-2-methylphenyl]-1H-1,2,3-triazole;
5-[5-(3,5-dichlorophenyl)-4,5-dihydro-5-(trifluoromethyl)-3-isoxazolyl]-2-(1H-1,2,4-triazol-1-yl)benzonitrile;
5-[5-(3,5-dichlorophenyl)-4,5-dihydro-5-(trifluoromethyl)-3-isoxazolyl]-2-(1H-1,2,3-triazol-1-yl)benzenecarbothioamide;
2-(3-amino-1H-1,2,4-triazol-1-yl)-5-[5-(3,5-dichlorophenyl)-4,5-dihydro-5-(trifluoromethyl)-3-isoxazolyl]benzonitrile;
5-[5-(3,5-dichlorophenyl)-4,5-dihydro-5-(trifluoromethyl)-3-isoxazolyl]-2-(1H-tetrazol-1-yl)benzonitrile;
N-(cyclopropylmethyl)-4-[5-(3,5-dichlorophenyl)-4,5-dihydro-5-(trifluoromethyl)-3-isoxazolyl]-2-methylbenzenesulfonamide;
4-[5-(3,5-dichlorophenyl)-4,5-dihydro-5-(trifluoromethyl)-3-isoxazolyl]-2-methyl-N-(2-pyridinylmethyl)benzenesulfonamide;
5-[5-(3,5-dibromophenyl)-4,5-dihydro-5-(trifluoromethyl)-3-isoxazolyl]-2-(1H-1,2,4-triazol-1-yl)benzonitrile;
5-(3,5-dichlorophenyl)-4,5-dihydro-3-[4-(methylsulfonyl)phenyl]-5-(trifluoromethyl)isoxazole;
5-[5-(3,5-dichlorophenyl)-4,5-dihydro-5-(trifluoromethyl)-3-isoxazolyl]-2-(methylsulfonyl)benzonitrile; and
3-[3-bromo-4-(methylthio)phenyl]-5-(3,5-dichlorophenyl)-4,5-dihydro-5-(trifluoromethyl)isoxazole.

14. A composition comprising a biologically active compound of claim 1 and at least one component selected from the group consisting of a surfactant, a solid diluent and a liquid diluent, said composition optionally further comprising at least one additional biologically active compound or a biologically active agent.

15. A composition for controlling an invertebrate pest comprising a biologically effective amount of a compound of claim 1 and at least one component selected from the group consisting of a surfactant, a solid diluent and a liquid diluent, said composition optionally further comprising at least one additional biologically active compound or a biologically active agent.

16. The composition of claim 15 wherein the additional biologically active compound or the biologically active agent is selected from insecticides of the group consisting of macrocyclic lactones, neonicotinoids, octopamine receptor ligands, ryanodine receptor ligands, ecdysone agonists, sodium channel modulators, chitin synthesis inhibitors, nereisotoxin analogs, mitochondrial electron transport inhibitors, cholinesterase inhibitors, cyclodiene insecticides, molting inhibitors, GABA-regulated chloride channel blockers, juvenile hormone mimics, lipid biosynthesis inhibitors and biological agents including nucleopolyhedrovirus, a member of *Bacillus thuringiensis*, an encapsulated delta-endotoxin of *Bacillus thuringiensis*; and a naturally occurring or a genetically modified viral insecticide.

17. The composition of claim 15 wherein the additional biologically active compound or the biologically active agent is selected from the group consisting of abamectin, acephate, acetamiprid, acetoprole, aldicarb, amidoflumet, amitraz, avermectin, azadirachtin, azinphos-methyl, bifenthrin, bifenazate, bistrifluoron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron, *Bacillus thuringiensis* subsp. *aizawai, Bacillus thuringiensis* subsp. *kurstaki*, nucleopolyhedrovirus, an encapsulated delta-endotoxin of *Bacillus thuringiensis*, baculovirus, entomopathogenic bacteria, entomopathogenic virus and entomopathogenic fungi.

18. The composition of claim 17 wherein the additional biologically active compound or the biologically active agent is selected from the group consisting of abamectin, acetamiprid, amitraz, avermectin, azadirachtin, bifenthrin, buprofezin, cartap, chlorantraniliprole, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flubendiamide, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai, Bacillus thuringiensis* subsp. *kurstaki*, nucleopolyhedrovirus and an encapsulated delta-endotoxin of *Bacillus thuringiensis*.

19. The composition of claim 15 in the form of a soil drench liquid formulation.

20. A spray composition for controlling an invertebrate pest, comprising:
(a) a biologically effective amount of the compound of claim 1 or the composition of claim 15; and
(b) a propellant.

21. A bait composition for controlling an invertebrate pest, comprising:
(a) a biologically effective amount of the compound of claim 1 or the composition of claim 15;
(b) one or more food materials;
(c) optionally an attractant; and
(d) optionally a humectant.

22. A trap device for controlling an invertebrate pest, comprising:
(a) the bait composition of claim 21; and
(b) a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

23. A method for controlling an invertebrate pest comprising contacting the invertebrate pest or its environment with a biologically effective amount of a compound of claim 1.

24. A method for controlling an invertebrate pest comprising contacting the invertebrate pest or its environment with a composition of claim 15.

25. The method of claim 24 wherein the environment is soil and the composition is applied to the soil as a soil drench formulation.

26. A method for controlling a cockroach, an ant or a termite, comprising contacting a cockroach, an ant, or a termite with the bait composition in the trap device of claim 22.

27. A method for controlling a mosquito, a black fly, a stable fly, a deer fly, a horse fly, a wasp, a yellow jacket, a hornet, a tick, a spider, an ant, or a gnat, comprising contacting a mosquito, a black fly, a stable fly, a deer fly, a horse fly, a wasp, a yellow jacket, a hornet, a tick, a spider, an ant, or a gnat with the spray composition of claim 20 dispensed from a spray container.

28. A method for protecting a seed from an invertebrate pest comprising contacting the seed with a biologically effective amount of a compound of claim 1.

29. The method of claim 28 wherein the seed is coated with the compound of claim 1 formulated as a composition comprising a film former or adhesive agent.

30. A treated seed comprising a compound of claim 1 in an amount of from about 0.0001 to 1% by weight of the seed before treatment.

31. A composition for protecting an animal from an invertebrate parasitic pest comprising a parasiticidally effective amount of a compound of claim 1 and at least one carrier.

32. The composition of claim 31 in a form for oral administration.

33. A method for protecting an animal from an invertebrate parasitic pest comprising administering to the animal a parasiticidally effective amount of a compound of claim 1.

* * * * *

UNITED STATES PATENT AND TRADEMARK OFFICE
CERTIFICATE OF CORRECTION

| | | |
|---|---|---|
| PATENT NO. | : 7,897,630 B2 | Page 1 of 1 |
| APPLICATION NO. | : 12/083944 | |
| DATED | : March 1, 2011 | |
| INVENTOR(S) | : George Philip Lahm et al. | |

It is certified that error appears in the above-identified patent and that said Letters Patent is hereby corrected as shown below:

Column 111, line 32 (claim 1, line 6) should read:

--$R^1$ is $C_1$-$C_3$ alkyl substituted with halogens;--

Signed and Sealed this

Seventeenth Day of May, 2011

David J. Kappos
*Director of the United States Patent and Trademark Office*